US008309703B2

(12) United States Patent
Goregaoker et al.

(10) Patent No.: US 8,309,703 B2
(45) Date of Patent: Nov. 13, 2012

(54) COMPOSITIONS AND METHODS FOR SHORT INTERFERING NUCLEIC ACID INHIBITION OF $NA_V1.8$

(75) Inventors: Sameer Goregaoker, San Diego, CA (US); John C. Hunter, Warren, NJ (US); Tony Priestley, West Chester, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 211 days.

(21) Appl. No.: 12/789,564

(22) Filed: May 28, 2010

(65) Prior Publication Data

US 2010/0305192 A1    Dec. 2, 2010

Related U.S. Application Data

(62) Division of application No. 11/259,588, filed on Oct. 26, 2005, now Pat. No. 7,786,291.

(60) Provisional application No. 60/622,484, filed on Oct. 27, 2004.

(51) Int. Cl.
    *C07H 21/02* (2006.01)
    *C07H 21/04* (2006.01)
    *C12Q 1/68* (2006.01)
    *C12P 19/34* (2006.01)

(52) U.S. Cl. ....... 536/24.5; 435/6; 435/91.1; 435/91.31; 536/23.1; 536/24.31

(58) Field of Classification Search ............. 435/6, 91.1, 435/91.31; 536/23.1, 24.5, 24.31
    See application file for complete search history.

(56) References Cited

U.S. PATENT DOCUMENTS

| 6,451,554 | B1 | 9/2002 | Wood et al. |
| 6,506,559 | B1 | 1/2003 | Fire et al. |
| 2004/0248207 | A1 | 12/2004 | Okuse et al. |

FOREIGN PATENT DOCUMENTS

| WO | WO 03/016917 | 2/2003 |
| WO | WO 2004/022075 | 3/2004 |
| WO | WO 2004/087956 | 10/2004 |
| WO | WO 2005/014782 | 2/2005 |

OTHER PUBLICATIONS

Agrawal, J. B., et al., Molecular Med. Today, vol. 6, pp. 72-81 (2000).
Anderson, "Human Gene Therapy", Nature, vol. 392, pp. 25-30 (1998).
Branch, A; Trends in Biochem. Sci., vol. 23, pp. 45-50 (1998).
Burton et al, "Replication-Defective Genomic HSV Gene Therapy Vectors: Design, Production and CNS Applications", Current Opinion in Molecular Therapy, vol. 7, No. 10, pp. 326-336 (2005).
Brummelkamp et al., "A System for Stable Expression of Short Interfering RNAs in Mammalian Cells", Science, 296:550-553 (Apr. 19, 2002).
Chirila, T. et al., Biomaterials, vol. 23, pp. 321-342 (2002).
Crooke, S.T.; Annu. Rev. Med.; vol. 55, pp. 61-95 (2004).
Dong, X.W., et al.; "Small interfering RNA-Mediated selective knockdown of Nav1.8 Tetrodotoxin-Resistant Sodium Channel Reverses Mechanical Allodynia in Neuropathic Rats"; Neuroscience; 148:812-821 (2007).
Dornburg, "Reticuloendotheliosis Viruses and Derived Vectors", Gene Therapy, vol. 2, pp. 301-310 (1995).
Eglitis and Anderson, "Retroviral Vectors for Introduction of Genes into Mammalian Cells", BioTechniques, vol. 6, No. 7, pp. 608-614 (1988).
Elbashir et al., "Analysis of gene function in somatic mammalian cells using small interfering RNAs", Methods, 26:199-213 (2002).
Elbashir et al., "Duplexes of 21-nucleotide RNAs mediate RNA interference in cultured mammalian cells", Nature, 411:494-498 (May 24, 2001).
Gold et al., "Redistribution of $Na_v1.8$ in Uninjured Axons Enables Neuropathic Pain", The Journal of Neuroscience, 23(1):158-166 (Jan. 1, 2003).
Goregaoker et al., "siRNA-mediated knockdown of the Nav1.8 sodium channel", The Journal of Pain, 6(3S), Supplement 1 p. S9 (Mar. 2005).
Khasar et al., "A tetrodotoxin-resistant sodium current mediates inflammatory pain in the rat", Neuroscience Letters, 256:17-20 (Oct. 30, 1998).
Kim et al., "An experimental model for peripheral neuropathy produced by segmental spinal nerve ligation in the rat", Pain, 50:355-363 (1992).
Kurreck, "Antisense and RNA interference approaches to target validation in pain research", Current Opinion in Drug Discovery and Development, 7(2):179-187 (2004).
Lai et al., "Inhibition of neurophathic pain by decreased expression of the tetrodotoxin-resistant sodium channel, NaV1.8", Pain, 95:143-152 (2002).
Lai et al., "Voltage-Gated Sodium Channels and Hyperalgesia", Annual Review of Pharmacology and Toxicology, 44:371-397 (2004).
Lee et al., "Expression of small interfering RNAs targeted against HIV-1 rev transcripts in human cells", Nature Biotechnology, 19:500-505 (May 2002).
Mikami et al., "Short Hairpin RNA-mediated Selective Knockdown of Nav1.8 Tetrodotoxin-resistant Voltage-gated Sodium Channel in Dorsal Root Ganglion Neurons", Anesthesiology, 103(4):828-836 (Oct. 2005).
Miller, "Retrovirus Packaging Cells", Human Gene Therapy, vol. 1, pp. 5-14 (1990).
Miyagishi et al., "U6 promoter-driven siRNAs with four uridine 3' overhangs efficiently suppress targeted gene expression in mammalian cells", Nature Biotechnology, 19:497-500.

(Continued)

*Primary Examiner* — Jane Zara

(57) ABSTRACT

The invention provides short interfering nucleic acids, either single-stranded or double-stranded, that cause RNAi-induced degradation of mRNA from the $Na_v1.8$ sodium channel gene; to pharmaceutical compositions comprising such short interfering nucleic acids; recombinant vectors comprising such short interfering nucleic acids; a method for inhibiting translation of an mRNA; a method for inhibiting expression of a polypeptide; a method for blocking the membrane potential in a cell; a method for blocking the sodium current in a cell; and a method for inhibiting chronic pain.

14 Claims, No Drawings

OTHER PUBLICATIONS

Novakovic et al., "Distribution of the Tetrodotoxin-Resistant Sodium Channel PN3 in Rat Sensory Neurons in Normal and Neuropathic Conditions", *The Journal of Neuroscience*, 18(6):2174-2187 (Mar. 15, 1998).

Opalinska, J. B., et al., Nature Reveiws, vol. 1, pp. 503-514 (2002).

Paddison et al., "Short hairpin RNAs (shRNAs) induce sequence-specific silencing in mammalian cells", *Genes & Development*, 16:948-958 (2002).

Paul et al., "Effective expression of small interfering RNA in human cells", *Nature Biotechnology*, 20:505-508 (May 2002).

Peracchi, A. et al., Rev. Med. Virol., vol. 14, pp. 47-64 (2004).

Porreca et al., "A comparison of the potential role of the tetrodotoxin-insensitive sodium channels, PN3/SNS and NaN/SNS2, in rat models of chronic pain", *Proc. Natl. Acad. Sci USA*, 96:7640-7644 (Jul. 1999).

Reynolds, A. et al., Nature Biotech., vol. 22, No. 3, pp. 326-330 (2004).

Yeomans et al, "Decrease in Inflammatory Hyperalgesia by Herpes Vector-Mediated Knockdown of $Na_v1.7$ Sodium Channels in Primary Afferents", Human Gene Therapy, vol. 16, pp. 271-277 (2005).

Sui et al., "A DNA vector-based RNAi technology to suppress gene expression in mammalian cells", Proc. Nat. Acad. Sci., 99(8):5515-5520 (Apr. 16, 2002).

Tuschl et al., "Targeted mRNA degradation by double-stranded RNA in vitro", *Genes & Development*, 13:3191-3197 (1999).

Tuschl, "Expanding small RNA interference", *Nature Biotechnology*, 20:446-448 (May 2002).

Vickers, T. A., et al., J. Biol. Chem., vol. 278, No. 9, pp. 7108-7118 (2003).

Wood et al., "Voltage-Gated Sodium Channels and Pain Pathways", *Journal of Neurobiology*, 61(1):55-71 (Oct. 2004).

Yoshimura et al., "The Involvement of the Tetrodotoxin-Resistant Sodium Channel $Na_v1.8$ (PN3/SNS) in a Rat Model of Visceral Pain", *The Journal of Neuroscience*, 21(21):8690-8696 (Nov. 1, 2001).

GenBank Accession No. NM 017247 (Rat Nucleic Acid Sequence NaV1.8) dated Oct. 1, 2008.

GenBank Accession No. XM 346840 dated Oct. 24, 2003 (Replaced by NM 017247).

GenBank Accession No. X92184 dated Apr. 18, 2005 (Reference Sequence for NM 017247).

GenBank Database Accession No. NP 058943 (Rat Amino Acid Sequence NaV1.8) dated Oct. 1, 2008.

GenBank Database Accession No. XP346841 dated Oct. 24, 2003 (Replaced by NP 058943).

GenBank Database Accession No. AF 117907 (Human Nucleic Acid Sequence) dated May 18, 1999.

GenBank Database Accession No. AAD 30863 (Human Amino Acid Sequence) dated May 18, 1999.

PCT International Search Report mailed May 15, 2006 for corresponding PCT Application No. PCT/US2005/038792.

COMPOSITIONS AND METHODS FOR SHORT INTERFERING NUCLEIC ACID INHIBITION OF $Na_v1.8$

CROSS-REFERENCE TO RELATED APPLICATIONS

This application is a divisional application of U.S. Ser. No. 11/259,588 filed Oct. 26, 2005 now U.S. Pat. No. 7,786,291 which claims the benefit of priority under 35 USC 119(e) of provisional patent application U.S. Ser. No. 60/622,484 filed Oct. 27, 2004, the disclosures of which is hereby incorporated by reference in its entirety.

BACKGROUND OF THE INVENTION

1. Field of the Invention

The invention provides short interfering nucleic acids, either single-stranded or double-stranded, that cause RNAi-induced degradation of mRNA from the $Na_v1.8$ sodium channel gene; to pharmaceutical compositions comprising such short interfering nucleic acids; recombinant vectors comprising such short interfering nucleic acids; a method for inhibiting translation of an mRNA; a method for inhibiting expression of a polypeptide; a method for blocking the membrane potential in a cell; a method for blocking the sodium current in a cell; and a method for inhibiting chronic pain.

2. Background of the Invention

Chronic pain is a major symptom of peripheral neuropathies, whether induced by AIDS, cancer chemotherapy, diabetes, or by direct physical trauma to the peripheral nerves. Such neuropathic pain is often highly debilitating and resistant to therapeutic intervention.

Animal models of neuropathic pain have suggested that a prominent feature in the maintenance of the neuropathic state is an abnormal, persistent hyperexcitability of the sensory afferent neurons within the peripheral nerve following injury. In addition, a common clinical finding is that broad-spectrum sodium channel blockers, such as lidocaine, can acutely suppress neuropathic pain. However, the relative contribution of individual sodium channel subtypes in neuropathic pain remains unclear.

Voltage-gated sodium channels are critical for the initiation and propagation of action potentials in neurons. In addition, these channels are involved in the regulation of neuronal excitability. Therefore, voltage-gated sodium channels play an important role in transmitting nociceptive information throughout both the peripheral and central nervous systems. Peripheral nerve injury causes sodium channels to accumulate in the membranes of primary afferents around the site of injury. This results in repetitive firing and an increase in excitability of both injured afferents and their uninjured neighbors. This increase in excitability appears to be critical for the expression of neuropathic pain.

At least ten different isoforms of sodium channels have been identified in the brain, neurons and striated muscles. The major component of sodium channels is the 260 kDa α-subunit, which forms the pore of the channel. The α-subunit is composed of four homologous domains, DI, DII, DIII and DIV, each of which is composed of six transmembrane segments, S1-S6. Most sodium channels associate with auxiliary β-subunits, β1-β4, which have an average molecular weight of 30 kDa. The β-subunits modulate the level of expression and gating of these channels.

Three sodium channel isoforms, $Na_v1.7$, $Na_v1.8$ and $Na_v1.9$, are expressed primarily in the PNS. $Na_v1.7$ is widespread in the peripheral nervous system, such that it is present in all types of dorsal root ganglion neurons, in Schwann cells and in neuroendocrine cells. $Na_v1.7$ is sensitive to nanomolar amounts of tetrodotoxin. $Na_v1.8$ is found only in sensory afferent nerves and neurons of the dorsal root ganglion and trigeminal ganglion. The $Na_v1.8$ channel is highly resistant to tetrodotoxin, with an $IC_{50}$ of greater than 50 μM. $Na_v1.9$ is also expressed in small fibers of the dorsal root ganglion and trigeminal ganglion and is also resistant to nanomolar concentrations of tetrodotoxin, but is half maximally blocked by ~40 μM of tetrodotoxin.

Recent interest in the search for therapeutic targets in the treatment of pain has focused on the tetrodotoxin resistant sodium channels found in adult dorsal root ganglion neurons, a significant fraction of which are known to be pain-sensing 'nociceptors'. One such sodium channel is $Na_v1.8$, which was formerly known as PN3 or peripheral nerve sodium channel type 3. This channel has been found to be upregulated in the dorsal root ganglion in chronic pain states. In addition, the biophysical properties of $Na_v1.8$ make this channel a likely candidate for maintaining the sustained repetitive firing of the peripheral neuron following injury. Moreover, the expression of $Na_v1.8$ being restricted to the periphery in sensory neurons of the dorsal root ganglion, suggests that blockade of this channel might allow relief from neuropathic pain with minimal side effects. However, this possibility can not be tested pharmacologically because currently available sodium channel blockers do not distinguish between sodium channel subtypes.

Antisense oligodeoxynucleotide targeting of $Na_v1.8$ expression in an animal model of neuropathic pain has been employed to test whether a selectively attenuated expression of this channel might allow relief from neuropathic pain. See Porreca et al., "A comparison of the potential role of the tetrodotoxin-insensitive sodium channels, PN3/SNS and NaN/SNS2, in rat models of chronic pain", *Proc. Nat. Acad. Sci.*, vol. 96, pp. 7640-7644 (1999). Inhibition of $Na_v1.8$ expression using antisense deoxyoligonucleotides has also been found to inhibit chronic pain in other animal pain models. See Yoshimura et al., "The involvement of the tetrodotoxin-resistant sodium channel $Na_v1.8$ (PN3/SNS) in a rat model of visceral pain", *J. Neuroscience*, vol. 21, pp. 8690-8696 (2001); and Khasar et al., "A tetrodotoxin-resistant sodium current mediates inflammatory pain in the rat", *Neuroscience Letters*, vol. 256, no. 1, pp. 17-20 (1998). Further data indicate that selective knock-down of $Na_v1.8$ protein in the dorsal root ganglion neurons by specific antisense oligodeoxynucleotides to $Na_v1.8$ prevented the hyperalgesia and allodynia caused by spinal nerve ligation injury. See Kim et al., "An experimental model for peripheral neuropathy produced by segmental spinal nerve ligation in the rat", *Pain*, vol. 50, pp. 355-363 (1992). The above data suggests a pathophysiological role for $Na_v1.8$ in several peripheral neuropathic and inflammatory states.

However, the use of antisense oligodeoxynucleotides as therapeutics is limited by their instability in vivo, by their limited efficacy and by their tendency to produce 'off-target' effects. Since no small molecule has been identified that is capable of specifically blocking $Na_v1.8$, there is a continued need for alternative ways of modulating $Na_v1.8$ in the treatment of pain.

The present invention meets the above need by providing short interfering nucleic acids and siRNAs to specifically knock-down expression of $Na_v1.8$. The use of siRNA is attractive because it has high target specificity, reduced off-target liability and achieves high levels of suppression. siRNA, which stands for short interfering RNA or small interfering RNA, is a form of RNA interference (RNAi). RNAi is a technique used to investigate gene function by degrading a specific mRNA target in a cell, thus knocking-out or knocking-down the level of the encoded protein. The mechanism of action of siRNA is thought to involve a multi-step process. First, double-stranded RNA (dsRNA) is recognized by an RNase III family member and is cleaved into siRNAs of 21 to 23 nucleotides. Next, the siRNAs are incorporated into an RNAi targeting complex called RNA-induced silencing complex (RISC). RISC is a dual function helicase and RNase that recognizes target mRNA. After recognizing a target mRNA, the RISC binds the mRNA and unwinds the siRNA, which allows the antisense strand of the siRNA to bind via complementary base pairing (Watson-Crick base pairing) to the target mRNA. This causes hydrolysis and destruction of the mRNA, which results in decreased protein expression. Furthermore, siRNA is apparently recycled such that one siRNA molecule is capable of inducing cleavage of approximately 1000 mRNA molecules. Therefore, siRNA-mediated RNAi is more effective than other currently available technologies for inhibiting expression of a target gene.

All references, publications, patent applications and patents disclosed herein are hereby incorporated by reference in their entirety.

BRIEF SUMMARY OF THE INVENTION

The present invention is directed to short interfering nucleic acids that specifically target and cause RNAi-induced degradation of mRNA from the $Na_v1.8$ sodium channel gene and methods of using such short interfering nucleic acids.

An embodiment of the invention provides an isolated or recombinant short interfering nucleic acid comprising a nucleotide sequence selected from the group consisting of SEQ ID NOs: 1, 2, 3, 4, 5, 6, 7, 8, 9, 10 and 11, or an analogue thereof. The isolated or recombinant short interfering nucleic acid may further comprise a 3' overhang. Also provided is a pharmaceutical composition comprising one or more of any of the above short interfering nucleic acids and a pharmaceutically acceptable carrier.

An alternative embodiment of the invention provides an isolated or recombinant short interfering nucleic acid comprising a nucleotide sequence selected from the group consisting of SEQ ID NOs: 1, 2, 3, 4, 5, 6, 7, 8, 9, 10 and 11, or an analogue thereof, and further comprising a complementary nucleotide sequence thereto. The isolated or recombinant short interfering nucleic acid may further comprise a 3' overhang. Also provided is a pharmaceutical composition comprising one or more of any of the above short interfering nucleic acids and a pharmaceutically acceptable carrier.

Another embodiment provides an isolated or recombinant short interfering nucleic acid comprising a nucleotide sequence selected from the group consisting of SEQ ID NOs: 1, 2, 3, 4, 5, 6, 7, 8, 9, 10 and 11, or an analogue thereof, and further comprising a complementary nucleotide sequence thereto, wherein the nucleotide sequence and the complementary nucleotide sequence hybridize to form a duplex. The nucleotide sequence and the complementary nucleotide sequence may each further comprise a 3' overhang. Also provided is a pharmaceutical composition comprising one or more of any of the above duplexes and a pharmaceutically acceptable carrier.

An additional embodiment provides an isolated or recombinant short interfering nucleic acid comprising a sense strand and an antisense strand, wherein the sense strand and the antisense strand hybridize to form a duplex, wherein the sense strand comprises a nucleotide sequence substantially identical to a target sequence, and wherein the target sequence is selected from the group consisting of SEQ ID NOs: 12-577. The sense strand and the antisense strand may each further comprise a 3' overhang. Also provided is a pharmaceutical composition comprising one or more of any of the above duplexes and a pharmaceutically acceptable carrier.

An embodiment of the invention provides a recombinant vector comprising one or more of a nucleotide sequence selected from the group consisting of SEQ ID NOs: 1, 2, 3, 4, 5, 6, 7, 8, 9, 10 and 11, or an analogue thereof.

Another embodiment provides a method for inhibiting translation of an mRNA to a polypeptide comprising contacting a cell capable of expressing a $Na_v1.8$ mRNA with one or more isolated or recombinant short interfering nucleic acid comprising a nucleotide sequence selected from the group consisting of SEQ ID NOs: 1, 2, 3, 4, 5, 6, 7, 8, 9, 10 and 11, or an analogue thereof.

An alternative embodiment provides a method for inhibiting expression of a polypeptide comprising contacting a cell capable of expressing a $Na_v1.8$ polypeptide with one or more isolated or recombinant short interfering nucleic acid comprising a nucleotide sequence selected from the group consisting of SEQ ID NOs: 1, 2, 3, 4, 5, 6, 7, 8, 9, 10 and 11, or an analogue thereof.

Another alternative embodiment provides a method for blocking the $Na_v1.8$ derived membrane potential in a cell comprising contacting a cell expressing a $Na_v1.8$ polypeptide, with one or more isolated or recombinant short interfering nucleic acid comprising a nucleotide sequence selected from the group consisting of SEQ ID NOs: 1, 2, 3, 4, 5, 6, 7, 8, 9, 10 and 11, or an analogue thereof.

An additional embodiment provides a method for blocking the $Na_v1.8$ derived sodium ion flux in a cell comprising contacting a cell expressing a $Na_v1.8$ polypeptide with one or more isolated or recombinant short interfering nucleic acid comprising a nucleotide sequence selected from the group consisting of SEQ ID NOs: 1, 2, 3, 4, 5, 6, 7, 8, 9, 10 and 11, or an analogue thereof.

A further embodiment provides a method for inhibiting chronic pain comprising administering to a subject in need thereof an effective amount of a pharmaceutical composition comprising one or more isolated or recombinant short interfering nucleic acid comprising a nucleotide sequence selected from the group consisting of SEQ ID NOs: 1, 2, 3, 4, 5, 6, 7, 8, 9, 10 and 11, or an analogue thereof, and a pharmaceutically acceptable carrier. The above isolated or recombinant short interfering nucleic acid may further comprise a 3' overhang.

DETAILED DESCRIPTION OF THE INVENTION

All publications cited herein are incorporated by reference in their entirety.

Definitions

The term "antisense strand", as used in this application, means a nucleic acid sequence that is complementary to a sense strand.

The term "chronic pain", as used in this application, is defined as pain that lasts for a long period of time The term "complementary", as defined in this application, means a nucleotide sequence that exhibits Watson-Crick base pairing with another nucleotide sequence, i.e., a purine binds to a pyrimidine. For example, a nucleotide sequence may represent a sense strand while the complementary nucleotide sequence thereto may represent the antisense strand.

The term "duplex", as used herein, means two complementary nucleic acid sequences that have hybridized, such as a sense strand and an antisense strand.

The terms "express", "expresses" and "expression", as used herein, mean the molecular biological process by which transcription and translation of a nucleic acid produce a polypeptide, i.e., the process by which genetic information flows from genes to proteins, and by which the effects of genes are manifested.

The terms "homology" and "homologous" refer to a comparison between two nucleic acid sequences, such that when the sequences are aligned and compared, they exhibit similarities. Homology between two nucleic acid sequences can be determined by sequence comparison or based upon hybridization conditions. Nucleotide sequence homology is observed when there is identity in nucleotide residues in two sequences (or in their complementary strands) when optimally aligned to account for nucleotide insertions or deletions. Homology also exists when one nucleotide sequence will hybridize to another sequence under selective hybridization conditions. Stringency of conditions employed in hybridizations to establish homology are dependent upon such factors as salt concentration, temperature, the presence of organic solvents, and other parameters.

The term "knock-down", as used in this application, means to decrease the level of expression of mRNA, such that translation of mRNA to protein is diminished.

The term "knock-out", as defined in this application, means to prevent expression of mRNA, such that translation of mRNA to protein does not occur.

The term "mRNA", as used herein, means messenger RNA.

The term "membrane potential", as used herein, means the difference in electrical charge across both sides of a cell membrane.

The term "pain", as used in this application, means physical pain, such as an uncomfortable sensation in the body, ranging from slight uneasiness to extreme distress or torture, that is usually the result of disease, injury or stress; or mental pain, such as uneasiness of the mind, mental distress, anguish, anxiety or grief.

The term "RNAi", as used in this application, means RNA interference, which is a technique used to investigate gene function by degrading a specific mRNA target in a cell or organism, thus knocking-out or knocking-down the level of the encoded protein. This is also referred to as RNA silencing.

The term "sense strand", as used in this application, means the coding strand of a nucleic acid.

The term "siRNA", as used in this application, means either short or small interfering ribonucleic acid, which is one of the types of RNA silencing mechanisms of RNA interference.

The term "short interfering nucleic acid", as defined in this application, means short interfering stretches of either deoxyribonucleic acids (DNA), ribonucleic acids (RNA) or combinations of both. The term also includes modifications to the nucleic acids and non-traditional bases. Preferably, the short interfering nucleic acid is an siRNA.

The term "sodium current", as used herein, means the part of a cell's membrane potential that is due to the effects of sodium ions.

The term "subject" means both human and non-human animals.

The term "transfect", as used in this application, means the introduction of a nucleic acid into a cell, such as through the use of a virus.

The term "transcription", as defined in this application, means the molecular biological process by which a single-stranded RNA is synthesized from a double-stranded DNA.

The term "translation", as used in this application, means the molecular biological process by which a polypeptide is synthesized from a mRNA.

The term "treatment", as defined herein, means therapeutic, prophylactic or suppressive measures for a disease or disorder leading to any clinically desirable or beneficial effect, including, but not limited to, alleviation of one or more symptoms, regression, slowing or cessation of progression of the disease or disorder.

$Na_v1.8$ Characterization

The $Na_v1.8$ sodium channel comprises an alpha subunit and at least one beta subunit. The nucleotide sequence of the complete open reading frame and the corresponding amino acid sequence of $Na_v1.8$ are known in the art. For example, both the nucleic acid and the amino acid sequence for rat $Na_v1.8$ may be found in SEQ ID NOs: 1 and 2, respectively, of U.S. Pat. No. 6,451,554. The nucleic acid sequence and amino acid sequence for $Na_v1.8$ and its subunits may also be found in the GenBank® database, as shown in Table 1 below.

TABLE 1

| species | GenBank ® No. for Nucleic Acid Sequence | GenBank ® No. for Amino Acid Sequence |
|---|---|---|
| rat | NM 017247 | NP 058943 |
| human | AF 117907 | AAD 30863 |

The human $Na_v1.8$ gene has a high degree of homology, approximately 82%, with the rat $Na_v1.8$ gene. Therefore, human $Na_v1.8$ short interfering nucleic acids corresponding to rat $Na_v1.8$ short interfering nucleic acids that are capable of knock-down of the rat $Na_v1.8$ sodium channel are likely to be effective in the knock-down of the human $Na_v1.8$ sodium channel.

Nucleic Acids

Compositions and methods comprising short interfering nucleic acids targeted to $Na_v1.8$ mRNA are advantageously used to knock-down or knock-out expression of the $Na_v1.8$ sodium channel for the treatment of chronic pain. Specifically, the short interfering nucleic acids of the invention cause RNAi-mediated destruction of the $Na_v1.8$ mRNA.

The $Na_v1.8$ sodium channel is upregulated in the dorsal root ganglion in chronic pain states. Therefore, short interfering nucleic acid sequences capable of knocking-down or knocking-out the expression of $Na_v1.8$ mRNA, as well as $Na_v1.8$ function should be useful in blocking or treating chronic pain.

The present invention, therefore, provides isolated or recombinant short interfering nucleic acids. As used herein, the term "isolated" means a nucleic acid, such as an RNA or DNA molecule, or a mixed polymer, which is substantially separated from other components that are normally found in cells or in recombinant expression systems. These components include, but are not limited to, ribosomes, polymerases, serum components, and flanking genomic sequences. The term thus embraces a short interfering nucleic acid that has been removed from its naturally occurring environment, and includes recombinant or cloned short interfering nucleic acid isolates and chemically synthesized analogs or analogs biologically synthesized by heterologous systems. A substantially pure molecule includes isolated forms of the molecule.

An isolated nucleic acid will generally be a homogeneous composition of molecules but may, in some embodiments, contain minor heterogeneity. Such heterogeneity is typically found at the ends of nucleic acid coding sequences or in regions not critical to a desired biological function or activity.

A "recombinant" short interfering nucleic acid is defined either by its method of production or structure. Some recombinant nucleic acids are thus made by the use of recombinant DNA techniques that involve human intervention, either in manipulation or selection. Others are made by fusing two fragments that are not naturally contiguous to each other. Engineered vectors are encompassed, as well as nucleic acids comprising sequences derived using any synthetic oligonucleotide process.

The short interfering nucleic acids may be either single-stranded or double-stranded. A single-stranded short interfering nucleic acid comprises a sense strand while a double-stranded short interfering nucleic acid comprises both a sense strand and an antisense strand. Preferably, the sense and antisense strands in the double-stranded short interfering nucleic acids hybridize by standard Watson-Crick base-pairing interactions to form a duplex or are connected by a single-stranded hairpin area. It is believed that the hairpin area of the latter type of siRNA molecule is cleaved intracellularly by the "Dicer" protein, or its equivalent, to form an siRNA of two individual base-paired RNA molecules.

The short interfering nucleic acids may range in length from 17 to 29 nucleotides, preferably 19 to 25 nucleotides, more preferably 21-23 nucleotides, and most preferably 21 nucleotides.

Preferably, the short interfering nucleic acid is an siRNA. That is, all of the nucleotides in the sequence are ribonucleotide bases.

However, the present invention also encompasses analogues of the small interfering nucleic acids. Analogues of short interfering nucleic acids contain additions, deletions, alterations, substitutions or modifications of one or more nucleotide bases. For example, the short interfering nucleic acids can be altered, substituted or modified to contain one or more deoxyribonucleotide bases or non-traditional bases or any combination of these.

Preferably, one or both strands of a short interfering nucleic acid of the invention comprises a 3' overhang. As used herein, a "3' overhang" refers to at least one unpaired nucleotide extending from the 3'-end of a short interfering nucleic acid strand. The 3' overhang may range from 1 to 6 nucleotides (which includes ribonucleotides or deoxyribonucleotides), preferably from 1 to 5 nucleotides, more preferably from 1 to 4 nucleotides, particularly preferably from 2 to 4 nucleotides, and most preferably 2 nucleotides.

In another embodiment of the invention, both the sense and antisense strands of the duplex comprise 3' overhangs. The length of the overhangs can be the same or different for each strand of the duplex. Most preferably, a 3' overhang is present on both strands of the duplex, and the overhang for each strand is 2 nucleotides in length. For example, each strand of the duplex can comprise 3' overhangs of dithymidylic acid ("tt") or diuridylic acid ("uu").

In order to enhance the stability of the short interfering nucleic acids, the 3' overhangs can also be stabilized against degradation. In one embodiment, the 3' overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

The short interfering nucleic acids are targeted to a $Na_v1.8$ target mRNA. As used herein, short interfering nucleic acids that are "targeted to a $Na_v1.8$ target mRNA" means either a single-stranded or double-stranded short interfering nucleic acid in which the sense strand has a nucleotide sequence that is either identical or substantially identical to that of a target mRNA and is capable of inducing RNAi-mediated degradation of the mRNA. Of course, the antisense strand of a double-stranded siRNA will have a sequence that is complementary to both the sense strand of the siRNA and the target mRNA.

As used herein, a short interfering nucleic acid that is "substantially identical" to a target sequence is a nucleic acid sequence that differs from the target sequence by 1-4 nucleotides. For example, a short interfering nucleic acid may comprise a sense strand that differs from a target sequence by one, two, three or four nucleotides, as long as RNAi-mediated degradation of the target mRNA is induced by the short interfering nucleic acid.

As used herein, "target mRNA" or "target sequence" means human $Na_v1.8$ mRNA, mutant or alternative splice forms of $Na_v1.8$ mRNA, or mRNA from cognate $Na_v1.8$ genes. The term "mutant", as used herein, means a short interfering nucleic acid that differs from the target mRNA by having a nucleotide insertion, nucleotide deletion, nucleotide substitution or nucleotide modification. Such alterations can include, for example, the: addition of non-nucleotide material, such as to the end(s) of the short interfering nucleic acids or to one or more internal nucleotides of the short interfering nucleic acids; modifications that make the short interfering nucleic acids resistant to nuclease digestion; or substitution of one or more nucleotides in the short interfering nucleic acids with deoxyribonucleotides. The term "cognate", as used herein, means a nucleic acid from another mammalian species. It is understood that human $Na_v1.8$ mRNA may contain target sequences in common with their respective cognates or mutants. A single short interfering nucleic acid comprising such a common targeting sequence can therefore induce RNAi-mediated degradation of different RNA types that contain the common targeting sequence.

The short interfering nucleic acid of the invention can be targeted to any stretch of approximately 19-25 contiguous nucleotides in any target mRNA sequence. Techniques for selecting target sequences for short interfering nucleic acids are known in the art. In addition, a target sequence on the target mRNA can be selected from a given cDNA sequence corresponding to the target mRNA, preferably beginning 50 to 100 nucleotides downstream, i.e., in the 3' direction, from the start codon. The target sequence can, however, be located in the 5' or 3' untranslated regions, or in the region nearby the start codon. Suitable target sequences in the $Na_v1.8$ cDNA sequence are given in Example 1.

The short interfering nucleic acid of the invention can comprise partially purified nucleic acid, substantially pure nucleic acid, synthetic nucleic acid or recombinantly produced nucleic acid. The term "substantially pure" is defined herein to mean a short interfering nucleic acid that is free from other contaminating proteins, nucleic acids, and other biologicals derived from an original source organism or recombinant DNA expression system. Purity may be assayed by standard methods and will typically exceed at least about 50%, preferably at least about 75%, more preferably at least about 90%, and most preferably at least about 95% purity. The purity evaluation may be made on a mass or molar basis.

The short interfering nucleic acids of the invention can be obtained using any one of a number of techniques known to those of skill in the art. In addition, the short interfering nucleic acids may also be synthesized as two separate, complementary nucleic acid molecules, or as a single nucleic acid molecule with two complementary regions. For example, the short interfering nucleic acids of the invention are chemically synthesized using appropriately protected ribonucleoside phosphoramidites and a conventional DNA/RNA synthesizer or other well known methods. In addition, the short interfering nucleic acids may be produced by a commercial supplier, such as Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, short interfering nucleic acids may also be expressed from a recombinant expression vector, such as a circular or linear DNA plasmid, using any suitable promoter. Recombinant expression vectors are typically self-replicating DNA or RNA constructs comprising nucleic acids encoding one of the short interfering nucleic acids, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, a translation initiation site, a polyadenylation site, sequences that terminate transcription and translation. Expression vectors may also contain an origin of replication that allows the vector to replicate independently of the host cell, or a selection gene, such as a gene conferring resistance to an antibiotic.

Vectors that could be used in this invention include microbial plasmids, viruses, bacteriophage, integratable DNA fragments, and other vehicles that may facilitate integration of the nucleic acids into the genome of the host.

Plasmids are a commonly used form of vector, but all other forms of vectors that serve an equivalent function and which are, or become, known in the art are suitable for use herein. See, e.g., Pouwels et al., *Cloning Vectors: A Laboratory Manual,* 1985 and Supplements, Elsevier, N.Y., and Rodriguez et al. (eds.), *Vectors: A Survey of Molecular Cloning Vectors and Their Uses,* 1988, Buttersworth, Boston, Mass.

Suitable promoters for expressing short interfering nucleic acids of the invention from a plasmid include, for example, the U6 promoter, the H1 RNA pol III promoter, and the cytomegalovirus promoter. Selection of other suitable promoters is within the skill in the art. The recombinant plasmids of the invention may also comprise an inducible or regulatable promoter for expression of the short interfering nucleic acid in a particular tissue or in a particular intracellular environment.

The short interfering nucleic acid expressed from recombinant plasmids may either be isolated from cultured cell expression systems by standard techniques, or can be expressed intracellularly. The short interfering nucleic acid of the invention can be expressed from a recombinant plasmid either as two separate, complementary RNA molecules, or as a single RNA molecule with two complementary regions. Selection of plasmids suitable for expressing short interfering nucleic acids of the invention, methods for inserting nucleic acid sequences for expressing the short interfering nucleic acids into the plasmid, and methods of delivering the recombinant plasmid to the cells of interest are within the skill in the art. See, for example, Tuschl, *Nat. Biotechnol,* vol. 20, pp. 446-448 (2002); Brummelkamp et al., *Science,* vol. 296, pp. 550-553 (2002); Miyagishi et al., *Nat. Biotechnol.,* vol. 20, ppl. 497-500 (2002); Paddison et al., *Genes Dev., vol.* 16, pp. 948-958 (2002); Lee et al., *Nat. Biotechnol., vol.* 20, pp. 500-505 (2002); Paul et al., *Nat. Biotechnol.,* vol. 20, pp. 505-508 (2002); and Sui et al., Proc. Natl. Acad. Sci. vol 99, 2002, pp 5515-5520).

By way of example, a plasmid may comprise a sense RNA strand coding sequence in operable connection with a polyT termination sequence under the control of a human U6 RNA promoter, and an antisense RNA strand coding sequence in operable connection with a polyT termination sequence under the control of a human U6 RNA promoter.

As used herein, "in operable connection with" means that the nucleic acid sequences encoding the sense or antisense strands are adjacent to another sequence. Preferably, the sequence encoding the sense or antisense strands are immediately adjacent to the poly T termination signal in the 5' direction. Therefore, during transcription of the sense or antisense sequences from the plasmid, the polyT termination signals act to terminate transcription.

As used herein, "under the control of a promoter" means that the nucleic acid sequences encoding the sense or antisense strands are located 3' of the promoter, so that the promoter can initiate transcription of the sense or antisense coding sequences.

Expression of the short interfering nucleic acids can be carried out by conventional methods in either prokaryotic or eukaryotic cells. Prokaryotes include both gram negative and positive organisms, e.g., *E. coli* and *B. subtilis.* Higher eukaryotes include established tissue culture cell lines from animal cells, both of non-mammalian origin, e.g., insect cells, and birds, and of mammalian origin, e.g., human, primates, and rodents. Many suitable host cells are known in the art. Preferred host cells are HEK293 cells and the neuroblastoma/DRG cell line ND7/23.

The short interfering nucleic acids of the invention may also be expressed from recombinant viral vectors. The recombinant viral vectors of the invention comprise sequences encoding the short interfering nucleic acids of the invention and any suitable promoter for expressing the short interfering nucleic acid sequences. Suitable promoters for expressing short interfering nucleic acids from a viral vector include, for example, the U6 promoter, the H1 RNA pol III promoter, and the cytomegalovirus promoter. Selection of other suitable promoters is within the skill in the art. The recombinant viral vectors of the invention can also comprise inducible or regulatable promoters for expression of the short interfering nucleic acids in a particular tissue or in a particular intracellular environment. The use of recombinant viral vectors to deliver short interfering nucleic acids of the invention to cells in vivo is discussed in more detail in Example 5.

The short interfering nucleic acids of the invention can be expressed from a recombinant viral vector either as two separate, complementary nucleic acid molecules, or as a single nucleic acid molecule with two complementary regions.

Any viral vector capable of accepting the coding sequences for the short interfering nucleic acid molecule(s) to be expressed can be used, such as, vectors derived from adenovirus (AV), adeno-associated virus (AAV), retroviruses, herpes virus, and the like. In addition, the tropism of the viral vectors may also be modified by pseudotyping the vectors with envelope proteins or other surface antigens from other viruses.

Selection of recombinant viral vectors suitable for use in the invention, methods for inserting nucleic acid sequences for expressing the short interfering nucleic acids into the vector, and methods of delivering the viral vector to the cells of interest are within the skill in the art. See, for example, Dornberg, *Gene Therap., vol.* 2, pp. 301-310 (1995); Eglitis, Biotechniques, vol. 6, pp. 608-614 (1988); Miller, *Hum Gene Therap.*, vol. 1, pp. 5-14 (1990); and Anderson, *Nature*, vol. 392, pp. 25-30 (1998).

Preferred viral vectors are those derived from adenovirus and adeno-associated virus. In a particularly preferred embodiment, a short interfering nucleic acid of the invention is expressed as a single-stranded nucleic acid molecule from a recombinant adenoviral vector comprising the U6 promoter. Preferred viral vectors are also herpes viral vectors. See for e.g., Burton, E. A. et al., (2005) *Curr. Opin. Ther.* August: 7(4):326-36 and Yeomans D. D. et al. (2005)—*Hum Gene Therap* February:16(2):271-7. By way of example, and not limitation, the expressed single stranded nucleic acid molecule can comprise two complementary regions connected by a single stranded hairpin area. The single stranded nucleic acid molecule can further comprise a 3' overhang.

In Vitro and In Vivo Methods

The ability of a short interfering nucleic acid to cause RNAi-mediated degradation of the target mRNA can be evaluated using standard techniques for measuring the levels of RNA or protein in cells. For example, short interfering nucleic acids may be delivered to cultured cells, and the levels of target mRNA can be measured by Northern blot, dot-blotting techniques, or by quantitative RT-PCR. Alternatively, the levels of $Na_v1.8$ protein in the cultured cells can be measured by ELISA or Western blot. A suitable cell culture system for measuring the effect of the present short interfering nucleic acids on target mRNA or protein levels is described in Example 2 below.

As discussed above, the short interfering nucleic acids of the invention targets and causes the RNAi-mediated degradation of $Na_v1.8$ mRNA, or alternative splice forms, mutants or cognates thereof. Degradation of the target mRNA by the present short interfering nucleic acids reduces the production of a functional gene product from the $Na_v1.8$ gene. Thus, the invention provides a method of inhibiting expression of $Na_v1.8$ in a subject, a method for inhibiting translation of an mRNA, a method for inhibiting expression of a polypeptide, a method for blocking the $Na_v1.8$ derived membrane potential in a cell, and a method for blocking the $Na_v1.8$ derived sodium current in a cell. In the methods of the invention, blocking includes, but is not limited to an abolition or reduction in the $Na_v1.8$ derived membrane potential or the $Na_v1.8$ derived sodium current Although these methods are more thoroughly detailed in the Examples, they all share a few common characterisitics.

A step of each of the above methods involves contacting a cell with a short interfering nucleic acid. In vivo, the contacting step involves administering a short interfering nucleic acid in a pharmaceutical composition to a subject. In vitro, the contacting step involves bringing the cell and short interfering nucleic acid into close physical proximity such that the cell and the short interfering nucleic acid may contact each other. This contacting step will allow the short interfering nucleic acid to enter the cell and cause RNAi-induced degradation of mRNA from the $Na_v1.8$ sodium channel gene.

Preferably, the contacting step utilizes the short interfering nucleic acids of SEQ ID NOs: 1-11. The short interfering nucleic acids of SEQ ID NOs: 1, 2, 3, 5, 10 and 11 are preferable. The short interfering nucleic acids of SEQ ID NOs: 2 and 5 are more preferable. The short interfering nucleic acids of SEQ ID NOs: 1 and 3 are the most preferable. One or more of the short interfering nucleic acids of SEQ ID NOs: 1, 2, 3, 4, 5, 6, 7, 8, 9, 10, and 11 can also be utilized in the methods of the invention. By way of example, and not limitation, one or more of the short interfering nucleic acids of SEQ ID NOs; 1, 2, 3, 5, 10 and 11 can be used in the methods of the invention. Furthermore, in the practice of the present methods, it is understood that more than one short interfering nucleic acids of the invention can be administered simultaneously or sequentially to a cell or to a subject. This invention further provides the short interfering nucleic acids of the invention complexed with one or more proteins and/or target nucleic acid and a cell comprising one or more short interfering nucleic acids of the invention.

Pharmaceutical Compositions

The short interfering nucleic acids and siRNAs of the present invention can be used therapeutically to treat chronic pain. Various compounds of the present invention may be incorporated into pharmaceutical compositions. For example, a pharmaceutical composition may comprise a single-stranded short interfering nucleic acid, a single-stranded short interfering nucleic acid that has a 3' overhang, a double-stranded short interfering nucleic acid, or a double-stranded short interfering nucleic acid wherein each strand has a 3' overhang. Preferably, the pharmaceutical composition comprises the short interfering nucleic acids of SEQ ID NOs: 1-11. The short interfering nucleic acids of SEQ ID NOs: 2 and 5 are more preferable, while the short interfering nucleic acids of SEQ ID NOs: 1 and 3 are the most preferable. One or more of the short interfering nucleic acids of SEQ ID NOs: 1, 2, 3, 4, 5, 6, 7, 8, 9, 10, and 11 can also be utilized in the pharmaceutical compositions of the invention. By way of example, and not limitation, one or more of the short interfering nucleic acids of SEQ ID NOs; 1, 2, 3, 5, 10 and 11 can be used in the pharmaceutical compositions of the invention.

Typical protocols for the therapeutic administration of such substances are well known in the art. Although the compositions of the present invention may be administered in simple solution, they are more typically administered in combination with other materials, such as carriers, preferably pharmaceutical acceptable carriers. The term "pharmaceutically acceptable carrier" means any compatible, non-toxic substance that is suitable for delivering the compositions of the invention to a subject. For example, sterile water, alcohol, fats, waxes, and inert solids may be included in a carrier. Pharmaceutically acceptable adjuvants, such as buffering agents and dispersing agents, may also be incorporated into the pharmaceutical composition. Generally, compositions useful for parenteral administration of such drugs are well known; e.g. *Remington's Pharmaceutical Science,* 17th Ed. (Mack Publishing Company, Easton, Pa., 1990).

Therapeutic formulations may be administered. Formulations typically comprise at least one active ingredient, together with one or more pharmaceutically acceptable carriers. Formulations may include those suitable for oral, rectal, nasal, transdermal, or parenteral (including subcutaneous, intramuscular, intravenous and intradermal) administration. The formulations may conveniently be presented in unit dosage form and may be prepared by any methods well known in the art of pharmacy. See, e.g., Gilman et al. (eds.) (1990), *The Pharmacological Bases of Therapeutics,* 8th Ed., Pergamon Press; and *Remington's Pharmaceutical Sciences,* supra, Easton, Pa.; Avis et al. (eds.) (1993) *Pharmaceutical Dosage Forms: Parenteral Medications* Dekker, New York; Lieberman et al. (eds.) (1990) *Pharmaceutical Dosage Forms: Tablets* Dekker, New York; and Lieberman et al. (eds.) (1990), *Pharmaceutical Dosage Forms: Disperse Systems* Dekker, New York.

By way of example, any of the short interfering nucleic acids or vectors of the invention may be deliverable transdermally. The transdermal compositions may take the form of creams, lotions, aerosols and/or emulsions and can be included in a transdermal patch of the matrix or reservoir type as are conventional in the art for this purpose. See, e.g. *Remington's Pharmaceutical Science,* 17th Ed. (Mack Publishing Company, Easton, Pa., 1990).

The dosage regimen involved in a therapeutic application will be determined by the attending physician, considering various factors that may modify the action of the therapeutic substance, e.g., the condition, body weight, sex and diet of the patient, the severity of any infection, time of administration, and other clinical factors. Often, treatment dosages are titrated upward from a low level to optimize safety and efficacy. Generally, daily dosages will fall within a range of 100-500 μg per kilogram of body weight. Typically, the dosage range will be 150-250 μg per kilogram of body weight. Preferably, the dosage will be 200 μg per kilogram of body weight. Dosages may be adjusted to account for the smaller molecular sizes and possibly decreased half-lives (clearance times) following administration. An "effective amount" of a composition of the invention is an amount that will ameliorate chronic pain in a subject.

Chronic pain may include one or more of the following characteristics: pain present for about three or more months, pain that is not fully relieved by routine medical management or pain that continues beyond a normal recovery period. Examples of chronic pain include, but are not limited to, chronic neuropathic pain and chronic inflammatory pain. Examples of chronic neuropathic and/or chronic inflammatory conditions, include, but are not limited to, post-herpetic neuralgia, painful diabetic neuropathy, radiculopathy, nerve compression injuries (e.g., carpal tunnel syndrome, trigeminal neuralgia, tumor-related nerve compressions), upper and low back pain (e.g., arising from disc herniation injuries, ankylosing spondylitis or cases of unknown pathology), complex regional pain syndromes types I and II, nerve trauma pain (e.g., phantom-limb pain, other painful conditions resulting from limb amputation), nerve-root avulsion injuries, HIV-associated pain, neuropathies arising from chemotherapeutic strategies, retinopathies, sciatica, hyperalgesia, hyperpathia and ongoing burning pain (e.g., wound-associated pain, including, but not limited to post-operative pain), joint pain, rheumatoid and osteoarthritis pain, fibromyalgia, burn pain, neuritis, sciatica, tendonitis, bone pain, migraine pain, urinogenital pain and neuropathic conditions attributed to bladder hyperreflexia.

EXAMPLES

The present invention may be better understood by reference to the following non-limiting examples, which are provided as exemplary of the invention. The following examples are presented in order to more fully illustrate the invention, and should in no way be construed as limiting the broad scope of the invention. Unless otherwise indicated, percentages given below for solids in solid mixtures, liquids in liquids, and solids in liquids are on a wt/wt, vol/vol and wt/vol basis, respectively. Sterile conditions were generally maintained during cell culture.

Materials and General Methods

Standard molecular biological methods were used, as described, e.g., in Maniatis et al., *Molecular Cloning: A Laboratory Manual,* 1982, Cold Spring Harbor Laboratory, Cold Spring Harbor Press; Sambrook et al., *Molecular Cloning: A Laboratory Manual,* (2d ed.), Vols 1-3, 1989, Cold Spring Harbor Press, NY; Ausubel et al., *Biology,* Greene Publishing Associates, Brooklyn, N.Y.; or Ausubel, et al. (1987 and Supplements), *Current Protocols in Molecular Biology,* Greene/Wiley, New York; and Innis et al. (eds.) *PCR Protocols: A Guide to Methods and Applications,* 1990, Academic Press, N.Y.

Example 1

This example illustrates the design of siRNAs against $Na_v1.8$. Putative siRNA sequences against both rat and human $Na_v1.8$ coding sequences were identified using Tuschl's prediction rules. See Tuschl et al., "Targeted mRNA degradation by double-stranded RNA in vitro", *Genes Dev.,* vol. 13, no. 24, pp. 3191-3197 (Dec. 15, 1999); and Elbashir et al., "Duplexes of 21-nucleotide RNAs mediate RNA interference in cultured mammalian cells", *Nature,* vol. 411, pp. 494-498 (2001). Table 2 identifies putative siRNA sequences against the human $Na_v1.8$ coding sequence. Also shown are the target sequences, the position of each target sequence in the gene, and the percentage of guanine/cytosine in the target sequence. Table 3 identifies putative siRNA sequences against the rat $Na_v1.8$ coding sequence. Also shown are the target sequences and the position of each target sequence in the gene.

TABLE 2

Human PN3 siRNAs

| Target | Target sequence | | position in gene | % GC |
|---|---|---|---|---|
| 1 | AATTCCCCATTGGATCCCTCG | (SEQ ID NO: 12) | 5 | 52.4 |
| 2 | AAACTAACAACTTCCGTCGCT | (SEQ ID NO: 13) | 26 | 42.9 |
| 3 | AACAACTTCCGTCGCTTTACT | (SEQ ID NO: 14) | 31 | 42.9 |
| 4 | AACTTCCGTCGCTTTACTCCG | (SEQ ID NO: 15) | 34 | 52.4 |
| 5 | AAGCAAATTGCTGCCAAGCAG | (SEQ ID NO: 16) | 76 | 47.6 |
| 6 | AAATTGCTGCCAAGCAGGGAA | (SEQ ID NO: 17) | 80 | 47.6 |
| 7 | AAGCAGGGAACAAAGAAAGCC | (SEQ ID NO: 18) | 91 | 47.6 |
| 8 | AACAAAGAAAGCCAGAGAGAA | (SEQ ID NO: 19) | 99 | 38.1 |
| 9 | AAAGAAAGCCAGAGAGAAGCA | (SEQ ID NO: 20) | 102 | 42.9 |
| 10 | AAAGCCAGAGAGAAGCATAGG | (SEQ ID NO: 21) | 106 | 47.6 |

TABLE 2-continued

Human PN3 siRNAs

| Target | Target sequence | position in gene | % GC |
|---|---|---|---|
| 11 | AAGCATAGGGAGCAGAAGGAC (SEQ ID NO: 22) | 118 | 52.4 |
| 12 | AAGGACCAAGAAGAGAAGCCT (SEQ ID NO: 23) | 133 | 47.6 |
| 13 | AAGAAGAGAAGCCTCGGCCCC (SEQ ID NO: 24) | 140 | 61.9 |
| 14 | AAGAGAAGCCTCGGCCCCAGC (SEQ ID NO: 25) | 143 | 66.7 |
| 15 | AAGCCTCGGCCCCAGCTGGAC (SEQ ID NO: 26) | 148 | 71.4 |
| 16 | AAAGCCTGCAACCAGCTGCCC (SEQ ID NO: 27) | 172 | 61.9 |
| 17 | AACCAGCTGCCCAAGTTCTAT (SEQ ID NO: 28) | 181 | 47.6 |
| 18 | AAGTTCTATGGTGAGCTCCCA (SEQ ID NO: 29) | 193 | 47.6 |
| 19 | AACTGATCGGGGAGCCCCTGG (SEQ ID NO: 30) | 218 | 66.7 |
| 20 | AACAAAGGGAGGACCATTTCC (SEQ ID NO: 31) | 286 | 47.6 |
| 21 | AAAGGGAGGACCATTTCCCGG (SEQ ID NO: 32) | 289 | 57.1 |
| 22 | AACCTGATCAGAAGAACGGCC (SEQ ID NO: 33) | 349 | 52.4 |
| 23 | AAGAACGGCCATCAAAGTGTC (SEQ ID NO: 34) | 360 | 47.6 |
| 24 | AACGGCCATCAAAGTGTCTGT (SEQ ID NO: 35) | 363 | 47.6 |
| 25 | AAAGTGTCTGTCCACTCGTGG (SEQ ID NO: 36) | 373 | 52.4 |
| 26 | AATTGTGTGTGCATGACCCGA (SEQ ID NO: 37) | 427 | 47.6 |
| 27 | AACTGACCTTCCAGAGAAAAT (SEQ ID NO: 38) | 447 | 38.1 |
| 28 | AAAATTGAATATGTCTTCACT (SEQ ID NO: 39) | 463 | 23.8 |
| 29 | AATTGAATATGTCTTCACTGT (SEQ ID NO: 40) | 465 | 28.6 |
| 30 | AATATGTCTTCACTGTCATTT (SEQ ID NO: 41) | 470 | 28.6 |
| 31 | AAGCCTTGATAAAGATACTGG (SEQ ID NO: 42) | 500 | 38.1 |
| 32 | AAAGATACTGGCAAGAGGATT (SEQ ID NO: 43) | 510 | 38.1 |
| 33 | AAGAGGATTTTGTCTAAATGA (SEQ ID NO: 44) | 522 | 28.6 |
| 34 | AAATGAGTTCACGTACCTGAG (SEQ ID NO: 45) | 537 | 42.9 |
| 35 | AACTGGCTGGATTTTAGCGTC (SEQ ID NO: 46) | 568 | 47.6 |
| 36 | AATAGATCTCCGTGGGATCTC (SEQ ID NO: 47) | 615 | 47.6 |
| 37 | AAAAACAGTTTCTGTGATCCC (SEQ ID NO: 48) | 669 | 38.1 |
| 38 | AAACAGTTTCTGTGATCCCAG (SEQ ID NO: 49) | 671 | 42.9 |
| 39 | AAGGTCATTGTGGGGCCCTG (SEQ ID NO: 50) | 697 | 61.9 |
| 40 | AAGAAACTGGCTGATGTGACC (SEQ ID NO: 51) | 730 | 47.6 |
| 41 | AAACTGGCTGATGTGACCATC (SEQ ID NO: 52) | 733 | 47.6 |
| 42 | AAGTGTTTTTGCCTTGGTGGG (SEQ ID NO: 53) | 771 | 47.6 |
| 43 | AACTCTTCAAGGGCAACCTCA (SEQ ID NO: 54) | 797 | 47.6 |
| 44 | AAGGGCAACCTCAAAAATAAA (SEQ ID NO: 55) | 805 | 33.3 |
| 45 | AACCTCAAAAATAAATGTGTC (SEQ ID NO: 56) | 811 | 28.6 |
| 46 | AAAAATAAATGTGTCAAGAAT (SEQ ID NO: 57) | 817 | 19 |
| 47 | AAATAAATGTGTCAAGAATGA (SEQ ID NO: 58) | 819 | 23.8 |
| 48 | AAATGTGTCAAGAATGACATG (SEQ ID NO: 59) | 823 | 33.3 |

TABLE 2-continued

Human PN3 siRNAs

| Target | Target sequence | position in gene | % GC |
|---|---|---|---|
| 49 | AAGAATGACATGGCTGTCAAT (SEQ ID NO: 60) | 832 | 38.1 |
| 50 | AATGACATGGCTGTCAATGAG (SEQ ID NO: 61) | 835 | 42.9 |
| 51 | AATGAGACAACCAACTACTCA (SEQ ID NO: 62) | 850 | 38.1 |
| 52 | AACCAACTACTCATCTCACAG (SEQ ID NO: 63) | 858 | 42.9 |
| 53 | AACTACTCATCTCACAGAAAA (SEQ ID NO: 64) | 862 | 33.3 |
| 54 | AAAACCAGATATCTACATAAA (SEQ ID NO: 65) | 879 | 23.8 |
| 55 | AACCAGATATCTACATAAATA (SEQ ID NO: 66) | 881 | 23.8 |
| 56 | AAATAAGCGAGGCACTTCTGA (SEQ ID NO: 67) | 897 | 42.9 |
| 57 | AAGCGAGGCACTTCTGACCCC (SEQ ID NO: 68) | 901 | 61.9 |
| 58 | AATGGATCTGACTCAGGCCAC (SEQ ID NO: 69) | 934 | 52.4 |
| 59 | AAAACTTCTGACAACCCGGAT (SEQ ID NO: 70) | 979 | 42.9 |
| 60 | AACTTCTGACAACCCGGATTT (SEQ ID NO: 71) | 981 | 42.9 |
| 61 | AACCCGGATTTTAACTACACC (SEQ ID NO: 72) | 991 | 42.9 |
| 62 | AACTACACCAGCTTTGATTCC (SEQ ID NO: 73) | 1003 | 42.9 |
| 63 | AACGCCTCTACCAGCAGACCC (SEQ ID NO: 74) | 1076 | 61.9 |
| 64 | AAAATCTATATGATCTTTTTT (SEQ ID NO: 75) | 1111 | 14.3 |
| 65 | AATCTATATGATCTTTTTTGT (SEQ ID NO: 76) | 1113 | 19 |
| 66 | AATCTTCCTGGGATCTTTCTA (SEQ ID NO: 77) | 1140 | 38.1 |
| 67 | AACTTGATCTTGGCTGTAGTC (SEQ ID NO: 78) | 1168 | 42.9 |
| 68 | AACCAGGCAACCACTGATGAA (SEQ ID NO: 79) | 1210 | 47.6 |
| 69 | AACCACTGATGAAATTGAAGC (SEQ ID NO: 80) | 1218 | 38.1 |
| 70 | AAATTGAAGCAAAGGAGAAGA (SEQ ID NO: 81) | 1229 | 33.3 |
| 71 | AAGCAAAGGAGAAGAAGTTCC (SEQ ID NO: 82) | 1235 | 42.9 |
| 72 | AAAGGAGAAGAAGTTCCAGGA (SEQ ID NO: 83) | 1239 | 42.9 |
| 73 | AAGAAGTTCCAGGAGGCCCTC (SEQ ID NO: 84) | 1246 | 57.1 |
| 74 | AAGTTCCAGGAGGCCCTCGAG (SEQ ID NO: 85) | 1249 | 61.9 |
| 75 | AAGGAGCAGGAGGTGCTAGCA (SEQ ID NO: 86) | 1279 | 57.1 |
| 76 | AACCTCTCTCCACTCCCACAA (SEQ ID NO: 87) | 1317 | 52.4 |
| 77 | AATGGATCACCTTTAACCTCC (SEQ ID NO: 88) | 1336 | 42.9 |
| 78 | AACCTCCAAAAATGCCAGTGA (SEQ ID NO: 89) | 1350 | 42.9 |
| 79 | AAAAATGCCAGTGAGAGAAGG (SEQ ID NO: 90) | 1357 | 42.9 |
| 80 | AAATGCCAGTGAGAGAAGGCA (SEQ ID NO: 91) | 1359 | 47.6 |
| 81 | AAGGCATAGAATAAAGCCAAG (SEQ ID NO: 92) | 1374 | 38.1 |
| 82 | AATAAAGCCAAGAGTGTCAGA (SEQ ID NO: 93) | 1383 | 38.1 |
| 83 | AAAGCCAAGAGTGTCAGAGGG (SEQ ID NO: 94) | 1386 | 52.4 |
| 84 | AAGAGTGTCAGAGGGCTCCAC (SEQ ID NO: 95) | 1392 | 57.1 |
| 85 | AAGACAACAAATCACCCCGCT (SEQ ID NO: 96) | 1415 | 47.6 |
| 86 | AACAAATCACCCCGCTCTGAT (SEQ ID NO: 97) | 1420 | 47.6 |

TABLE 2-continued

Human PN3 siRNAs

| Target | Target sequence | position in gene | % GC |
|---|---|---|---|
| 87 | AAATCACCCCGCTCTGATCCT (SEQ ID NO: 98) | 1423 | 52.4 |
| 88 | AACCAGCGCAGGATGTCTTTT (SEQ ID NO: 99) | 1447 | 47.6 |
| 89 | AAAACGCCGGGCTAGTCATGG (SEQ ID NO: 100) | 1485 | 57.1 |
| 90 | AACGCCGGGCTAGTCATGGCA (SEQ ID NO: 101) | 1487 | 61.9 |
| 91 | AAAGCCATCGGGGCTCTCTGC (SEQ ID NO: 102) | 1592 | 61.9 |
| 92 | AAGGCCCCCTCCCTAGAAGCC (SEQ ID NO: 103) | 1637 | 66.7 |
| 93 | AAGCCCTCTTCCTCAACCCAG (SEQ ID NO: 104) | 1653 | 57.1 |
| 94 | AACCCAGCAACCCTGACTCCA (SEQ ID NO: 105) | 1667 | 57.1 |
| 95 | AACCCTGACTCCAGGCATGGA (SEQ ID NO: 106) | 1675 | 57.1 |
| 96 | AAGATGAACACCAACCGCCGC (SEQ ID NO: 107) | 1697 | 57.1 |
| 97 | AACACCAACCGCCGCCCACTA (SEQ ID NO: 108) | 1703 | 61.9 |
| 98 | AACCGCCGCCCACTAGTGAGC (SEQ ID NO: 109) | 1709 | 66.7 |
| 99 | AAAAGAAGACTTTCTTGTCAG (SEQ ID NO: 110) | 1772 | 33.3 |
| 100 | AAGAAGACTTTCTTGTCAGCA (SEQ ID NO: 111) | 1774 | 38.1 |
| 101 | AAGACTTTCTTGTCAGCAGAA (SEQ ID NO: 112) | 1777 | 38.1 |
| 102 | AATACTTAGATGAACCTTTCC (SEQ ID NO: 113) | 1796 | 33.3 |
| 103 | AACCTTTCCGGGCCCAAAGGG (SEQ ID NO: 114) | 1808 | 61.9 |
| 104 | AAAGGGCAATGAGTGTTGTCA (SEQ ID NO: 115) | 1823 | 42.9 |
| 105 | AATGAGTGTTGTCAGTATCAT (SEQ ID NO: 116) | 1830 | 33.3 |
| 106 | AACCTCCGTCCTTGAGGAACT (SEQ ID NO: 117) | 1851 | 52.4 |
| 107 | AACTCGAGGAGTCTGAACAGA (SEQ ID NO: 118) | 1868 | 47.6 |
| 108 | AACAGAAGTGCCCACCCTGCT (SEQ ID NO: 119) | 1883 | 57.1 |
| 109 | AAGTGCCCACCCTGCTTGACC (SEQ ID NO: 120) | 1888 | 61.9 |
| 110 | AAGTATCTGATCTGGATTGC (SEQ ID NO: 121) | 1921 | 42.9 |
| 111 | AAGCTCAAGACAATTCTCTTT (SEQ ID NO: 122) | 1957 | 33.3 |
| 112 | AAGACAATTCTCTTTGGGCTT (SEQ ID NO: 123) | 1963 | 38.1 |
| 113 | AATTCTCTTTGGGCTTGTGAC (SEQ ID NO: 124) | 1968 | 42.9 |
| 114 | AACACCATCTTCATGGCCATG (SEQ ID NO: 125) | 2032 | 47.6 |
| 115 | AAGCCATGCTCCAGATAGGCA (SEQ ID NO: 126) | 2081 | 52.4 |
| 116 | AACATCGTCTTTACCATATTT (SEQ ID NO: 127) | 2101 | 28.6 |
| 117 | AAATGGTCTTCAAAATCATTG (SEQ ID NO: 128) | 2132 | 28.6 |
| 118 | AAAATCATTGCCTTCGACCCA (SEQ ID NO: 129) | 2143 | 42.9 |
| 119 | AATCATTGCCTTCGACCCATA (SEQ ID NO: 130) | 2145 | 42.9 |
| 120 | AAGAAGTGGAATATCTTTGAC (SEQ ID NO: 131) | 2179 | 33.3 |
| 121 | AAGTGGAATATCTTTGACTGC (SEQ ID NO: 132) | 2182 | 38.1 |
| 122 | AATATCTTGACTGCATCATC (SEQ ID NO: 133) | 2188 | 33.3 |
| 123 | AAGAAGGGAAGCCTGTCTGTG (SEQ ID NO: 134) | 2242 | 52.4 |
| 124 | AAGGGAAGCCTGTCTGTGCTG (SEQ ID NO: 135) | 2245 | 57.1 |

TABLE 2-continued

| | Human PN3 siRNAs | | |
|---|---|---|---|
| Target | Target sequence | position in gene | % GC |
| 125 | AAGCCTGTCTGTGCTGCGGAG (SEQ ID NO: 136) | 2250 | 61.9 |
| 126 | AAGCTGGCCAAATCCTGGCCC (SEQ ID NO: 137) | 2293 | 61.9 |
| 127 | AAATCCTGGCCCACCTTAAAC (SEQ ID NO: 138) | 2302 | 47.6 |
| 128 | AAACACACTCATCAAGATCAT (SEQ ID NO: 139) | 2319 | 33.3 |
| 129 | AAGATCATCGGAAACTCAGTG (SEQ ID NO: 140) | 2332 | 42.9 |
| 130 | AAACTCAGTGGGGGCACTGGG (SEQ ID NO: 141) | 2343 | 61.9 |
| 131 | AACCTCACCATCATCCTGGCC (SEQ ID NO: 142) | 2365 | 57.1 |
| 132 | AAGCAGCTCCTAGGGGAAAAC (SEQ ID NO: 143) | 2416 | 52.4 |
| 133 | AAAACTACCGTAACAACCGAA (SEQ ID NO: 144) | 2432 | 38.1 |
| 134 | AACTACCGTAACAACCGAAAA (SEQ ID NO: 145) | 2434 | 38.1 |
| 135 | AACAACCGAAAAAATATCTCC (SEQ ID NO: 146) | 2443 | 33.3 |
| 136 | AACCGAAAAAATATCTCCGCG (SEQ ID NO: 147) | 2446 | 42.9 |
| 137 | AAAAAATATCTCCGCGCCCCA (SEQ ID NO: 148) | 2451 | 47.6 |
| 138 | AAAATATCTCCGCGCCCCATG (SEQ ID NO: 149) | 2453 | 52.4 |
| 139 | AATATCTCCGCGCCCCATGAA (SEQ ID NO: 150) | 2455 | 52.4 |
| 140 | AAGACTGGCCCCGCTGGCACA (SEQ ID NO: 151) | 2474 | 66.7 |
| 141 | AACATGTGGGCCTGCATGGAA (SEQ ID NO: 152) | 2557 | 52.4 |
| 142 | AAGTTGGCCAAAAATCCATAT (SEQ ID NO: 153) | 2576 | 33.3 |
| 143 | AAAAATCCATATGCCTCATCC (SEQ ID NO: 154) | 2585 | 38.1 |
| 144 | AAATCCATATGCCTCATCCTT (SEQ ID NO: 155) | 2587 | 38.1 |
| 145 | AACCTGGTGGTGCTTAACCTG (SEQ ID NO: 156) | 2632 | 52.4 |
| 146 | AACCTGTTCATCGCCCTGCTA (SEQ ID NO: 157) | 2647 | 52.4 |
| 147 | AACTCTTTCAGTGCTGACAAC (SEQ ID NO: 158) | 2671 | 42.9 |
| 148 | AACCTCACAGCCCCGGAGGAC (SEQ ID NO: 159) | 2689 | 66.7 |
| 149 | AACAACCTGCAGGTGGCCCTG (SEQ ID NO: 160) | 2722 | 61.9 |
| 150 | AACCTGCAGGTGGCCCTGGCA (SEQ ID NO: 161) | 2725 | 66.7 |
| 151 | AAACAGGCTCTTTGCAGCTTC (SEQ ID NO: 162) | 2773 | 47.6 |
| 152 | AAGGCAGAGCCTGAGCTGGTG (SEQ ID NO: 163) | 2824 | 61.9 |
| 153 | AAACTCCCACTCTCCAGCTCC (SEQ ID NO: 164) | 2848 | 57.1 |
| 154 | AAGGCTGAGAACCACATTGCT (SEQ ID NO: 165) | 2869 | 47.6 |
| 155 | AACCACATTGCTGCCAACACT (SEQ ID NO: 166) | 2878 | 47.6 |
| 156 | AACACTGCCAGGGGGAGCTCT (SEQ ID NO: 167) | 2893 | 61.9 |
| 157 | AAGCTCCCAGAGGCCCCAGGG (SEQ ID NO: 168) | 2924 | 71.4 |
| 158 | AATCCGACTGTGTGGGTCTCT (SEQ ID NO: 169) | 2968 | 52.4 |
| 159 | AATCTGATCTTGATGACTTGG (SEQ ID NO: 170) | 3008 | 38.1 |
| 160 | AAGATGCTCAGAGCTTCCAGC (SEQ ID NO: 171) | 3044 | 52.4 |
| 161 | AAGTGATCCCCAAAGGACAGC (SEQ ID NO: 172) | 3068 | 52.4 |

TABLE 2-continued

Human PN3 siRNAs

| Target | Target sequence | position in gene | % GC |
|---|---|---|---|
| 162 | AAAGGACAGCAGGAGCAGCTG (SEQ ID NO: 173) | 3079 | 57.1 |
| 163 | AAGTCGAGAGGTGTGGGACC (SEQ ID NO: 174) | 3104 | 61.9 |
| 164 | AACATCTTCTGAGGACCTGGC (SEQ ID NO: 175) | 3153 | 52.4 |
| 165 | AAAGATGAGTCTGTTCCTCAG (SEQ ID NO: 176) | 3196 | 42.9 |
| 166 | AAGCTCCTCTGAGGGCAGCAC (SEQ ID NO: 177) | 3243 | 61.9 |
| 167 | AAATCCTGAGGAAGATCCCTG (SEQ ID NO: 178) | 3287 | 47.6 |
| 168 | AAGATCCCTGAGCTGGCAGAT (SEQ ID NO: 179) | 3298 | 52.4 |
| 169 | AAGAACCAGATGACTGCTTCA (SEQ ID NO: 180) | 3326 | 42.9 |
| 170 | AACCAGATGACTGCTTCACAG (SEQ ID NO: 181) | 3329 | 47.6 |
| 171 | AAGGATGCATTCGCCACTGTC (SEQ ID NO: 182) | 3350 | 52.4 |
| 172 | AAACTGGATACCACCAAGAGT (SEQ ID NO: 183) | 3379 | 42.9 |
| 173 | AAGAGTCCATGGGATGTGGGC (SEQ ID NO: 184) | 3394 | 57.1 |
| 174 | AAGACTTGCTACCGTATCGTG (SEQ ID NO: 185) | 3427 | 47.6 |
| 175 | AAGACTATTACCTGGACCAGA (SEQ ID NO: 186) | 3515 | 42.9 |
| 176 | AAGCCCACGGTGAAAGCTTTG (SEQ ID NO: 187) | 3535 | 52.4 |
| 177 | AAAGCTTTGCTGGAGTACACT (SEQ ID NO: 188) | 3547 | 42.9 |
| 178 | AAGTGGGTGGCCTATGGCTTC (SEQ ID NO: 189) | 3610 | 57.1 |
| 179 | AAAAAGTACTTCACCAATGCC (SEQ ID NO: 190) | 3631 | 38.1 |
| 180 | AAAGTACTTCACCAATGCCTG (SEQ ID NO: 191) | 3633 | 42.9 |
| 181 | AATGCCTGGTGCTGGCTGGAC (SEQ ID NO: 192) | 3646 | 61.9 |
| 182 | AATATCTCACTGATAAGTCTC (SEQ ID NO: 193) | 3679 | 33.3 |
| 183 | AAGTCTCACAGCGAAGATTCT (SEQ ID NO: 194) | 3693 | 42.9 |
| 184 | AAGATTCTGGAATATTCTGAA (SEQ ID NO: 195) | 3706 | 28.6 |
| 185 | AATATTCTGAAGTGGCTCCCA (SEQ ID NO: 196) | 3716 | 42.9 |
| 186 | AAGTGGCTCCCATCAAAGCCC (SEQ ID NO: 197) | 3725 | 57.1 |
| 187 | AAAGCCCTTCGAACCCTTCGC (SEQ ID NO: 198) | 3739 | 57.1 |
| 188 | AACCCTTCGCGCTCTGCGGCC (SEQ ID NO: 199) | 3750 | 71.4 |
| 189 | AAGGCATGCGGGTGGTGGTGG (SEQ ID NO: 200) | 3794 | 66.7 |
| 190 | AATGTCCTCCTCGTCTGCCTC (SEQ ID NO: 201) | 3847 | 57.1 |
| 191 | AACCTCTTCGCAGGGAAGTTT (SEQ ID NO: 202) | 3901 | 47.6 |
| 192 | AAGTTTTGGAGGTGCATCAAC (SEQ ID NO: 203) | 3916 | 42.9 |
| 193 | AACTATACCGATGGAGAGTTT (SEQ ID NO: 204) | 3934 | 38.1 |
| 194 | AATAACAAGTCTGACTGCAAG (SEQ ID NO: 205) | 3979 | 38.1 |
| 195 | AACAAGTCTGACTGCAAGATT (SEQ ID NO: 206) | 3982 | 38.1 |
| 196 | AAGTCTGACTGCAAGATTCAA (SEQ ID NO: 207) | 3985 | 38.1 |
| 197 | AAGATTCAAAACTCCACTGGC (SEQ ID NO: 208) | 3997 | 42.9 |
| 198 | AAAACTCCACTGGCAGCTTCT (SEQ ID NO: 209) | 4004 | 47.6 |
| 199 | AACTCCACTGGCAGCTTCTTC (SEQ ID NO: 210) | 4006 | 52.4 |

TABLE 2-continued

Human PN3 siRNAs

| Target | Target sequence | position in gene | % GC |
|---|---|---|---|
| 200 | AATGTGAAAGTCAACTTTGAT (SEQ ID NO: 211) | 4033 | 28.6 |
| 201 | AAAGTCAACTTTGATAATGTT (SEQ ID NO: 212) | 4039 | 23.8 |
| 202 | AACTTTGATAATGTTGCAATG (SEQ ID NO: 213) | 4045 | 28.6 |
| 203 | AATGTTGCAATGGGTTACCTT (SEQ ID NO: 214) | 4054 | 38.1 |
| 204 | AATGGGTTACCTTGCACTTCT (SEQ ID NO: 215) | 4062 | 42.9 |
| 205 | AACCTTTAAAGGCTGGATGGA (SEQ ID NO: 216) | 4092 | 42.9 |
| 206 | AAAGGCTGGATGGACATTATG (SEQ ID NO: 217) | 4099 | 42.9 |
| 207 | AACATGCAACCCAAGTGGGAG (SEQ ID NO: 218) | 4147 | 52.4 |
| 208 | AACCCAAGTGGGAGGACAACG (SEQ ID NO: 219) | 4154 | 57.1 |
| 209 | AAGTGGGAGGACAACGTGTAC (SEQ ID NO: 220) | 4159 | 52.4 |
| 210 | AACGTGTACATGTATTTGTAC (SEQ ID NO: 221) | 4171 | 33.3 |
| 211 | AATCTCTTTGTTGGGGTCATA (SEQ ID NO: 222) | 4231 | 38.1 |
| 212 | AATTGACAACTTCAATCAACA (SEQ ID NO: 223) | 4251 | 28.6 |
| 213 | AACTTCAATCAACAGAAAAAA (SEQ ID NO: 224) | 4258 | 23.8 |
| 214 | AATCAACAGAAAAAAAAGTTA (SEQ ID NO: 225) | 4264 | 19 |
| 215 | AACAGAAAAAAAAGTTAGGGG (SEQ ID NO: 226) | 4268 | 33.3 |
| 216 | AAAAAAAGTTAGGGGGCCAG (SEQ ID NO: 227) | 4273 | 42.9 |
| 217 | AAAAAAGTTAGGGGGCCAGGA (SEQ ID NO: 228) | 4275 | 47.6 |
| 218 | AAAAGTTAGGGGGCCAGGACA (SEQ ID NO: 229) | 4277 | 52.4 |
| 219 | AAGTTAGGGGGCCAGGACATC (SEQ ID NO: 230) | 4279 | 57.1 |
| 220 | AAGAAATACTACAATGCCATG (SEQ ID NO: 231) | 4318 | 33.3 |
| 221 | AAATACTACAATGCCATGAAG (SEQ ID NO: 232) | 4321 | 33.3 |
| 222 | AATGCCATGAAGAAGTTGGGC (SEQ ID NO: 233) | 4330 | 47.6 |
| 223 | AAGAAGTTGGGCTCCAAGAAG (SEQ ID NO: 234) | 4339 | 47.6 |
| 224 | AAGTTGGGCTCCAAGAAGCCC (SEQ ID NO: 235) | 4342 | 57.1 |
| 225 | AAGAAGCCCCAGAAGCCCATC (SEQ ID NO: 236) | 4354 | 57.1 |
| 226 | AAGCCCCAGAAGCCCATCCCA (SEQ ID NO: 237) | 4357 | 61.9 |
| 227 | AAGCCCATCCCACGGCCCCTG (SEQ ID NO: 238) | 4366 | 71.4 |
| 228 | AACAAGTTCCAGGGTTTTGTC (SEQ ID NO: 239) | 4387 | 42.9 |
| 229 | AAGTTCCAGGGTTTTGTCTTT (SEQ ID NO: 240) | 4390 | 38.1 |
| 230 | AAGCTTTTGACATCACCATCA (SEQ ID NO: 241) | 4427 | 38.1 |
| 231 | AACATGATCACCATGATGGTG (SEQ ID NO: 242) | 4465 | 42.9 |
| 232 | AAAGTGAAGAAAAGACGAAAA (SEQ ID NO: 243) | 4499 | 28.6 |
| 233 | AAGAAAAGACGAAAATTCTGG (SEQ ID NO: 244) | 4505 | 33.3 |
| 234 | AAAAGACGAAAATTCTGGGCA (SEQ ID NO: 245) | 4508 | 38.1 |
| 235 | AAGACGAAAATTCTGGGCAAA (SEQ ID NO: 246) | 4510 | 38.1 |
| 236 | AAAATTCTGGGCAAAATCAAC (SEQ ID NO: 247) | 4516 | 33.3 |
| 237 | AATTCTGGGCAAAATCAACCA (SEQ ID NO: 248) | 4518 | 38.1 |

TABLE 2-continued

Human PN3 siRNAs

| Target | Target sequence | position in gene | % GC |
|---|---|---|---|
| 238 | AAAATCAACCAGTTCTTTGTG (SEQ ID NO: 249) | 4528 | 33.3 |
| 239 | AATCAACCAGTTCTTTGTGGC (SEQ ID NO: 250) | 4530 | 42.9 |
| 240 | AACCAGTTCTTTGTGGCCGTC (SEQ ID NO: 251) | 4534 | 52.4 |
| 241 | AATGTGTCATGAAGATGTTCG (SEQ ID NO: 252) | 4565 | 38.1 |
| 242 | AAGATGTTCGCTTTGAGGCAG (SEQ ID NO: 253) | 4576 | 47.6 |
| 243 | AAATGGCTGGAATGTGTTTGA (SEQ ID NO: 254) | 4608 | 38.1 |
| 244 | AATGTGTTTGACTTCATTGTG (SEQ ID NO: 255) | 4618 | 33.3 |
| 245 | AATTCTTAAGTCACTTCAAAG (SEQ ID NO: 256) | 4674 | 28.6 |
| 246 | AAGTCACTTCAAAGTTACTTC (SEQ ID NO: 257) | 4681 | 33.3 |
| 247 | AAAGTTACTTCTCCCCAACGC (SEQ ID NO: 258) | 4691 | 47.6 |
| 248 | AACGCTCTTCAGAGTCATCCG (SEQ ID NO: 259) | 4707 | 52.4 |
| 249 | AATTGGCCGCATCCTCAGACT (SEQ ID NO: 260) | 4737 | 52.4 |
| 250 | AAGGGGATCCGCACACTGCTC (SEQ ID NO: 261) | 4771 | 61.9 |
| 251 | AACATCGGGCTGTTGCTATTC (SEQ ID NO: 262) | 4825 | 47.6 |
| 252 | AACTTCCAGACCTTCGCCAAC (SEQ ID NO: 263) | 4927 | 52.4 |
| 253 | AACAGCATGCTGTGCCTCTTC (SEQ ID NO: 264) | 4945 | 52.4 |
| 254 | AACACAGGGCCCCCCTACTGT (SEQ ID NO: 265) | 5014 | 61.9 |
| 255 | AATCTGCCCAACAGCAATGGC (SEQ ID NO: 266) | 5041 | 52.4 |
| 256 | AACAGCAATGGCACCAGAGGG (SEQ ID NO: 267) | 5050 | 57.1 |
| 257 | AATGGCACCAGAGGGGACTGT (SEQ ID NO: 268) | 5056 | 57.1 |
| 258 | AACATGTACATTGCAGTGATT (SEQ ID NO: 269) | 5143 | 33.3 |
| 259 | AACTTCAATGTGGCCACGGAG (SEQ ID NO: 270) | 5170 | 52.4 |
| 260 | AATGTGGCCACGGAGGAGAGC (SEQ ID NO: 271) | 5176 | 61.9 |
| 261 | AAGTTTGACCCAGAGGCCACT (SEQ ID NO: 272) | 5248 | 52.4 |
| 262 | AATCCCAAAACCCAATCGAAA (SEQ ID NO: 273) | 5328 | 38.1 |
| 263 | AAAACCCAATCGAAATATACT (SEQ ID NO: 274) | 5334 | 28.6 |
| 264 | AACCCAATCGAAATATACTGA (SEQ ID NO: 275) | 5336 | 33.3 |
| 265 | AATCGAAATATACTGATCCAG (SEQ ID NO: 276) | 5341 | 33.3 |
| 266 | AAATATACTGATCCAGATGGA (SEQ ID NO: 277) | 5346 | 33.3 |
| 267 | AAGATCCACTGCTTGGACATC (SEQ ID NO: 278) | 5389 | 47.6 |
| 268 | AAGAATGTCCTAGGAGAATCC (SEQ ID NO: 279) | 5425 | 42.9 |
| 269 | AATGTCCTAGGAGAATCCGGG (SEQ ID NO: 280) | 5428 | 52.4 |
| 270 | AATCCGGGGAGTTGGATTCTC (SEQ ID NO: 281) | 5441 | 52.4 |
| 271 | AAGGCAAATATGGAGGAGAAG (SEQ ID NO: 282) | 5464 | 42.9 |
| 272 | AAATATGGAGGAGAAGTTTAT (SEQ ID NO: 283) | 5469 | 28.6 |
| 273 | AAGTTTATGGCAACTAATCTT (SEQ ID NO: 284) | 5482 | 28.6 |
| 274 | AACTAATCTTTCAAAATCATC (SEQ ID NO: 285) | 5493 | 23.8 |
| 275 | AATCTTTCAAAATCATCCTAT (SEQ ID NO: 286) | 5497 | 23.8 |

TABLE 2-continued

Human PN3 siRNAs

| Target | Target sequence | position in gene | % GC |
|---|---|---|---|
| 276 | AAAATCATCCTATGAACCAAT (SEQ ID NO: 287) | 5505 | 28.6 |
| 277 | AATCATCCTATGAACCAATAG (SEQ ID NO: 288) | 5507 | 33.3 |
| 278 | AACCAATAGCAACCACTCTCC (SEQ ID NO: 289) | 5519 | 47.6 |
| 279 | AATAGCAACCACTCTCCGATG (SEQ ID NO: 290) | 5523 | 47.6 |
| 280 | AACCACTCTCCGATGGAAGCA (SEQ ID NO: 291) | 5529 | 52.4 |
| 281 | AAGCAAGAAGACATTTCAGCC (SEQ ID NO: 292) | 5545 | 42.9 |
| 282 | AAGAAGACATTTCAGCCACTG (SEQ ID NO: 293) | 5549 | 42.9 |
| 283 | AAGACATTTCAGCCACTGTCA (SEQ ID NO: 294) | 5552 | 42.9 |
| 284 | AAAAGGCCTATCGGAGCTATG (SEQ ID NO: 295) | 5576 | 47.6 |
| 285 | AAGGCCTATCGGAGCTATGTG (SEQ ID NO: 296) | 5578 | 52.4 |
| 286 | AACACCCATGTGTGCCCAGA (SEQ ID NO: 297) | 5623 | 57.1 |
| 287 | AAGGTTTTGTTGCATTCACAG (SEQ ID NO: 298) | 5675 | 38.1 |
| 288 | AAATGAAAATTGTGTACTCCC (SEQ ID NO: 299) | 5697 | 33.3 |
| 289 | AAAATTGTGTACTCCCAGACA (SEQ ID NO: 300) | 5702 | 38.1 |
| 290 | AATTGTGTACTCCCAGACAAA (SEQ ID NO: 301) | 5704 | 38.1 |
| 291 | AAATCTGAAACTGCTTCTGCC (SEQ ID NO: 302) | 5722 | 42.9 |
| 292 | AAACTGCTTCTGCCACATCAT (SEQ ID NO: 303) | 5729 | 42.9 |
| 293 | AACATGAGGACATCTAGCTCA (SEQ ID NO: 304) | 5797 | 42.9 |
| 294 | AATACAAAATGAAGATGAAGC (SEQ ID NO: 305) | 5817 | 28.6 |
| 295 | AAAATGAAGATGAAGCCACCA (SEQ ID NO: 306) | 5822 | 38.1 |
| 296 | AATGAAGATGAAGCCACCAGT (SEQ ID NO: 307) | 5824 | 42.9 |
| 297 | AAGATGAAGCCACCAGTATGG (SEQ ID NO: 308) | 5828 | 47.6 |
| 298 | AAGCCACCAGTATGGAGCTGA (SEQ ID NO: 309) | 5834 | 52.4 |

TABLE 3

Rat PN3 siRNA's

| Target | Target sequence | position in gene |
|---|---|---|
| 1 | AACTACCAATTTCAGACGGTT (SEQ ID NO: 310) | 27 |
| 2 | AATTTCAGACGGTTCACTCCA (SEQ ID NO: 311) | 34 |
| 3 | AAGCAGATTGCTGCTCACCGC (SEQ ID NO: 312) | 76 |
| 4 | AAGAAGGCCAGAACCAAGCAC (SEQ ID NO: 313) | 103 |
| 5 | AAGGCCAGAACCAAGCACAGA (SEQ ID NO: 314) | 106 |
| 6 | AACCAAGCACAGAGGACAGGA (SEQ ID NO: 315) | 114 |
| 7 | AAGCACAGAGGACAGGAGGAC (SEQ ID NO: 316) | 118 |
| 8 | AAGGGCGAGAAGCCCAGGCCT (SEQ ID NO: 317) | 139 |
| 9 | AAGCCCAGGCCTCAGCTGGAC (SEQ ID NO: 318) | 148 |
| 10 | AAAGCCTGTAACCAGCTGCCC (SEQ ID NO: 319) | 172 |
| 11 | AACCAGCTGCCCAAGTTCTAT (SEQ ID NO: 320) | 181 |
| 12 | AAGTTCTATGGTGAGCTCCCA (SEQ ID NO: 321) | 193 |
| 13 | AACTGGTCGGGGAGCCCCTGG (SEQ ID NO: 322) | 218 |
| 14 | AATAAAAGCAGGACCATTTCC (SEQ ID NO: 323) | 286 |
| 15 | AAAAGCAGGACCATTTCCAGA (SEQ ID NO: 324) | 289 |
| 16 | AAGCAGGACCATTTCCAGATT (SEQ ID NO: 325) | 291 |
| 17 | AACCTGATCAGAAGAACAGCC (SEQ ID NO: 326) | 349 |
| 18 | AAGAACAGCCATCAAAGTGTC (SEQ ID NO: 327) | 360 |

TABLE 3-continued

Rat PN3 siRNA's

| Target | Target sequence | position in gene |
|---|---|---|
| 19 | AACAGCCATCAAAGTGTCTGT (SEQ ID NO: 328) | 363 |
| 20 | AAAGTGTCTGTCCATTCCTGG (SEQ ID NO: 329) | 373 |
| 21 | AACTGCGTGTGCATGACCCGA (SEQ ID NO: 330) | 427 |
| 22 | AACTGATCTTCCAGAGAAAGT (SEQ ID NO: 331) | 447 |
| 23 | AAAGTCGAGTACGTCTTCACT (SEQ ID NO: 332) | 463 |
| 24 | AAGATACTGGCAAGAGGGTTT (SEQ ID NO: 333) | 511 |
| 25 | AAGAGGGTTTTGTCTAAATGA (SEQ ID NO: 334) | 522 |
| 26 | AAATGAGTTCACTTATCTTCG (SEQ ID NO: 335) | 537 |
| 27 | AACTGGCTGGACTTCAGTGTC (SEQ ID NO: 336) | 568 |
| 28 | AATCTCAGGCCTGCGGACATT (SEQ ID NO: 337) | 630 |
| 29 | AAAACTGTTTCTGTGATCCCA (SEQ ID NO: 338) | 670 |
| 30 | AACTGTTTCTGTGATCCCAGG (SEQ ID NO: 339) | 672 |
| 31 | AAGGTCATCGTGGGAGCCCTG (SEQ ID NO: 340) | 697 |
| 32 | AAGCTGGCCGACGTGACTATC (SEQ ID NO: 341) | 733 |
| 33 | AAGGGGAACCTTAAGAACAAA (SEQ ID NO: 342) | 805 |
| 34 | AACCTTAAGAACAAATGCATC (SEQ ID NO: 343) | 811 |
| 35 | AAGAACAAATGCATCAGGAAC (SEQ ID NO: 344) | 817 |
| 36 | AACAAATGCATCAGGAACGGA (SEQ ID NO: 345) | 820 |
| 37 | AAATGCATCAGGAACGGAACA (SEQ ID NO: 346) | 823 |
| 38 | AACGGAACAGATCCCCACAAG (SEQ ID NO: 347) | 835 |
| 39 | AACAGATCCCCACAAGGCTGA (SEQ ID NO: 348) | 840 |
| 40 | AAGGCTGACAACCTCTCATCT (SEQ ID NO: 349) | 853 |
| 41 | AACCTCTCATCTGAAATGGCA (SEQ ID NO: 350) | 862 |
| 42 | AAATGGCAGAATACATCTTCA (SEQ ID NO: 351) | 875 |
| 43 | AATACATCTTCATCAAGCCTG (SEQ ID NO: 352) | 884 |
| 44 | AAGCCTGGTACTACGGATCCC (SEQ ID NO: 353) | 898 |
| 45 | AATGGGTCTGATGCTGGTCAC (SEQ ID NO: 354) | 931 |
| 46 | AAAACTCCTGACAACCCGGAT (SEQ ID NO: 355) | 976 |
| 47 | AACTCCTGACAACCCGGATTT (SEQ ID NO: 356) | 978 |
| 48 | AACCCGGATTTTAACTACACC (SEQ ID NO: 357) | 988 |
| 49 | AACTACACCAGCTTTGATTCC (SEQ ID NO: 358) | 1000 |
| 50 | AAAATGTACATGGTCTTTTTC (SEQ ID NO: 359) | 1108 |
| 51 | AATGTACATGGTCTTTTTCGT (SEQ ID NO: 360) | 1110 |
| 52 | AATTTGATCTTGGCCGTGGTC (SEQ ID NO: 361) | 1165 |
| 53 | AAGAGCAGAGCCAGGCAACAA (SEQ ID NO: 362) | 1199 |
| 54 | AACAATTGCAGAAATCGAAGC (SEQ ID NO: 363) | 1215 |
| 55 | AATTGCAGAAATCGAAGCCAA (SEQ ID NO: 364) | 1218 |
| 56 | AAATCGAAGCCAAGGAAAAAA (SEQ ID NO: 365) | 1226 |
| 57 | AAGCCAAGGAAAAAAAGTTCC (SEQ ID NO: 366) | 1232 |
| 58 | AAGGAAAAAAAGTTCCAGGAA (SEQ ID NO: 367) | 1237 |
| 59 | AAAAAAAGTTCCAGGAAGCCC (SEQ ID NO: 368) | 1241 |
| 60 | AAAAAGTTCCAGGAAGCCCTT (SEQ ID NO: 369) | 1243 |
| 61 | AAAGTTCCAGGAAGCCCTTGA (SEQ ID NO: 370) | 1245 |
| 62 | AAGCCCTTGAGGTGCTGCAGA (SEQ ID NO: 371) | 1256 |
| 63 | AAGGAACAGGAGGTGCTGGCA (SEQ ID NO: 372) | 1276 |
| 64 | AACAGGAGGTGCTGGCAGCCC (SEQ ID NO: 373) | 1280 |
| 65 | AAAAACGCCAATGAGAGAAGA (SEQ ID NO: 374) | 1354 |
| 66 | AAACGCCAATGAGAGAAGACC (SEQ ID NO: 375) | 1356 |
| 67 | AATGAGAGAAGACCCAGGGTG (SEQ ID NO: 376) | 1363 |
| 68 | AAGACCCAGGGTGAAATCAAG (SEQ ID NO: 377) | 1371 |
| 69 | AAATCAAGGGTGTCAGAGGGC (SEQ ID NO: 378) | 1384 |
| 70 | AAGGGTGTCAGAGGGCTCCAC (SEQ ID NO: 379) | 1389 |
| 71 | AACAGGTCACCCCAATCTGAC (SEQ ID NO: 380) | 1417 |
| 72 | AATCTGACCCTTACAACCAGC (SEQ ID NO: 381) | 1430 |
| 73 | AACCAGCGCAGGATGTCTTTC (SEQ ID NO: 382) | 1444 |
| 74 | AAGACGCAGGGCTAGCCACGG (SEQ ID NO: 383) | 1482 |
| 75 | AAGACATCTCATTTCCTGACG (SEQ ID NO: 384) | 1532 |
| 76 | AAAGCCGTCGAGGTTCCATAT (SEQ ID NO: 385) | 1589 |
| 77 | AACCCTGGCCGTAGACATGGA (SEQ ID NO: 386) | 1672 |
| 78 | AAGAGGGACAGCTCGGAGTGC (SEQ ID NO: 387) | 1694 |
| 79 | AAGGCCCGGCACTCGACACTA (SEQ ID NO: 388) | 1745 |
| 80 | AAGAGCTTCCTGTCTGCGGGC (SEQ ID NO: 389) | 1774 |
| 81 | AACGAACCTTTCCGAGCACAG (SEQ ID NO: 390) | 1801 |
| 82 | AACCTTTCCGAGCACAGAGGG (SEQ ID NO: 391) | 1805 |
| 83 | AAGAGTCTAAGCTGAAGTGCC (SEQ ID NO: 392) | 1871 |
| 84 | AAGCTGAAGTGCCCACCCTGC (SEQ ID NO: 393) | 1879 |
| 85 | AAGTGCCCACCCTGCTTGATC (SEQ ID NO: 394) | 1885 |
| 86 | AAGTATCTGATCTGGGAGTGC (SEQ ID NO: 395) | 1918 |
| 87 | AAGTGGAGGAAGTTCAAGATG (SEQ ID NO: 396) | 1945 |
| 88 | AAGTTCAAGATGGCGCTGTTC (SEQ ID NO: 397) | 1954 |
| 89 | AAGATGGCGCTGTTCGAGCTG (SEQ ID NO: 398) | 1960 |
| 90 | AACACCGTCTTCATGGCCATG (SEQ ID NO: 399) | 2029 |
| 91 | AAGCCGGCAACATTGTCTTCA (SEQ ID NO: 400) | 2090 |
| 92 | AACATTGTCTTCACCGTGTTT (SEQ ID NO: 401) | 2098 |

TABLE 3-continued

Rat PN3 siRNA's

| Target | Target sequence | position in gene |
|---|---|---|
| 93 | AATGGAGATGGCCTTCAAGAT (SEQ ID NO: 402) | 2124 |
| 94 | AAGATCATTGCCTTCGACCCC (SEQ ID NO: 403) | 2140 |
| 95 | AAGAAGTGGAATATCTTCGAC (SEQ ID NO: 404) | 2176 |
| 96 | AAGTGGAATATCTTCGACTGT (SEQ ID NO: 405) | 2179 |
| 97 | AATATCTTCGACTGTGTCATC (SEQ ID NO: 406) | 2185 |
| 98 | AAGAAGGGCAGCCTGTCTGTG (SEQ ID NO: 407) | 2239 |
| 99 | AAGGGCAGCCTGTCTGTGCTC (SEQ ID NO: 408) | 2242 |
| 100 | AAGCTGGCCAAGTCCTGGCCC (SEQ ID NO: 409) | 2290 |
| 101 | AAGTCCTGGCCCACCCTGAAC (SEQ ID NO: 410) | 2299 |
| 102 | AACACCCTCATCAAGATCATC (SEQ ID NO: 411) | 2317 |
| 103 | AAGATCATCGGGAACTCCGTG (SEQ ID NO: 412) | 2329 |
| 104 | AACTCCGTGGGGGCCCTGGGC (SEQ ID NO: 413) | 2341 |
| 105 | AACCTGACCTTTATCCTGGCC (SEQ ID NO: 414) | 2362 |
| 106 | AAAGCAGCTTCTCTCAGAGGA (SEQ ID NO: 415) | 2412 |
| 107 | AAGGACGGCGTCTCCGTGTGG (SEQ ID NO: 416) | 2446 |
| 108 | AACGGCGAGAAGCTCCGCTGG (SEQ ID NO: 417) | 2467 |
| 109 | AAGCTCCGCTGGCACATGTGT (SEQ ID NO: 418) | 2476 |
| 110 | AATCCTCTGCGGGGAGTGGAT (SEQ ID NO: 419) | 2529 |
| 111 | AACATGTGGGTCTGCATGGAG (SEQ ID NO: 420) | 2554 |
| 112 | AAATCCATCTGCCTCATCCTC (SEQ ID NO: 421) | 2584 |
| 113 | AACCTAGTGGTGCTCAACCTT (SEQ ID NO: 422) | 2629 |
| 114 | AACCTTTTCATCGCTTTACTG (SEQ ID NO: 423) | 2644 |
| 115 | AACTCCTTCAGCGCGGACAAC (SEQ ID NO: 424) | 2668 |
| 116 | AACCTCACGGCTCCAGAGGAT (SEQ ID NO: 425) | 2686 |
| 117 | AACAACTTGCAGTTAGCACTG (SEQ ID NO: 426) | 2719 |
| 118 | AACTTGCAGTTAGCACTGGCC (SEQ ID NO: 427) | 2722 |
| 119 | AAGGTGGAGACCCAGCTGGGC (SEQ ID NO: 428) | 2821 |
| 120 | AAGCCCCCACTCACCAGCTCA (SEQ ID NO: 429) | 2845 |
| 121 | AAGAACCACATTGCCACTGAT (SEQ ID NO: 430) | 2872 |
| 122 | AACCACATTGCCACTGATGCT (SEQ ID NO: 431) | 2875 |
| 123 | AACCTGACAAAGCCAGCTCTC (SEQ ID NO: 432) | 2914 |
| 124 | AAAGCCAGCTCTCAGTAGCCC (SEQ ID NO: 433) | 2922 |
| 125 | AAGGAGAACCACGGGGACTTC (SEQ ID NO: 434) | 2944 |
| 126 | AACCACGGGGACTTCATCACT (SEQ ID NO: 435) | 2950 |
| 127 | AACGTGTGGGTCTCTGTGCCC (SEQ ID NO: 436) | 2977 |
| 128 | AATCTGACCTCGACGAGCTCG (SEQ ID NO: 437) | 3011 |
| 129 | AAGATATGGAGCAGGCTTCGC (SEQ ID NO: 438) | 3035 |
| 130 | AAGAGGACCCCAAGGGACAGC (SEQ ID NO: 439) | 3071 |
| 131 | AAGGGACAGCAGGAGCAGTTG (SEQ ID NO: 440) | 3082 |
| 132 | AAGTCCAAAAGTGTGAAAACC (SEQ ID NO: 441) | 3107 |
| 133 | AAAAGTGTGAAAACCACCAGG (SEQ ID NO: 442) | 3113 |
| 134 | AAGTGTGAAAACCACCAGGCA (SEQ ID NO: 443) | 3115 |
| 135 | AAAACCACCAGGCAGCCAGAA (SEQ ID NO: 444) | 3122 |
| 136 | AACCACCAGGCAGCCAGAAGC (SEQ ID NO: 445) | 3124 |
| 137 | AAGCCCAGCCTCCATGATGTC (SEQ ID NO: 446) | 3141 |
| 138 | AAGAGGAAGGATAGCCCTCAG (SEQ ID NO: 447) | 3199 |
| 139 | AAGGATAGCCCTCAGGTCCCT (SEQ ID NO: 448) | 3205 |
| 140 | AAATCCTGAGGAAGATCCCCG (SEQ ID NO: 449) | 3290 |
| 141 | AAGATCCCCGAGCTGGCAGAT (SEQ ID NO: 450) | 3301 |
| 142 | AAGGCTGCACTCGCCGCTGTC (SEQ ID NO: 451) | 3353 |
| 143 | AACGTGAATACTAGCAAGTCT (SEQ ID NO: 452) | 3382 |
| 144 | AATACTAGCAAGTCTCCTTGG (SEQ ID NO: 453) | 3388 |
| 145 | AAGTCTCCTTGGGCCACAGGC (SEQ ID NO: 454) | 3397 |
| 146 | AAGACCTGCTACCGCATCGTG (SEQ ID NO: 455) | 3430 |
| 147 | AACTACCTGGAAGAGAAACCC (SEQ ID NO: 456) | 3523 |
| 148 | AAGAGAAACCCCGAGTGAAGT (SEQ ID NO: 457) | 3533 |
| 149 | AAACCCCGAGTGAAGTCCGTG (SEQ ID NO: 458) | 3538 |
| 150 | AAGTCCGTGCTGGAGTACACT (SEQ ID NO: 459) | 3550 |
| 151 | AAGTGGGTAGCCTATGGCTTC (SEQ ID NO: 460) | 3613 |
| 152 | AAAAAGTATTTCACCAATGCC (SEQ ID NO: 461) | 3634 |
| 153 | AAAGTATTTCACCAATGCCTG (SEQ ID NO: 462) | 3636 |
| 154 | AATGCCTGGTGCTGGCTGGAC (SEQ ID NO: 463) | 3649 |
| 155 | AACATCTCCCTGACAAGCCTC (SEQ ID NO: 464) | 3682 |
| 156 | AAGCCTCATAGCGAAGATCCT (SEQ ID NO: 465) | 3696 |
| 157 | AAGATCCTTGAGTATTCCGAC (SEQ ID NO: 466) | 3709 |
| 158 | AAAGCCCTTCGGACTCTCCGT (SEQ ID NO: 467) | 3742 |
| 159 | AAGGCATGAGGGTAGTGGTGG (SEQ ID NO: 468) | 3797 |
| 160 | AACGTCCTCCTCGTCTGCCTC (SEQ ID NO: 469) | 3850 |
| 161 | AACCTCTTCGCCGGGAAATTT (SEQ ID NO: 470) | 3904 |
| 162 | AAATTTTCGAAGTGCGTCGAC (SEQ ID NO: 471) | 3919 |
| 163 | AAGTGCGTCGACACCAGAAAT (SEQ ID NO: 472) | 3928 |
| 164 | AAATAACCCATTTTCCAACGT (SEQ ID NO: 473) | 3945 |
| 165 | AACCCATTTTCCAACGTGAAT (SEQ ID NO: 474) | 3949 |

TABLE 3-continued

Rat PN3 siRNA's

| Target | Target sequence | position in gene |
|---|---|---|
| 166 | AACGTGAATTCGACGATGGTG (SEQ ID NO: 475) | 3961 |
| 167 | AATTCGACGATGGTGAATAAC (SEQ ID NO: 476) | 3967 |
| 168 | AATAACAAGTCCGAGTGTCAC (SEQ ID NO: 477) | 3982 |
| 169 | AACAAGTCCGAGTGTCACAAT (SEQ ID NO: 478) | 3985 |
| 170 | AAGTCCGAGTGTCACAATCAA (SEQ ID NO: 479) | 3988 |
| 171 | AATCAAAACAGCACCGGCCAC (SEQ ID NO: 480) | 4003 |
| 172 | AAAACAGCACCGGCCACTTCT (SEQ ID NO: 481) | 4007 |
| 173 | AACAGCACCGGCCACTTCTTC (SEQ ID NO: 482) | 4009 |
| 174 | AACGTCAAAGTCAACTTCGAC (SEQ ID NO: 483) | 4036 |
| 175 | AAAGTCAACTTCGACAACGTC (SEQ ID NO: 484) | 4042 |
| 176 | AACTTCGACAACGTCGCTATG (SEQ ID NO: 485) | 4048 |
| 177 | AACGTCGCTATGGGCTACCTC (SEQ ID NO: 486) | 4057 |
| 178 | AACCTTCAAAGGCTGGATGGA (SEQ ID NO: 487) | 4095 |
| 179 | AAAGGCTGGATGGACATAATG (SEQ ID NO: 488) | 4102 |
| 180 | AATGTATGCAGCTGTTGATTC (SEQ ID NO: 489) | 4119 |
| 181 | AACAGTCAGCCTAACTGGGAG (SEQ ID NO: 490) | 4150 |
| 182 | AACTGGGAGAACAACTTGTAC (SEQ ID NO: 491) | 4162 |
| 183 | AACAACTTGTACATGTACCTG (SEQ ID NO: 492) | 4171 |
| 184 | AACTTGTACATGTACCTGTAC (SEQ ID NO: 493) | 4174 |
| 185 | AATCTCTTTGTTGGGGTCATA (SEQ ID NO: 494) | 4234 |
| 186 | AATCGACAACTTCAACCAACA (SEQ ID NO: 495) | 4254 |
| 187 | AACTTCAACCAACAGAAAAAA (SEQ ID NO: 496) | 4261 |
| 188 | AACCAACAGAAAAAAAGCTA (SEQ ID NO: 497) | 4267 |
| 189 | AACAGAAAAAAAGCTAGGAG (SEQ ID NO: 498) | 4271 |
| 190 | AAAAAAAGCTAGGAGGCCAG (SEQ ID NO: 499) | 4276 |
| 191 | AAAAAGCTAGGAGGCCAGGA (SEQ ID NO: 500) | 4278 |
| 192 | AAAAGCTAGGAGGCCAGGACA (SEQ ID NO: 501) | 4280 |
| 193 | AAGCTAGGAGGCCAGGACATC (SEQ ID NO: 502) | 4282 |
| 194 | AAGAGCAGAAGAAGTACTACA (SEQ ID NO: 503) | 4313 |
| 195 | AAGAAGTACTACAATGCCATG (SEQ ID NO: 504) | 4321 |
| 196 | AAGTACTACAATGCCATGAAG (SEQ ID NO: 505) | 4324 |
| 197 | AATGCCATGAAGAAGCTGGGC (SEQ ID NO: 506) | 4333 |
| 198 | AAGAAGCTGGGCTCCAAGAAA (SEQ ID NO: 507) | 4342 |
| 199 | AAGCTGGGCTCCAAGAAACCC (SEQ ID NO: 508) | 4345 |
| 200 | AAGAAACCCCAGAAGCCCATC (SEQ ID NO: 509) | 4357 |
| 201 | AAACCCCAGAAGCCCATCCCA (SEQ ID NO: 510) | 4360 |
| 202 | AAGCCCATCCCACGGCCCCTG (SEQ ID NO: 511) | 4369 |
| 203 | AATAAGTACCAAGGCTTCGTG (SEQ ID NO: 512) | 4390 |
| 204 | AAGTACCAAGGCTTCGTGTTT (SEQ ID NO: 513) | 4393 |
| 205 | AAGGCTTCGTGTTTGACATCG (SEQ ID NO: 514) | 4400 |
| 206 | AAGCCTTTGACATCATCATCA (SEQ ID NO: 515) | 4430 |
| 207 | AACATGATCACCATGATGGTG (SEQ ID NO: 516) | 4468 |
| 208 | AAGACGAAGGTTCTGGGCAGA (SEQ ID NO: 517) | 4513 |
| 209 | AAGGTTCTGGGCAGAATCAAC (SEQ ID NO: 518) | 4519 |
| 210 | AATCAACCAGTTCTTTGTGGC (SEQ ID NO: 519) | 4533 |
| 211 | AACCAGTTCTTTGTGGCCGTC (SEQ ID NO: 520) | 4537 |
| 212 | AAGATGTTCGCCCTGCGACAG (SEQ ID NO: 521) | 4579 |
| 213 | AACGGCTGGAACGTGTTCGAC (SEQ ID NO: 522) | 4612 |
| 214 | AACGTGTTCGACTTCATAGTG (SEQ ID NO: 523) | 4621 |
| 215 | AATCCTTAAGTCACTGGAAAA (SEQ ID NO: 524) | 4677 |
| 216 | AAGTCACTGGAAAACTACTTC (SEQ ID NO: 525) | 4684 |
| 217 | AAAACTACTTCTCCCCGACGC (SEQ ID NO: 526) | 4694 |
| 218 | AACTACTTCTCCCCGACGCTC (SEQ ID NO: 527) | 4696 |
| 219 | AAGGGGATTCGCACGCTGCTC (SEQ ID NO: 528) | 4774 |
| 220 | AACATCGGCCTCCTCCTCTTC (SEQ ID NO: 529) | 4828 |
| 221 | AACGTCGTGGACGAGGCCGGC (SEQ ID NO: 530) | 4894 |
| 222 | AACTTCAAGACCTTTGGCAAC (SEQ ID NO: 531) | 4930 |
| 223 | AAGACCTTTGGCAACAGCATG (SEQ ID NO: 532) | 4936 |
| 224 | AACAGCATGCTGTGCCTGTTC (SEQ ID NO: 533) | 4948 |
| 225 | AACACGGGCCTCCCTACTGC (SEQ ID NO: 534) | 5017 |
| 226 | AACCTGCCCAACAGCAACGGC (SEQ ID NO: 535) | 5044 |
| 227 | AACAGCAACGGCTCCCGGGGG (SEQ ID NO: 536) | 5053 |
| 228 | AACGGCTCCCGGGGGAACTGC (SEQ ID NO: 537) | 5059 |
| 229 | AACTGCGGGAGCCCGGCGGTG (SEQ ID NO: 538) | 5074 |
| 230 | AACATGTACATCGCAGTGATT (SEQ ID NO: 539) | 5146 |
| 231 | AACTTCAACGTGGCCACCGAG (SEQ ID NO: 540) | 5173 |
| 232 | AACGTGGCCACCGAGGAGAGC (SEQ ID NO: 541) | 5179 |
| 233 | AAGTTCGACCCGGAGGCCACC (SEQ ID NO: 542) | 5251 |
| 234 | AATCCCCAAACCCAACCAGAA (SEQ ID NO: 543) | 5331 |
| 235 | AAACCCAACCAGAATATATTA (SEQ ID NO: 544) | 5338 |
| 236 | AACCAGAATATATTAATCCAG (SEQ ID NO: 545) | 5344 |
| 237 | AATATATTAATCCAGATGGAC (SEQ ID NO: 546) | 5350 |
| 238 | AATCCAGATGGACCTGCCGTT (SEQ ID NO: 547) | 5358 |
| 239 | AAGATCCACTGTCTGGACATC (SEQ ID NO: 548) | 5392 |

TABLE 3-continued

Rat PN3 siRNA's

| Target | Target sequence | position in gene |
|---|---|---|
| 240 | AAAGAACGTCTTGGGAGAATC (SEQ ID NO: 549) | 5427 |
| 241 | AACGTCTTGGGAGAATCCGGG (SEQ ID NO: 550) | 5431 |
| 242 | AATCCGGGGAGTTGGACTCCC (SEQ ID NO: 551) | 5444 |
| 243 | AAGACCAATATGGAAGAGAAG (SEQ ID NO: 552) | 5467 |
| 244 | AATATGGAAGAGAAGTTTATG (SEQ ID NO: 553) | 5473 |
| 245 | AAGAGAAGTTTATGGCGACCA (SEQ ID NO: 554) | 5480 |
| 246 | AAGTTTATGGCGACCAATCTC (SEQ ID NO: 555) | 5485 |
| 247 | AATCTCTCCAAAGCATCCTAT (SEQ ID NO: 556) | 5500 |
| 248 | AAAGCATCCTATGAACCAATA (SEQ ID NO: 557) | 5509 |
| 249 | AACCAATAGCCACCACCCTCC (SEQ ID NO: 558) | 5522 |
| 250 | AATAGCCACCACCCTCCGGTG (SEQ ID NO: 559) | 5526 |
| 251 | AAGCAGGAAGACCTCTCAGCC (SEQ ID NO: 560) | 5548 |
| 252 | AAGACCTCTCAGCCACAGTCA (SEQ ID NO: 561) | 5555 |
| 253 | AAAAGGCCTACCGGAGCTACA (SEQ ID NO: 562) | 5579 |
| 254 | AAGGCCTACCGGAGCTACATG (SEQ ID NO: 563) | 5581 |
| 255 | AACACCCTGCATGTGCCCAGG (SEQ ID NO: 564) | 5626 |
| 256 | AAGGCTACGTTACATTCATGG (SEQ ID NO: 565) | 5678 |
| 257 | AAACAGTGGACTCCCGGACAA (SEQ ID NO: 566) | 5700 |
| 258 | AAATCAGAAACTGCCTCTGCT (SEQ ID NO: 567) | 5719 |
| 259 | AAACTGCCTCTGCTACGTCTT (SEQ ID NO: 568) | 5726 |
| 260 | AACATTAACCCATCTAGCTCA (SEQ ID NO: 569) | 5794 |
| 261 | AACCCATCTAGCTCAATGCAA (SEQ ID NO: 570) | 5800 |
| 262 | AATGCAAAATGAAGATGAGGT (SEQ ID NO: 571) | 5814 |
| 263 | AAAATGAAGATGAGGTCGCTG (SEQ ID NO: 572) | 5819 |
| 264 | AATGAAGATGAGGTCGCTGCT (SEQ ID NO: 573) | 5821 |
| 265 | AAGATGAGGTCGCTGCTAAGG (SEQ ID NO: 574) | 5825 |
| 266 | AAGGAAGGAAACAGCCCTGGA (SEQ ID NO: 575) | 5842 |
| 267 | AAGGAAACAGCCCTGGACCTC (SEQ ID NO: 576) | 5846 |
| 268 | AAACAGCCCTGGACCTCAGTG (SEQ ID NO: 577) | 5850 |

Of the above siRNA sequences, five were selected for testing their ability to knock-down $Na_v1.8$ expression and function in vitro. The five siRNAs were selected so as to cover different regions of the entire 5874 nucleotide $Na_v1.8$ coding sequence. The five siRNA sequences, including the nucleotide position at which each sequence is located within the genome, are shown below in Table 4:

TABLE 4

| siRNA | Sequence | Nuc. Pos. |
|---|---|---|
| siRNA 1 | AAAAGCAGGACCAUUUCCAGA (SEQ ID NO: 1) | 289 |
| siRNA 2 | AAAGUGUCUGUCCAUUCCUGG (SEQ ID NO: 2) | 373 |
| siRNA 3 | AACUACACCAGCUUUGAUUCC (SEQ ID NO: 3) | 1000 |
| siRNA 4 | AAAUCCAUCUGCCUCAUCCUC (SEQ ID NO: 4) | 2584 |
| siRNA 5 | AAUAAGUACCAAGGCUUCGUG (SEQ ID NO: 5) | 4390 |

Example 2

The above five selected siRNA sequences, SEQ ID NOs: 1-5, were synthesized by Qiagen Inc., Valencia, Calif. We then cloned the $Na_v1.8$ cDNA into a pcDNA3.1 mammalian expression plasmid (Invitrogen, Carlsbad, Calif.) to generate a pcDNA-$Na_v1.8$ control expression plasmid. Upon transfection of the control plasmid into HEK293 cells (Microbix Biosystems, Inc., Ontario, Canada M8Z3A8), the cells exhibited high levels of $Na_v1.8$ RNA and protein expression. $Na_v1.8$ RNA expression was detected by Taqman® quantitative RT-PCR (Applied Biosystems, Foster City, Calif.), according to the manufacturer's instructions. $Na_v1.8$ protein expression in the HEK293 cells was detected by westernimmunoblot analysis using a $Na_v1.8$ specific peptide antibody, SOD1 (AnaSpec, San Jose, Calif.). The published peptide sequence was used for making the SOD1 antibody. See Novakovic et al., "Distribution of the tetrodotoxin-resistant sodium channel PN3 in rat sensory neurons in normal and neuropathic conditions, *J. Neuroscience*, vol. 18, no. 6, pp. 2174-2187 (1998).

Knock-Down of $Na_v1.8$ RNA

The five chemically synthesized siRNAs, SEQ ID NOs: 1-5, were individually co-transfected into HEK293 cells, along with the pcDNA-$Na_v1.8$ control expression plasmid. The final siRNA concentration in the transfected cells was maintained at 25 nM. 24 hours after transfection, the cells were lysed and the total RNA was purified from lysates using RNAeasy minicolumns (Qiagen, Valencia, Calif.) according to the manufacturer's instructions. Total RNA purified from either cells cotransfected with the individual siRNAs or control cells were used for quantitative RT-PCR analysis using rat $Na_v1.8$ specific Taqman® primer and probe sets (Applied Biosystems, Foster City, Calif.). Any rat $Na_v1.8$ specific primer should work in this regard. The design of PCR primers is known in the art.

The expression level of $Na_v1.8$ RNA in siRNA transfected cells was compared with RNA expression in control cells. The control cells, which were transfected with pcDNA3.1-$Na_v1.8$ control expression plasmid, exhibited a relative $rNa_v1.8$ RNA expression level of 100%. The siRNA 1 cells, which were co-transfected with pcDNA3.1-$Na_v1.8$ control expression plasmid and the siRNA of SEQ ID NO: 1, exhibited a relative $rNa_v1.8$ RNA expression level of 20%. The siRNA 2 cells, which were co-transfected with pcDNA3.1-$Na_v1.8$ control expression plasmid and the siRNA of SEQ ID NO: 2, exhibited a relative $rNa_v1.8$ RNA expression level of 65%. The siRNA 3 cells, which were co-transfected with pcDNA3.1-$Na_v1.8$ control expression plasmid and the siRNA of SEQ ID NO: 3, exhibited a relative $rNa_v1.8$ RNA expression level of 30%. The siRNA 4 cells, which were co-transfected with pcDNA3.1-$Na_v1.8$ control expression plasmid and the siRNA of SEQ ID NO: 4, exhibited a relative $rNa_v1.8$ RNA expression level of 115%. The siRNA 5 cells, which were co-transfected with pcDNA3.1-Na$_v$1.8 control expression plasmid and the siRNA of SEQ ID NO: 5, exhibited a relative rNa$_v$1.8 RNA expression level of 70%.

Cells co-transfected with either siRNA 1 or siRNA 3 showed high levels of Na$_v$1.8 RNA silencing while cells co-transfected with either siRNA 2 and siRNA 5 showed moderate levels of RNA silencing. No knock-down in Na$_v$1.8 RNA expression was seen in cells transfected with siRNA 4.

Knock-Down of Na$_v$1.8 Protein

The five chemically synthesized siRNAs, SEQ ID NOs: 1-5, were individually co-transfected into HEK293 cells, along with the pcDNA-Na$_v$1.8 control expression plasmid. The final siRNA concentration in the transfected cells was maintained at 25 nM. 24 hours after transfection, the cells were lysed in a denaturing lysis buffer and the lysates were run on denaturation 12% TBE gels (Invitrogen, Carlsbad, Calif.). The gels were blotted onto nitrocellulose sheets and probed with the Na$_v$1.8 specific antibody—SOD1 (AnaSpec, San Jose, Calif.).

Lysates from cells transfected with pcDNA-Na$_v$1.8 control expression plasmid, the control cells, showed high levels of Na$_v$1.8 protein expression. Lysates from cells co-transfected with pcDNA-Na$_v$1.8 control expression plasmid and either siRNA 1 or siRNA 3 showed almost complete abolition of Na$_v$1.8 protein expression. Lysates from cells co-transfected with pcDNA-Na$_v$1.8 control expression plasmid and either siRNA 2 or siRNA 5 showed moderate levels of Na$_v$1.8 protein expression. Lysates from cells co-transfected with pcDNA-Na$_v$1.8 control expression plasmid and siRNA 4 showed no reduction in Na$_v$1.8 protein expression.

Example 3

Next, we determined whether siRNA was capable of functionally knocking-down the Na$_v$1.8 sodium channel. This determination was made using a FlexStation® assay (Molecular Devices, Sunnyvale, Calif.) and voltage clamp measurements. We stably expressed, by retroviral integration, the Na$_v$1.8 coding sequence in the neuroblastoma/DRG fusion cell line ND7/23 (European Collection of Cell Cultures, Wiltshire, UK). The ND7/23 cell line is a mouse neuroblastoma and rat neurone hybrid, which is identified by European Collection of Cell Cultures No. 92090903. This ND7/23-Na$_v$1.8 cell line showed consistent and high levels of Na$_v$1.8 sodium current in both FlexStation® membrane potential assays and in whole cell voltage clamp measurements.

FlexStation® Assay

We individually transfected each of the above five selected siRNA sequences, SEQ ID NOs: 1-5, into the ND7/23-Na$_v$1.8 cell line. Functional knock-down of Na$_v$1.8 by the siRNAs was confirmed using the membrane potential assay on the FlexStation® according to the manufacturer's instructions. Readings on the FlexStation® were taken 1 day post transfection with individual siRNAs.

The luminescence level of control cells was compared to that of cells individually transfected with siRNAs 1-5. All cells were transfected with the Na$_v$1.8 coding sequence. The control cells exhibited a luminescence level of 175,000 units. The siRNA 1 cells, which were subsequently transfected with the siRNA of SEQ ID NO: 1, exhibited a luminescence level of 48,000 units. The siRNA 2 cells, which were subsequently transfected with the siRNA of SEQ ID NO: 2, exhibited a luminescence level of 70,000 units. The siRNA 3 cells, which were subsequently transfected with the siRNA of SEQ ID NO: 3, exhibited a luminescence level of 45,000. The siRNA 4 cells, which were subsequently transfected with the siRNA of SEQ ID NO: 4, exhibited a luminescence level of 151,000. The siRNA 5 cells, which were subsequently transfected with the siRNA of SEQ ID NO: 5, exhibited a luminescence level of 80,000.

siRNAs 1 and 3 blocked Na$_v$1.8 derived membrane potential while siRNAs 2 and 5 showed moderate levels of blockage in membrane potential. siRNA 4 showed minimal or no blockage in membrane potential. The level of blockage in membrane potential by the individual siRNAs was similar to the level of both protein and RNA silencing by the siRNAs in the HEK293 system. In another example of this experiment, the control cells exhibited a luminescence level of 198,698 units. The siRNA 1 cells, which were subsequently transfected with the siRNA of SEQ ID NO: 1, exhibited a luminescence level of 46,068 units (corresponding to 23% of control signal). The siRNA 2 cells, which were subsequently transfected with the siRNA of SEQ ID NO: 2, exhibited a luminescence level of 71,523 units (corresponding to 36% of control). The siRNA 3 cells, which were subsequently transfected with the siRNA of SEQ ID NO: 3, exhibited a luminescence level of 42,422 units (corresponding to 21% of control). The siRNA 4 cells, which were subsequently transfected with the siRNA of SEQ ID NO: 4, exhibited a luminescence level of 151,067 units (corresponding to 76% of control). The siRNA 5 cells, which were subsequently transfected with the siRNA of SEQ ID NO: 5, exhibited a luminescence level of 80,567 units (corresponding to 41% of control).

Voltage Clamp Measurements

To further confirm functional knock-down of Na$_v$1.8 sodium currents, we performed whole cell voltage clamp measurements in ND7/23-Na$_v$1.8 control cells that were subsequently transfected with siRNA 1. Briefly, ND7/23-Na$_v$1.8 cells were either mock transfected with non-silencing siRNAs, the control cells, or transfected with siRNA 1, the siRNA 1 cells. The siRNA 1 concentration was maintained at 25 nM. Successfully transfected cells, which were identified by cotransfection with Green Fluorescent Protein (GFP) (Clontech, Palo Alto, Calif.), were used for whole cell voltage clamp measurements. Measurements were made both 24 and 48 hours post transfection.

At 24 hours post transfection, the control cells exhibited a peak amplitude of −900 while the siRNA 1 cells exhibited a peak amplitude of −175. At 48 hours post transfection, the control cells exhibited a peak amplitude of −775 while the siRNA 1 cells exhibited a peak amplitude of −175. Therefore, we observed almost total blockage in sodium currents in siRNA 1 transfected cells. In fact, the blockage was greater than 85%. Furthermore, the specificity of Na$_v$1.8 block was confirmed by the observation that no block in tetrodotoxin-sensitive currents was seen in siRNA 1 treated ND7/23-Na$_v$1.8 cells.

In another example, at 24 hours post transfection, the control cells (sample size=10) exhibited a mean peak whole-cell Na$_v$1.8 current amplitude of −912 pA while the siRNA 1 cells (sample size=11) exhibited a mean peak amplitude of −169 pA. Thus, by 24h after transfection, siRNA1 had reduced the NaV1.8 current amplitude to 18.5% of control. Furthermore, the specificity of the siRNA effect to the intended tetrodotoxin-resistant Na$_v$1.8 sodium channel was confirmed by the observation that no reduction in the amplitude of the background tetrodotoxin-sensitive sodium currents was seen in siRNA 1 treated ND7/23-Na$_v$1.8 cells at either 24 or 48h post-transfection.

Example 4

In order to identify backup siRNAs that exhibit high levels of Na$_v$1.8 knock-down, we designed six additional siRNAs, SEQ ID NOs: 6-11, in the region of the Na$_v$1.8 coding sequences covering siRNA 1 and siRNA 3. These six additional siRNAs were designed using the same procedures outlined in Example 1, and have the following sequences, as shown in Table 5 below:

TABLE 5

| siRNA | Sequence | |
|---|---|---|
| siRNA 6 | AAGAAGGCCAGAACCAAGCAC | (SEQ ID NO: 6) |
| siRNA 7 | AAGUUCUAUGGUGAGCUCCCA | (SEQ ID NO: 7) |
| siRNA 8 | AACUGGCUGGACUUCAGUGUC | (SEQ ID NO: 8) |
| siRNA 9 | AACUGUUUCUGUGAUCCCAGG | (SEQ ID NO: 9) |
| siRNA 10 | AAGGCUGACAACCUCUCAUCU | (SEQ ID NO: 10) |
| siRNA 11 | AAGAGUCUAAGCUGAAGUGCC | (SEQ ID NO: 11) |

All six additional siRNAs, SEQ ID NOs: 6-11, were screened for their ability to knock-down $Na_v1.8$ derived membrane potential in ND7/23 cells. Using procedures similar to those in Example 3, the luminescence level of control cells was compared to that of cells individually transfected with siRNAs 6-11. The control cells exhibited a luminescence level of 175,000 units. The siRNA 6 cells, which were subsequently transfected with the siRNA of SEQ ID NO: 6, exhibited a luminescence level of 85,000 units. The siRNA 7 cells, which were subsequently transfected with the siRNA of SEQ ID NO: 7, exhibited a luminescence level of 50,000 units. The siRNA 8 cells, which were subsequently transfected with the siRNA of SEQ ID NO: 8, exhibited a luminescence level of 45,000. The siRNA 9 cells, which were subsequently transfected with the siRNA of SEQ ID NO: 9, exhibited a luminescence level of 43,000. The siRNA 10 cells, which were subsequently transfected with the siRNA of SEQ ID NO: 10, exhibited a luminescence level of 10,000. The siRNA 11 cells, which were subsequently transfected with the siRNA of SEQ ID NO: 11, exhibited a luminescence level of 35,000. Using procedures similar to those in Examples 2 and 3, we determined that all six siRNAs were also capable of blocking $Na_v1.8$ expression and function, resulting in a collection of efficacious siRNAs.

In another example, the control cells exhibited a luminescence level of 198,698 units. The siRNA 6 cells, which were subsequently transfected with the siRNA of SEQ ID NO: 6, exhibited a luminescence level of 86,105 units (43% of control cells). The siRNA 7 cells, which were subsequently transfected with the siRNA of SEQ ID NO: 7, exhibited a luminescence level of 50,237 units (25% of control cells). The siRNA 8 cells, which were subsequently transfected with the siRNA of SEQ ID NO: 8, exhibited a luminescence level of 44,038 units (22% of control cells). The siRNA 9 cells, which were subsequently transfected with the siRNA of SEQ ID NO: 9, exhibited a luminescence level of 46,917 units (24% of control cells). The siRNA 10 cells, which were subsequently transfected with the siRNA of SEQ ID NO: 10, exhibited a luminescence level of 21,847 (7% of control cells). The siRNA 11 cells, which were subsequently transfected with the siRNA of SEQ ID NO: 11, exhibited a luminescence level of 30,587 (15% of control cells).

Example 5

Adenoviral Delivery of $Na_v1.8$ siRNA

For long term siRNA delivery to cells and knock-down of $Na_v1.8$ function, we designed an adenoviral vector for driving siRNA expression. Briefly, the construct was designed to express siRNA 3 (SEQ ID NO: 3) under the control of a U6 promoter cassette. The siRNA 3 expression cassette was then cloned into an E1-deleted pTG4213 adenoviral backbone (Transgene SA, France).

ND7/23-$Na_v1.8$ cells from Example 3 were infected with the above siRNA 3 adenoviral vector construct at a concentration of $1e^9$ particles/ml. Control cells were infected at the same concentration with a control adenovirus containing a U6 promoter cassette. Infected cells were lysed for total RNA purification in order to perform either Taqman® assays or FlexStation® assays.

For Taqman® assays, Infected cells were lysed at 6, 8 and 10 days post infection (dpi), and RNA purified from lysates was used to measure $Na_v1.8$ RNA expression by quantitative RT-PCR analysis. At 6 days post infection, $Na_v1.8$ RNA expression, expressed as a percentage of non-silencing adenoviral siRNA, was 18%. At 8 days post infection, $Na_v1.8$ RNA expression, expressed as a percentage of non-silencing adenoviral siRNA, was 22%. At 10 days post infection, $Na_v1.8$ RNA expression, expressed as a percentage of non-silencing adenoviral siRNA, was 30%.

For FlexStation® assays, infected cells were used for measuring $Na_v1.8$ derived membrane potential on the FlexStation® at 2, 4, 6, 8 and 10 days post infection (dpi). At each time point, knock-down in membrane potential in siRNA 3 adenoviral vector construct infected cells was compared to membrane potential in control adenoviral infected cells. At 2 days post infection, percent sodium current, as compared to non-silencing adenoviral-siRNA, was 45%. At 4 days post infection, percent sodium current, as compared to non-silencing adenoviral-siRNA, was 15%. At 6 days post infection, percent sodium current, as compared to non-silencing adenoviral-siRNA, was 8%. At 8 days post infection, percent sodium current, as compared to non-silencing adenoviral-siRNA, was 8%. At 10 days post infection, percent sodium current, as compared to non-silencing adenoviral-siRNA, was 4%.

To further confirm that the reduction in RNA expression seen with the viral-siRNA construct was representative of an attenuation in function NaV1.8 sodium channel activity, we performed a number of whole-cell voltage clamp experiments to directly measure NaV1.8-mediated current at various times post-infection. In each of these experiments, current amplitudes were measured in a sample of ND7/23-NaV1.8 cells that had been previously infected with either a control, non-silencing siRNA construct of with the adenoviral-siRNA 3 construct. At 4 days post infection with the non-silencing viral construct total mean (10 cells sampled) whole cell NaV1.8 current was −821 pA whilst that measured in siRNA3-virus infected cells was −101 pA (corresponding to 12.3% of control). At 6 days post infection, with the non-silencing viral construct total mean (10 cells sampled) whole cell NaV1.8 current was −932 pA whilst that measured in siRNA3-virus infected cells was −247.7 pA (corresponding to 26.6% of control). At 10 days post infection, with the non-silencing viral construct total mean (10 cells sampled) whole cell NaV1.8 current was −976.7 pA whilst that measured in siRNA3-virus infected cells was −542.7 pA (corresponding to 55.6% of control).

Thus, Taqman® and FlexStation® and voltage-clamp assays showed knock-down of $Na_v1.8$ RNA expression and $Na_v1.8$ derived membrane potential that lasted for at least 8 dpi. infection by siRNA expressing adenovirus resulted in at least 80% knock-down of $Na_v1.8$ expression and function.

Thus, high levels of sustained $Na_v1.8$ block were demonstrated using viral vectors for siRNA delivery.

Example 6

Effect of $Na_v1.8$ siRNA in a Rat Model of Chronic Pain

The effect of $Na_v1.8$-siRNA was investigated in a rat model of chronic pain using siRNA 3. Hind paw tactile sensitivity was measured in a cohort of rats using graded von-Frey microfilaments (=baseline sensitivity). The same rats were then subjected to a surgical procedure that entailed exposure of the left sciatic nerve at mid thigh level followed by a loose ligation injury effected using standard suture material. The wound was closed and the animals allowed to recover from the procedure for a period of at least one week prior to any subsequent behavioral evaluation. The nerve trauma resulting from the procedure resulted in a tactile hypersensitivity in the left hind paw, a condition that is referred to as tactile allodynia. The degree of allodynia is readily quantified using the same von-Frey filament procedure as used for the baseline measurements, such measurements were taken 13 days after the surgical day. In order to evaluate the effects of siRNA 3 (SEQ ID No 3) on the allodynia, the siRNA was delivered as a duplex into the intrathecal space around the spinal cord via a permanent indwelling intrathecal catheter. Two separate injections of 2 µg of siRNA 3 were made daily over a period of three days, control rats received an identical injection of vehicle only using the same timing protocol.

Baseline hindpaw sensitivities of rats used in these experiments ranged between 13 to 15 grams force. Thirteen days after the nerve trauma injury the hindpaw sensitivities were re-determined for each rat and were found to be in the range of 1.2±0.4 g in the cohort designated the siRNA group and 2.1±0.4 g in the control cohort (cohort size=6 rats in drug-treated group and 5 rats in the control group). Nerve injury resulted, therefore, in a profoundly painful tactile hypersensitivity (allodynia) that is typical of that seen in human subjects having suffered injuries that lead to a chronic neuropathic pain state. Regular assessments revealed the painful allodynic state to be maintained (typically <2.1 g) through days 13 to 21 in the control cohort of rats that received vehicle-only injections. By contrast, rats that were injected with siRNA 3 for three days, commencing immediately after their day 13 assessment, showed a pronounced reversal of their painful allodynia (8.1±2.1 g, assessed on day 16). Rats treated with siRNA 3 showed a consistently improved pain score, (e.g., an amelioration of an experimentally-induced chronic pain state) compared to controls, over several subsequent days during which measurements were taken.

We claim:

1. An isolated or recombinant short interfering nucleic acid comprising the nucleotide sequence of SEQ ID NO: 3, or an analogue thereof.

2. The isolated or recombinant short interfering nucleic acid of claim 1 comprising the nucleotide sequence of SEQ ID NO: 3.

3. The isolated or recombinant short interfering nucleic acid of claim 2, further comprising a 3' overhang.

4. The isolated or recombinant short interfering nucleic acid of claim 2, further comprising a complementary nucleotide sequence to SEQ ID NO: 3.

5. The isolated or recombinant short interfering nucleic acid of claim 4, wherein the complementary nucleotide sequence further comprises a 3' overhang.

6. A pharmaceutical composition comprising a short interfering nucleic acid and a pharmaceutically acceptable carrier, wherein the short interfering nucleic acid comprises SEQ ID NO: 3or an analogue thereof.

7. The pharmaceutical composition of claim 6, wherein the short interfering nucleic acid comprises SEQ ID NO: 3.

8. The pharmaceutical composition of claim 7, wherein the short interfering nucleic acid further comprises a 3' overhang.

9. The pharmaceutical composition of claim 6, wherein the short interfering nucleic acid further comprises a complementary nucleotide sequence to SEQ ID NO: 3.

10. The pharmaceutical composition of claim 6, wherein the complementary nucleotide sequence further comprises a 3' overhang.

11. An isolated or recombinant short interfering nucleic acid comprising a nucleotide sequence and a complementary nucleotide sequence thereto, wherein the nucleotide sequence is SEQ ID NO: 3.

12. The isolated or recombinant short interfering nucleic acid of claim 11, wherein the nucleotide sequence further comprises a 3' overhang and the complementary nucleotide sequence further comprises a 3' overhang.

13. A pharmaceutical composition comprising a short interfering nucleic acid and a pharmaceutically acceptable carrier, wherein the short interfering nucleic acid comprises a nucleotide sequence and a complementary nucleotide sequence thereto, wherein the nucleotide sequence is SEQ ID NO: 3.

14. The pharmaceutical composition of claim 13, wherein the nucleotide sequence further comprises a 3° overhang and the complementary nucleotide sequence further comprises a 3' overhang.

* * * * *

UNITED STATES PATENT AND TRADEMARK OFFICE
CERTIFICATE OF CORRECTION

PATENT NO. : 8,309,703 B2  
APPLICATION NO. : 12/789564  
DATED : November 13, 2012  
INVENTOR(S) : Sameer Goregaoker, John C. Hunter and Tony Priestley Page 1 of 1

It is certified that error appears in the above-identified patent and that said Letters Patent is hereby corrected as shown below:

On the title page at item (73) Assignee, insert --Canji, Inc. (Palo Alto, CA)-- after "Merck Sharp & Dohme Corp. (Rahway, NJ)"

Signed and Sealed this  
Ninth Day of August, 2016

Michelle K. Lee  
*Director of the United States Patent and Trademark Office*

SEQUENCE LISTING

```
<160> NUMBER OF SEQ ID NOS: 577

<210> SEQ ID NO 1
<211> LENGTH: 21
<212> TYPE: RNA
<213> ORGANISM: Artificial
<220> FEATURE:
<223> OTHER INFORMATION: siRNA sense strand

<400> SEQUENCE: 1
aaaagcagga ccauuccag a                                              21

<210> SEQ ID NO 2
<211> LENGTH: 21
<212> TYPE: RNA
<213> ORGANISM: Artificial
<220> FEATURE:
<223> OTHER INFORMATION: siRNA sense strand

<400> SEQUENCE: 2
aaagugucug uccauuccug g                                             21

<210> SEQ ID NO 3
<211> LENGTH: 21
<212> TYPE: RNA
<213> ORGANISM: Artificial
<220> FEATURE:
<223> OTHER INFORMATION: siRNA sense strand

<400> SEQUENCE: 3
aacuacacca gcuuugauuc c                                             21

<210> SEQ ID NO 4
<211> LENGTH: 21
<212> TYPE: RNA
<213> ORGANISM: Artificial
<220> FEATURE:
<223> OTHER INFORMATION: siRNA sense strand
```

-continued

<400> SEQUENCE: 4
aaauccaucu gccucauccu c                                              21

<210> SEQ ID NO 5
<211> LENGTH: 21
<212> TYPE: RNA
<213> ORGANISM: Artificial
<220> FEATURE:
<223> OTHER INFORMATION: siRNA sense strand

<400> SEQUENCE: 5
aauaaguacc aaggcuucgu g                                              21

<210> SEQ ID NO 6
<211> LENGTH: 21
<212> TYPE: RNA
<213> ORGANISM: Artificial
<220> FEATURE:
<223> OTHER INFORMATION: siRNA sense strand

<400> SEQUENCE: 6
aagaaggcca gaaccaagca c                                              21

<210> SEQ ID NO 7
<211> LENGTH: 21
<212> TYPE: RNA
<213> ORGANISM: Artificial
<220> FEATURE:
<223> OTHER INFORMATION: siRNA sense strand

<400> SEQUENCE: 7
aaguucuaug gugagcuccc a                                              21

<210> SEQ ID NO 8
<211> LENGTH: 21
<212> TYPE: RNA
<213> ORGANISM: Artificial
<220> FEATURE:
<223> OTHER INFORMATION: siRNA sense strand

<400> SEQUENCE: 8
aacuggcugg acuucagugu c                                              21

<210> SEQ ID NO 9
<211> LENGTH: 21
<212> TYPE: RNA
<213> ORGANISM: Artificial
<220> FEATURE:
<223> OTHER INFORMATION: siRNA sense strand

<400> SEQUENCE: 9
aacuguuucu gugaucccag g                                              21

<210> SEQ ID NO 10
<211> LENGTH: 21
<212> TYPE: RNA
<213> ORGANISM: Artificial
<220> FEATURE:
<223> OTHER INFORMATION: siRNA sense strand

<400> SEQUENCE: 10
aaggcugaca accucucauc u                                              21

```
<210> SEQ ID NO 11
<211> LENGTH: 21
<212> TYPE: RNA
<213> ORGANISM: Artificial
<220> FEATURE:
<223> OTHER INFORMATION: siRNA sense strand

<400> SEQUENCE: 11
aagagucuaa gcugaagugc c                                             21

<210> SEQ ID NO 12
<211> LENGTH: 21
<212> TYPE: DNA
<213> ORGANISM: Homo sapiens

<400> SEQUENCE: 12
aattccccat tggatccctc g                                             21

<210> SEQ ID NO 13
<211> LENGTH: 21
<212> TYPE: DNA
<213> ORGANISM: Homo sapiens

<400> SEQUENCE: 13
aaactaacaa cttccgtcgc t                                             21

<210> SEQ ID NO 14
<211> LENGTH: 21
<212> TYPE: DNA
<213> ORGANISM: Homo sapiens

<400> SEQUENCE: 14
aacaacttcc gtcgctttac t                                             21

<210> SEQ ID NO 15
<211> LENGTH: 21
<212> TYPE: DNA
<213> ORGANISM: Homo sapiens

<400> SEQUENCE: 15
aacttccgtc gctttactcc g                                             21

<210> SEQ ID NO 16
<211> LENGTH: 21
<212> TYPE: DNA
<213> ORGANISM: Homo sapiens

<400> SEQUENCE: 16
aagcaaattg ctgccaagca g                                             21

<210> SEQ ID NO 17
<211> LENGTH: 21
<212> TYPE: DNA
<213> ORGANISM: Homo sapiens

<400> SEQUENCE: 17
aaattgctgc caagcaggga a                                             21

<210> SEQ ID NO 18
<211> LENGTH: 21
<212> TYPE: DNA
<213> ORGANISM: Homo sapiens

<400> SEQUENCE: 18
aagcagggaa caaagaaagc c                                             21
```

```
<210> SEQ ID NO 19
<211> LENGTH: 21
<212> TYPE: DNA
<213> ORGANISM: Homo sapiens

<400> SEQUENCE: 19
aacaaagaaa gccagagaga a                                              21

<210> SEQ ID NO 20
<211> LENGTH: 21
<212> TYPE: DNA
<213> ORGANISM: Homo sapiens

<400> SEQUENCE: 20
aaagaaagcc agagagaagc a                                              21

<210> SEQ ID NO 21
<211> LENGTH: 21
<212> TYPE: DNA
<213> ORGANISM: Homo sapiens

<400> SEQUENCE: 21
aaagccagag agaagcatag g                                              21

<210> SEQ ID NO 22
<211> LENGTH: 21
<212> TYPE: DNA
<213> ORGANISM: Homo sapiens

<400> SEQUENCE: 22 aagcatagggg agcagaagga c                                             21

<210> SEQ ID NO 23
<211> LENGTH: 21
<212> TYPE: DNA
<213> ORGANISM: Homo sapiens

<400> SEQUENCE: 23
aaggaccaag aagagaagcc t                                              21

<210> SEQ ID NO 24
<211> LENGTH: 21
<212> TYPE: DNA
<213> ORGANISM: Homo sapiens

<400> SEQUENCE: 24
aagaagagaa gcctcggccc c                                              21

<210> SEQ ID NO 25
<211> LENGTH: 21
<212> TYPE: DNA
<213> ORGANISM: Homo sapiens

<400> SEQUENCE: 25
aagagaagcc tcggccccag c                                              21

<210> SEQ ID NO 26
<211> LENGTH: 21
<212> TYPE: DNA
<213> ORGANISM: Homo sapiens

<400> SEQUENCE: 26
aagcctcggc cccagctgga c                                              21
```

-continued

```
<210> SEQ ID NO 27
<211> LENGTH: 21
<212> TYPE: DNA
<213> ORGANISM: Homo sapiens

<400> SEQUENCE: 27
aaagcctgca accagctgcc c                                              21

<210> SEQ ID NO 28
<211> LENGTH: 21
<212> TYPE: DNA
<213> ORGANISM: Homo sapiens

<400> SEQUENCE: 28
aaccagctgc ccaagttcta t                                              21

<210> SEQ ID NO 29
<211> LENGTH: 21
<212> TYPE: DNA
<213> ORGANISM: Homo sapiens

<400> SEQUENCE: 29
aagttctatg gtgagctccc a                                              21

<210> SEQ ID NO 30
<211> LENGTH: 21
<212> TYPE: DNA
<213> ORGANISM: Homo sapiens

<400> SEQUENCE: 30
aactgatcgg ggagcccctg g                                              21

<210> SEQ ID NO 31
<211> LENGTH: 21
<212> TYPE: DNA
<213> ORGANISM: Homo sapiens

<400> SEQUENCE: 31
aacaaaggga ggaccatttc c                                              21

<210> SEQ ID NO 32
<211> LENGTH: 21
<212> TYPE: DNA
<213> ORGANISM: Homo sapiens

<400> SEQUENCE: 32
aaagggagga ccatttcccg g                                              21

<210> SEQ ID NO 33
<211> LENGTH: 21
<212> TYPE: DNA
<213> ORGANISM: Homo sapiens

<400> SEQUENCE: 33
aacctgatca gaagaacggc c                                              21

<210> SEQ ID NO 34
<211> LENGTH: 21
<212> TYPE: DNA
<213> ORGANISM: Homo sapiens

<400> SEQUENCE: 34
aagaacggcc atcaaagtgt c                                              21
```

-continued

```
<210> SEQ ID NO 35
<211> LENGTH: 21
<212> TYPE: DNA
<213> ORGANISM: Homo sapiens

<400> SEQUENCE: 35
aacggccatc aaagtgtctg t                                    21

<210> SEQ ID NO 36
<211> LENGTH: 21
<212> TYPE: DNA
<213> ORGANISM: Homo sapiens

<400> SEQUENCE: 36
aaagtgtctg tccactcgtg g                                    21

<210> SEQ ID NO 37
<211> LENGTH: 21
<212> TYPE: DNA
<213> ORGANISM: Homo sapiens

<400> SEQUENCE: 37
aattgtgtgt gcatgacccg a                                    21

<210> SEQ ID NO 38
<211> LENGTH: 21
<212> TYPE: DNA
<213> ORGANISM: Homo sapiens

<400> SEQUENCE: 38
aactgacctt ccagagaaaa t                                    21

<210> SEQ ID NO 39
<211> LENGTH: 21
<212> TYPE: DNA
<213> ORGANISM: Homo sapiens

<400> SEQUENCE: 39
aaaattgaat atgtcttcac t                                    21

<210> SEQ ID NO 40
<211> LENGTH: 21
<212> TYPE: DNA
<213> ORGANISM: Homo sapiens

<400> SEQUENCE: 40
aattgaatat gtcttcactg t                                    21

<210> SEQ ID NO 41
<211> LENGTH: 21
<212> TYPE: DNA
<213> ORGANISM: Homo sapiens

<400> SEQUENCE: 41
aatatgtctt cactgtcatt t                                    21

<210> SEQ ID NO 42
<211> LENGTH: 21
<212> TYPE: DNA
<213> ORGANISM: Homo sapiens

<400> SEQUENCE: 42
aagccttgat aaagatactg g                                    21
```

-continued

```
<210> SEQ ID NO 43
<211> LENGTH: 21
<212> TYPE: DNA
<213> ORGANISM: Homo sapiens

<400> SEQUENCE: 43
aaagatactg gcaagaggat t                                             21

<210> SEQ ID NO 44
<211> LENGTH: 21
<212> TYPE: DNA
<213> ORGANISM: Homo sapiens

<400> SEQUENCE: 44
aagaggattt tgtctaaatg a                                             21

<210> SEQ ID NO 45
<211> LENGTH: 21
<212> TYPE: DNA
<213> ORGANISM: Homo sapiens

<400> SEQUENCE: 45
aaatgagttc acgtacctga g                                             21

<210> SEQ ID NO 46
<211> LENGTH: 21
<212> TYPE: DNA
<213> ORGANISM: Homo sapiens

<400> SEQUENCE: 46
aactggctgg attttagcgt c                                             21

<210> SEQ ID NO 47
<211> LENGTH: 21
<212> TYPE: DNA
<213> ORGANISM: Homo sapiens

<400> SEQUENCE: 47
aatagatctc cgtgggatct c                                             21

<210> SEQ ID NO 48
<211> LENGTH: 21
<212> TYPE: DNA
<213> ORGANISM: Homo sapiens

<400> SEQUENCE: 48
aaaaacagtt tctgtgatcc c                                             21

<210> SEQ ID NO 49
<211> LENGTH: 21
<212> TYPE: DNA
<213> ORGANISM: Homo sapiens

<400> SEQUENCE: 49
aaacagtttc tgtgatccca g                                             21

<210> SEQ ID NO 50
<211> LENGTH: 21
<212> TYPE: DNA
<213> ORGANISM: Homo sapiens

<400> SEQUENCE: 50
aaggtcattg tgggggccct g                                             21
```

```
<210> SEQ ID NO 51
<211> LENGTH: 21
<212> TYPE: DNA
<213> ORGANISM: Homo sapiens

<400> SEQUENCE: 51
aagaaactgg ctgatgtgac c                                              21

<210> SEQ ID NO 52
<211> LENGTH: 21
<212> TYPE: DNA
<213> ORGANISM: Homo sapiens

<400> SEQUENCE: 52
aaactggctg atgtgaccat c                                              21

<210> SEQ ID NO 53
<211> LENGTH: 21
<212> TYPE: DNA
<213> ORGANISM: Homo sapiens

<400> SEQUENCE: 53
aagtgttttt gccttggtgg g                                              21

<210> SEQ ID NO 54
<211> LENGTH: 21
<212> TYPE: DNA
<213> ORGANISM: Homo sapiens

<400> SEQUENCE: 54
aactcttcaa gggcaacctc a                                              21

<210> SEQ ID NO 55
<211> LENGTH: 21
<212> TYPE: DNA
<213> ORGANISM: Homo sapiens

<400> SEQUENCE: 55
aagggcaacc tcaaaaataa a                                              21

<210> SEQ ID NO 56
<211> LENGTH: 21
<212> TYPE: DNA
<213> ORGANISM: Homo sapiens

<400> SEQUENCE: 56
aacctcaaaa ataaatgtgt c                                              21

<210> SEQ ID NO 57
<211> LENGTH: 21
<212> TYPE: DNA
<213> ORGANISM: Homo sapiens

<400> SEQUENCE: 57
aaaaataaat gtgtcaagaa t                                              21

<210> SEQ ID NO 58
<211> LENGTH: 21
<212> TYPE: DNA
<213> ORGANISM: Homo sapiens

<400> SEQUENCE: 58
aaataaatgt gtcaagaatg a                                              21
```

```
<210> SEQ ID NO 59
<211> LENGTH: 21
<212> TYPE: DNA
<213> ORGANISM: Homo sapiens

<400> SEQUENCE: 59
aaatgtgtca agaatgacat g                                              21

<210> SEQ ID NO 60
<211> LENGTH: 21
<212> TYPE: DNA
<213> ORGANISM: Homo sapiens

<400> SEQUENCE: 60
aagaatgaca tggctgtcaa t                                              21

<210> SEQ ID NO 61
<211> LENGTH: 21
<212> TYPE: DNA
<213> ORGANISM: Homo sapiens

<400> SEQUENCE: 61
aatgacatgg ctgtcaatga g                                              21

<210> SEQ ID NO 62
<211> LENGTH: 21
<212> TYPE: DNA
<213> ORGANISM: Homo sapiens

<400> SEQUENCE: 62
aatgagacaa ccaactactc a                                              21

<210> SEQ ID NO 63
<211> LENGTH: 21
<212> TYPE: DNA
<213> ORGANISM: Homo sapiens

<400> SEQUENCE: 63
aaccaactac tcatctcaca g                                              21

<210> SEQ ID NO 64
<211> LENGTH: 21
<212> TYPE: DNA
<213> ORGANISM: Homo sapiens

<400> SEQUENCE: 64
aactactcat ctcacagaaa a                                              21

<210> SEQ ID NO 65
<211> LENGTH: 21
<212> TYPE: DNA
<213> ORGANISM: Homo sapiens

<400> SEQUENCE: 65
aaaaccagat atctacataa a                                              21

<210> SEQ ID NO 66
<211> LENGTH: 21
<212> TYPE: DNA
<213> ORGANISM: Homo sapiens

<400> SEQUENCE: 66
aaccagatat ctacataaat a                                              21
```

```
<210> SEQ ID NO 67
<211> LENGTH: 21
<212> TYPE: DNA
<213> ORGANISM: Homo sapiens

<400> SEQUENCE: 67
aaataagcga ggcacttctg a                                              21

<210> SEQ ID NO 68
<211> LENGTH: 21
<212> TYPE: DNA
<213> ORGANISM: Homo sapiens

<400> SEQUENCE: 68
aagcgaggca cttctgaccc c                                              21

<210> SEQ ID NO 69
<211> LENGTH: 21
<212> TYPE: DNA
<213> ORGANISM: Homo sapiens

<400> SEQUENCE: 69
aatggatctg actcaggcca c                                              21

<210> SEQ ID NO 70
<211> LENGTH: 21
<212> TYPE: DNA
<213> ORGANISM: Homo sapiens

<400> SEQUENCE: 70
aaaacttctg acaacccgga t                                              21

<210> SEQ ID NO 71
<211> LENGTH: 21
<212> TYPE: DNA
<213> ORGANISM: Homo sapiens

<400> SEQUENCE: 71
aacttctgac aacccggatt t                                              21

<210> SEQ ID NO 72
<211> LENGTH: 21
<212> TYPE: DNA
<213> ORGANISM: Homo sapiens

<400> SEQUENCE: 72
aacccggatt ttaactacac c                                              21

<210> SEQ ID NO 73
<211> LENGTH: 21
<212> TYPE: DNA
<213> ORGANISM: Homo sapiens

<400> SEQUENCE: 73
aacccggatt ttaactacac c                                              21

<210> SEQ ID NO 74
<211> LENGTH: 21
<212> TYPE: DNA
<213> ORGANISM: Homo sapiens

<400> SEQUENCE: 74
aacgcctcta ccagcagacc c                                              21
```

```
<210> SEQ ID NO 75
<211> LENGTH: 21
<212> TYPE: DNA
<213> ORGANISM: Homo sapiens

<400> SEQUENCE: 75
aaaatctata tgatcttttt t                                              21

<210> SEQ ID NO 76
<211> LENGTH: 21
<212> TYPE: DNA
<213> ORGANISM: Homo sapiens

<400> SEQUENCE: 76
aatctatatg atctttttg t                                               21

<210> SEQ ID NO 77
<211> LENGTH: 21
<212> TYPE: DNA
<213> ORGANISM: Homo sapiens

<400> SEQUENCE: 77
aatcttcctg ggatctttct a                                              21

<210> SEQ ID NO 78
<211> LENGTH: 21
<212> TYPE: DNA
<213> ORGANISM: Homo sapiens

<400> SEQUENCE: 78
aacttgatct tggctgtagt c                                              21

<210> SEQ ID NO 79
<211> LENGTH: 21
<212> TYPE: DNA
<213> ORGANISM: Homo sapiens

<400> SEQUENCE: 79
aaccaggcaa ccactgatga a                                              21

<210> SEQ ID NO 80
<211> LENGTH: 21
<212> TYPE: DNA
<213> ORGANISM: Homo sapiens

<400> SEQUENCE: 80
aaccactgat gaaattgaag c                                              21

<210> SEQ ID NO 81
<211> LENGTH: 21
<212> TYPE: DNA
<213> ORGANISM: Homo sapiens

<400> SEQUENCE: 81
aaattgaagc aaaggagaag a                                              21

<210> SEQ ID NO 82
<211> LENGTH: 21
<212> TYPE: DNA
<213> ORGANISM: Homo sapiens

<400> SEQUENCE: 82
aagcaaagga gaagaagttc c                                              21
```

```
<210> SEQ ID NO 83
<211> LENGTH: 21
<212> TYPE: DNA
<213> ORGANISM: Homo sapiens

<400> SEQUENCE: 83
aaaggagaag aagttccagg a                                              21

<210> SEQ ID NO 84
<211> LENGTH: 21
<212> TYPE: DNA
<213> ORGANISM: Homo sapiens

<400> SEQUENCE: 84
aagaagttcc aggaggccct c                                              21

<210> SEQ ID NO 85
<211> LENGTH: 21
<212> TYPE: DNA
<213> ORGANISM: Homo sapiens

<400> SEQUENCE: 85
aagttccagg aggccctcga g                                              21

<210> SEQ ID NO 86
<211> LENGTH: 21
<212> TYPE: DNA
<213> ORGANISM: Homo sapiens

<400> SEQUENCE: 86
aaggagcagg aggtgctagc a                                              21

<210> SEQ ID NO 87
<211> LENGTH: 21
<212> TYPE: DNA
<213> ORGANISM: Homo sapiens

<400> SEQUENCE: 87
aacctctctc cactcccaca a                                              21

<210> SEQ ID NO 88
<211> LENGTH: 21
<212> TYPE: DNA
<213> ORGANISM: Homo sapiens

<400> SEQUENCE: 88
aatggatcac ctttaacctc c                                              21

<210> SEQ ID NO 89
<211> LENGTH: 21
<212> TYPE: DNA
<213> ORGANISM: Homo sapiens

<400> SEQUENCE: 89
aacctccaaa aatgccagtg a                                              21

<210> SEQ ID NO 90
<211> LENGTH: 21
<212> TYPE: DNA
<213> ORGANISM: Homo sapiens

<400> SEQUENCE: 90
aaaaatgcca gtgagagaag g                                              21
```

-continued

```
<210> SEQ ID NO 91
<211> LENGTH: 21
<212> TYPE: DNA
<213> ORGANISM: Homo sapiens

<400> SEQUENCE: 91
aaatgccagt gagagaaggc a                                              21

<210> SEQ ID NO 92
<211> LENGTH: 21
<212> TYPE: DNA
<213> ORGANISM: Homo sapiens

<400> SEQUENCE: 92
aaggcataga ataaagccaa g                                              21

<210> SEQ ID NO 93
<211> LENGTH: 21
<212> TYPE: DNA
<213> ORGANISM: Homo sapiens

<400> SEQUENCE: 93
aataaagcca agagtgtcag a                                              21

<210> SEQ ID NO 94
<211> LENGTH: 21
<212> TYPE: DNA
<213> ORGANISM: Homo sapiens

<400> SEQUENCE: 94
aaagccaaga gtgtcagagg g                                              21

<210> SEQ ID NO 95
<211> LENGTH: 21
<212> TYPE: DNA
<213> ORGANISM: Homo sapiens

<400> SEQUENCE: 95
aagagtgtca gagggctcca c                                              21

<210> SEQ ID NO 96
<211> LENGTH: 21
<212> TYPE: DNA
<213> ORGANISM: Homo sapiens

<400> SEQUENCE: 96
aagacaacaa atcaccccgc t                                              21

<210> SEQ ID NO 97
<211> LENGTH: 21
<212> TYPE: DNA
<213> ORGANISM: Homo sapiens

<400> SEQUENCE: 97
aacaaatcac cccgctctga t                                              21

<210> SEQ ID NO 98
<211> LENGTH: 21
<212> TYPE: DNA
<213> ORGANISM: Homo sapiens

<400> SEQUENCE: 98
aaatcacccc gctctgatcc t                                              21
```

```
<210> SEQ ID NO 99
<211> LENGTH: 21
<212> TYPE: DNA
<213> ORGANISM: Homo sapiens

<400> SEQUENCE: 99
aaccagcgca ggatgtctttt t                                           21

<210> SEQ ID NO 100
<211> LENGTH: 21
<212> TYPE: DNA
<213> ORGANISM: Homo sapiens

<400> SEQUENCE: 100
aaaacgccgg gctagtcatg g                                            21

<210> SEQ ID NO 101
<211> LENGTH: 21
<212> TYPE: DNA
<213> ORGANISM: Homo sapiens

<400> SEQUENCE: 101
aacgccgggc tagtcatggc a                                            21

<210> SEQ ID NO 102
<211> LENGTH: 21
<212> TYPE: DNA
<213> ORGANISM: Homo sapiens

<400> SEQUENCE: 102
aaagccatcg gggctctctg c                                            21

<210> SEQ ID NO 103
<211> LENGTH: 21
<212> TYPE: DNA
<213> ORGANISM: Homo sapiens

<400> SEQUENCE: 103 aaggcccct ccctagaagc c                                             21

<210> SEQ ID NO 104
<211> LENGTH: 21
<212> TYPE: DNA
<213> ORGANISM: Homo sapiens

<400> SEQUENCE: 104
aagccctctt cctcaaccca g                                            21

<210> SEQ ID NO 105
<211> LENGTH: 21
<212> TYPE: DNA
<213> ORGANISM: Homo sapiens

<400> SEQUENCE: 105
aacccagcaa ccctgactcc a                                            21

<210> SEQ ID NO 106
<211> LENGTH: 21
<212> TYPE: DNA
<213> ORGANISM: Homo sapiens

<400> SEQUENCE: 106
aaccctgact ccaggcatgg a                                            21
```

-continued

<210> SEQ ID NO 107
<211> LENGTH: 21
<212> TYPE: DNA
<213> ORGANISM: Homo sapiens

<400> SEQUENCE: 107
aagatgaaca ccaaccgccg c                                            21

<210> SEQ ID NO 108
<211> LENGTH: 21
<212> TYPE: DNA
<213> ORGANISM: Homo sapiens

<400> SEQUENCE: 108
aacaccaacc gccgcccact a                                            21

<210> SEQ ID NO 109
<211> LENGTH: 21
<212> TYPE: DNA
<213> ORGANISM: Homo sapiens

<400> SEQUENCE: 109
aaccgccgcc cactagtgag c                                            21

<210> SEQ ID NO 110
<211> LENGTH: 21
<212> TYPE: DNA
<213> ORGANISM: Homo sapiens

<400> SEQUENCE: 110
aaaagaagac tttcttgtca g                                            21

<210> SEQ ID NO 111
<211> LENGTH: 21
<212> TYPE: DNA
<213> ORGANISM: Homo sapiens

<400> SEQUENCE: 111
aagaagactt tcttgtcagc a                                            21

<210> SEQ ID NO 112
<211> LENGTH: 21
<212> TYPE: DNA
<213> ORGANISM: Homo sapiens

<400> SEQUENCE: 112
aagactttct tgtcagcaga a                                            21

<210> SEQ ID NO 113
<211> LENGTH: 21
<212> TYPE: DNA
<213> ORGANISM: Homo sapiens

<400> SEQUENCE: 113
aatacttaga tgaacctttc c                                            21

<210> SEQ ID NO 114
<211> LENGTH: 21
<212> TYPE: DNA
<213> ORGANISM: Homo sapiens

<400> SEQUENCE: 114
aacctttccg ggcccaaagg g                                            21

-continued

<210> SEQ ID NO 115
<211> LENGTH: 21
<212> TYPE: DNA
<213> ORGANISM: Homo sapiens

<400> SEQUENCE: 115
aaagggcaat gagtgttgtc a                                              21

<210> SEQ ID NO 116
<211> LENGTH: 21
<212> TYPE: DNA
<213> ORGANISM: Homo sapiens

<400> SEQUENCE: 116
aatgagtgtt gtcagtatca t                                              21

<210> SEQ ID NO 117
<211> LENGTH: 21
<212> TYPE: DNA
<213> ORGANISM: Homo sapiens

<400> SEQUENCE: 117
aacctccgtc cttgaggaac t                                              21

<210> SEQ ID NO 118
<211> LENGTH: 21
<212> TYPE: DNA
<213> ORGANISM: Homo sapiens

<400> SEQUENCE: 118
aactcgagga gtctgaacag a                                              21

<210> SEQ ID NO 119
<211> LENGTH: 21
<212> TYPE: DNA
<213> ORGANISM: Homo sapiens

<400> SEQUENCE: 119
aactcgagga gtctgaacag a                                              21

<210> SEQ ID NO 120
<211> LENGTH: 21
<212> TYPE: DNA
<213> ORGANISM: Homo sapiens

<400> SEQUENCE: 120
aagtgcccac cctgcttgac c                                              21

<210> SEQ ID NO 121
<211> LENGTH: 21
<212> TYPE: DNA
<213> ORGANISM: Homo sapiens

<400> SEQUENCE: 121
aagtatctga tctgggattg c                                              21

<210> SEQ ID NO 122
<211> LENGTH: 21
<212> TYPE: DNA
<213> ORGANISM: Homo sapiens

<400> SEQUENCE: 122
aagtatctga tctgggattg c                                              21

-continued

```
<210> SEQ ID NO 123
<211> LENGTH: 21
<212> TYPE: DNA
<213> ORGANISM: Homo sapiens

<400> SEQUENCE: 123
aagacaattc tctttgggct t                                              21

<210> SEQ ID NO 124
<211> LENGTH: 21
<212> TYPE: DNA
<213> ORGANISM: Homo sapiens

<400> SEQUENCE: 124
aattctcttt gggcttgtga c                                              21

<210> SEQ ID NO 125
<211> LENGTH: 21
<212> TYPE: DNA
<213> ORGANISM: Homo sapiens

<400> SEQUENCE: 125
aacaccatct tcatggccat g                                              21

<210> SEQ ID NO 126
<211> LENGTH: 21
<212> TYPE: DNA
<213> ORGANISM: Homo sapiens

<400> SEQUENCE: 126
aagccatgct ccagataggc a                                              21

<210> SEQ ID NO 127
<211> LENGTH: 21
<212> TYPE: DNA
<213> ORGANISM: Homo sapiens

<400> SEQUENCE: 127
aacatcgtct ttaccatatt t                                              21

<210> SEQ ID NO 128
<211> LENGTH: 21
<212> TYPE: DNA
<213> ORGANISM: Homo sapiens

<400> SEQUENCE: 128
aaatggtctt caaaatcatt g                                              21

<210> SEQ ID NO 129
<211> LENGTH: 21
<212> TYPE: DNA
<213> ORGANISM: Homo sapiens

<400> SEQUENCE: 129
aaaatcattg ccttcgaccc a                                              21

<210> SEQ ID NO 130
<211> LENGTH: 21
<212> TYPE: DNA
<213> ORGANISM: Homo sapiens

<400> SEQUENCE: 130
aatcattgcc ttcgacccat a                                              21
```

```
<210> SEQ ID NO 131
<211> LENGTH: 21
<212> TYPE: DNA
<213> ORGANISM: Homo sapiens

<400> SEQUENCE: 131
aagaagtgga atatctttga c                                              21

<210> SEQ ID NO 132
<211> LENGTH: 21
<212> TYPE: DNA
<213> ORGANISM: Homo sapiens

<400> SEQUENCE: 132
aagtggaata tctttgactg c                                              21

<210> SEQ ID NO 133
<211> LENGTH: 21
<212> TYPE: DNA
<213> ORGANISM: Homo sapiens

<400> SEQUENCE: 133
aatatctttg actgcatcat c                                              21

<210> SEQ ID NO 134
<211> LENGTH: 21
<212> TYPE: DNA
<213> ORGANISM: Homo sapiens

<400> SEQUENCE: 134
aagaagggaa gcctgtctgt g                                              21

<210> SEQ ID NO 135
<211> LENGTH: 21
<212> TYPE: DNA
<213> ORGANISM: Homo sapiens

<400> SEQUENCE: 135
aagggaagcc tgtctgtgct g                                              21

<210> SEQ ID NO 136
<211> LENGTH: 21
<212> TYPE: DNA
<213> ORGANISM: Homo sapiens

<400> SEQUENCE: 136
aagcctgtct gtgctgcgga g                                              21

<210> SEQ ID NO 137
<211> LENGTH: 21
<212> TYPE: DNA
<213> ORGANISM: Homo sapiens

<400> SEQUENCE: 137
aagctggcca atcctggcc c                                               21

<210> SEQ ID NO 138
<211> LENGTH: 21
<212> TYPE: DNA
<213> ORGANISM: Homo sapiens

<400> SEQUENCE: 138
aaatcctggc ccaccttaaa c                                              21
```

```
<210> SEQ ID NO 139
<211> LENGTH: 21
<212> TYPE: DNA
<213> ORGANISM: Homo sapiens

<400> SEQUENCE: 139
aaacacactc atcaagatca t                                      21

<210> SEQ ID NO 140
<211> LENGTH: 21
<212> TYPE: DNA
<213> ORGANISM: Homo sapiens

<400> SEQUENCE: 140
aagatcatcg gaaactcagt g                                      21

<210> SEQ ID NO 141
<211> LENGTH: 21
<212> TYPE: DNA
<213> ORGANISM: Homo sapiens

<400> SEQUENCE: 141
aaactcagtg ggggcactgg g                                      21

<210> SEQ ID NO 142
<211> LENGTH: 21
<212> TYPE: DNA
<213> ORGANISM: Homo sapiens

<400> SEQUENCE: 142
aacctcacca tcatcctggc c                                      21

<210> SEQ ID NO 143
<211> LENGTH: 21
<212> TYPE: DNA
<213> ORGANISM: Homo sapiens

<400> SEQUENCE: 143
aagcagctcc taggggaaaa c                                      21

<210> SEQ ID NO 144
<211> LENGTH: 21
<212> TYPE: DNA
<213> ORGANISM: Homo sapiens

<400> SEQUENCE: 144
aaaactaccg taacaaccga a                                      21

<210> SEQ ID NO 145
<211> LENGTH: 21
<212> TYPE: DNA
<213> ORGANISM: Homo sapiens

<400> SEQUENCE: 145
aactaccgta acaaccgaaa a                                      21

<210> SEQ ID NO 146
<211> LENGTH: 21
<212> TYPE: DNA
<213> ORGANISM: Homo sapiens

<400> SEQUENCE: 146
aacaaccgaa aaatatctc c                                       21
```

```
<210> SEQ ID NO 147
<211> LENGTH: 21
<212> TYPE: DNA
<213> ORGANISM: Homo sapiens

<400> SEQUENCE: 147
aaccgaaaaa atatctccgc g                                              21

<210> SEQ ID NO 148
<211> LENGTH: 21
<212> TYPE: DNA
<213> ORGANISM: Homo sapiens

<400> SEQUENCE: 148
aaaaaatatc tccgcgcccc a                                              21

<210> SEQ ID NO 149
<211> LENGTH: 21
<212> TYPE: DNA
<213> ORGANISM: Homo sapiens

<400> SEQUENCE: 149
aaaatatctc cgcgccccat g                                              21

<210> SEQ ID NO 150
<211> LENGTH: 21
<212> TYPE: DNA
<213> ORGANISM: Homo sapiens

<400> SEQUENCE: 150
aatatctccg cgccccatga a                                              21

<210> SEQ ID NO 151
<211> LENGTH: 21
<212> TYPE: DNA
<213> ORGANISM: Homo sapiens

<400> SEQUENCE: 151
aagactggcc ccgctggcac a                                              21

<210> SEQ ID NO 152
<211> LENGTH: 21
<212> TYPE: DNA
<213> ORGANISM: Homo sapiens

<400> SEQUENCE: 152
aacatgtggg cctgcatgga a                                              21

<210> SEQ ID NO 153
<211> LENGTH: 21
<212> TYPE: DNA
<213> ORGANISM: Homo sapiens

<400> SEQUENCE: 153
aagttggcca aaaatccata t                                              21

<210> SEQ ID NO 154
<211> LENGTH: 21
<212> TYPE: DNA
<213> ORGANISM: Homo sapiens

<400> SEQUENCE: 154
aaaaatccat atgcctcatc c                                              21
```

```
<210> SEQ ID NO 155
<211> LENGTH: 21
<212> TYPE: DNA
<213> ORGANISM: Homo sapiens

<400> SEQUENCE: 155
aaatccatat gcctcatcct t                                              21

<210> SEQ ID NO 156
<211> LENGTH: 21
<212> TYPE: DNA
<213> ORGANISM: Homo sapiens

<400> SEQUENCE: 156
aacctggtgg tgcttaacct g                                              21

<210> SEQ ID NO 157
<211> LENGTH: 21
<212> TYPE: DNA
<213> ORGANISM: Homo sapiens

<400> SEQUENCE: 157
aacctgttca tcgccctgct a                                              21

<210> SEQ ID NO 158
<211> LENGTH: 21
<212> TYPE: DNA
<213> ORGANISM: Homo sapiens

<400> SEQUENCE: 158
aactctttca gtgctgacaa c                                              21

<210> SEQ ID NO 159
<211> LENGTH: 21
<212> TYPE: DNA
<213> ORGANISM: Homo sapiens

<400> SEQUENCE: 159
aacctcacag ccccggagga c                                              21

<210> SEQ ID NO 160
<211> LENGTH: 21
<212> TYPE: DNA
<213> ORGANISM: Homo sapiens

<400> SEQUENCE: 160
aacaacctgc aggtggccct g                                              21

<210> SEQ ID NO 161
<211> LENGTH: 21
<212> TYPE: DNA
<213> ORGANISM: Homo sapiens

<400> SEQUENCE: 161
aacctgcagg tggccctggc a                                              21

<210> SEQ ID NO 162
<211> LENGTH: 21
<212> TYPE: DNA
<213> ORGANISM: Homo sapiens

<400> SEQUENCE: 162
aaacaggctc tttgcagctt c                                              21
```

```
<210> SEQ ID NO 163
<211> LENGTH: 21
<212> TYPE: DNA
<213> ORGANISM: Homo sapiens

<400> SEQUENCE: 163
aaggcagagc ctgagctggt g                                              21

<210> SEQ ID NO 164
<211> LENGTH: 21
<212> TYPE: DNA
<213> ORGANISM: Homo sapiens

<400> SEQUENCE: 164
aaactcccac tctccagctc c                                              21

<210> SEQ ID NO 165
<211> LENGTH: 21
<212> TYPE: DNA
<213> ORGANISM: Homo sapiens

<400> SEQUENCE: 165
aaggctgaga accacattgc t                                              21

<210> SEQ ID NO 166
<211> LENGTH: 21
<212> TYPE: DNA
<213> ORGANISM: Homo sapiens

<400> SEQUENCE: 166
aaccacattg ctgccaacac t                                              21

<210> SEQ ID NO 167
<211> LENGTH: 21
<212> TYPE: DNA
<213> ORGANISM: Homo sapiens

<400> SEQUENCE: 167
aacactgcca gggggagctc t                                              21

<210> SEQ ID NO 168
<211> LENGTH: 21
<212> TYPE: DNA
<213> ORGANISM: Homo sapiens

<400> SEQUENCE: 168
aagctcccag aggccccagg g                                              21

<210> SEQ ID NO 169
<211> LENGTH: 21
<212> TYPE: DNA
<213> ORGANISM: Homo sapiens

<400> SEQUENCE: 169
aatccgactg tgtgggtctc t                                              21

<210> SEQ ID NO 170
<211> LENGTH: 21
<212> TYPE: DNA
<213> ORGANISM: Homo sapiens

<400> SEQUENCE: 170
aatctgatct tgatgacttg g                                              21
```

<210> SEQ ID NO 171
<211> LENGTH: 21
<212> TYPE: DNA
<213> ORGANISM: Homo sapiens

<400> SEQUENCE: 171
aagatgctca gagcttccag c                                              21

<210> SEQ ID NO 172
<211> LENGTH: 21
<212> TYPE: DNA
<213> ORGANISM: Homo sapiens

<400> SEQUENCE: 172
aagtgatccc caaaggacag c                                              21

<210> SEQ ID NO 173
<211> LENGTH: 21
<212> TYPE: DNA
<213> ORGANISM: Homo sapiens

<400> SEQUENCE: 173
aaaggacagc aggagcagct g                                              21

<210> SEQ ID NO 174
<211> LENGTH: 21
<212> TYPE: DNA
<213> ORGANISM: Homo sapiens

<400> SEQUENCE: 174
aagtcgagag gtgtggggac c                                              21

<210> SEQ ID NO 175
<211> LENGTH: 21
<212> TYPE: DNA
<213> ORGANISM: Homo sapiens

<400> SEQUENCE: 175
aacatcttct gaggacctgg c                                              21

<210> SEQ ID NO 176
<211> LENGTH: 21
<212> TYPE: DNA
<213> ORGANISM: Homo sapiens

<400> SEQUENCE: 176
aaagatgagt ctgttcctca g                                              21

<210> SEQ ID NO 177
<211> LENGTH: 21
<212> TYPE: DNA
<213> ORGANISM: Homo sapiens

<400> SEQUENCE: 177
aagctcctct gagggcagca c                                              21

<210> SEQ ID NO 178
<211> LENGTH: 21
<212> TYPE: DNA
<213> ORGANISM: Homo sapiens

<400> SEQUENCE: 178
aaatcctgag gaagatccct g                                              21

```
<210> SEQ ID NO 179
<211> LENGTH: 21
<212> TYPE: DNA
<213> ORGANISM: Homo sapiens

<400> SEQUENCE: 179
aagatccctg agctggcaga t                                              21

<210> SEQ ID NO 180
<211> LENGTH: 21
<212> TYPE: DNA
<213> ORGANISM: Homo sapiens

<400> SEQUENCE: 180
aagaaccaga tgactgcttc a                                              21

<210> SEQ ID NO 181
<211> LENGTH: 21
<212> TYPE: DNA
<213> ORGANISM: Homo sapiens

<400> SEQUENCE: 181
aaccagatga ctgcttcaca g                                              21

<210> SEQ ID NO 182
<211> LENGTH: 21
<212> TYPE: DNA
<213> ORGANISM: Homo sapiens

<400> SEQUENCE: 182
aaggatgcat tcgccactgt c                                              21

<210> SEQ ID NO 183
<211> LENGTH: 21
<212> TYPE: DNA
<213> ORGANISM: Homo sapiens

<400> SEQUENCE: 183
aaactggata ccaccaagag t                                              21

<210> SEQ ID NO 184
<211> LENGTH: 21
<212> TYPE: DNA
<213> ORGANISM: Homo sapiens

<400> SEQUENCE: 184
aagagtccat gggatgtggg c                                              21

<210> SEQ ID NO 185
<211> LENGTH: 21
<212> TYPE: DNA
<213> ORGANISM: Homo sapiens

<400> SEQUENCE: 185
aagacttgct accgtatcgt g                                              21

<210> SEQ ID NO 186
<211> LENGTH: 21
<212> TYPE: DNA
<213> ORGANISM: Homo sapiens

<400> SEQUENCE: 186
aagactatta cctggaccag a                                              21
```

```
<210> SEQ ID NO 187
<211> LENGTH: 21
<212> TYPE: DNA
<213> ORGANISM: Homo sapiens

<400> SEQUENCE: 187
aagcccacgg tgaaagcttt g                                              21

<210> SEQ ID NO 188
<211> LENGTH: 21
<212> TYPE: DNA
<213> ORGANISM: Homo sapiens

<400> SEQUENCE: 188
aaagctttgc tggagtacac t                                              21

<210> SEQ ID NO 189
<211> LENGTH: 21
<212> TYPE: DNA
<213> ORGANISM: Homo sapiens

<400> SEQUENCE: 189
aagtgggtgg cctatggctt c                                              21

<210> SEQ ID NO 190
<211> LENGTH: 21
<212> TYPE: DNA
<213> ORGANISM: Homo sapiens

<400> SEQUENCE: 190
aaaaagtact tcaccaatgc c                                              21

<210> SEQ ID NO 191
<211> LENGTH: 21
<212> TYPE: DNA
<213> ORGANISM: Homo sapiens

<400> SEQUENCE: 191
aaagtacttc accaatgcct g                                              21

<210> SEQ ID NO 192
<211> LENGTH: 21
<212> TYPE: DNA
<213> ORGANISM: Homo sapiens

<400> SEQUENCE: 192
aatgcctggt gctggctgga c                                              21

<210> SEQ ID NO 193
<211> LENGTH: 21
<212> TYPE: DNA
<213> ORGANISM: Homo sapiens

<400> SEQUENCE: 193
aatatctcac tgataagtct c                                              21

<210> SEQ ID NO 194
<211> LENGTH: 21
<212> TYPE: DNA
<213> ORGANISM: Homo sapiens

<400> SEQUENCE: 194
aagtctcaca gcgaagattc t                                              21
```

<210> SEQ ID NO 195
<211> LENGTH: 21
<212> TYPE: DNA
<213> ORGANISM: Homo sapiens

<400> SEQUENCE: 195
aagattctgg aatattctga a        21

<210> SEQ ID NO 196
<211> LENGTH: 21
<212> TYPE: DNA
<213> ORGANISM: Homo sapiens

<400> SEQUENCE: 196
aatattctga agtggctccc a        21

<210> SEQ ID NO 197
<211> LENGTH: 21
<212> TYPE: DNA
<213> ORGANISM: Homo sapiens

<400> SEQUENCE: 197
aagtggctcc catcaaagcc c        21

<210> SEQ ID NO 198
<211> LENGTH: 21
<212> TYPE: DNA
<213> ORGANISM: Homo sapiens

<400> SEQUENCE: 198
aaagcccttc gaacccttcg c        21

<210> SEQ ID NO 199
<211> LENGTH: 21
<212> TYPE: DNA
<213> ORGANISM: Homo sapiens

<400> SEQUENCE: 199
aacccttcgc gctctgcggc c        21

<210> SEQ ID NO 200
<211> LENGTH: 21
<212> TYPE: DNA
<213> ORGANISM: Homo sapiens

<400> SEQUENCE: 200
aaggcatgcg ggtggtggtg g        21

<210> SEQ ID NO 201
<211> LENGTH: 21
<212> TYPE: DNA
<213> ORGANISM: Homo sapiens

<400> SEQUENCE: 201
aatgtcctcc tcgtctgcct c        21

<210> SEQ ID NO 202
<211> LENGTH: 21
<212> TYPE: DNA
<213> ORGANISM: Homo sapiens

<400> SEQUENCE: 202
aacctcttcg cagggaagtt t        21

```
<210> SEQ ID NO 203
<211> LENGTH: 21
<212> TYPE: DNA
<213> ORGANISM: Homo sapiens

<400> SEQUENCE: 203
aagttttgga ggtgcatcaa c                                              21

<210> SEQ ID NO 204
<211> LENGTH: 21
<212> TYPE: DNA
<213> ORGANISM: Homo sapiens

<400> SEQUENCE: 204
aactataccg atggagagtt t                                              21

<210> SEQ ID NO 205
<211> LENGTH: 21
<212> TYPE: DNA
<213> ORGANISM: Homo sapiens

<400> SEQUENCE: 205
aataacaagt ctgactgcaa g                                              21

<210> SEQ ID NO 206
<211> LENGTH: 21
<212> TYPE: DNA
<213> ORGANISM: Homo sapiens

<400> SEQUENCE: 206
aacaagtctg actgcaagat t                                              21

<210> SEQ ID NO 207
<211> LENGTH: 21
<212> TYPE: DNA
<213> ORGANISM: Homo sapiens

<400> SEQUENCE: 207
aagtctgact gcaagattca a                                              21

<210> SEQ ID NO 208
<211> LENGTH: 21
<212> TYPE: DNA
<213> ORGANISM: Homo sapiens

<400> SEQUENCE: 208
aagattcaaa actccactgg c                                              21

<210> SEQ ID NO 209
<211> LENGTH: 21
<212> TYPE: DNA
<213> ORGANISM: Homo sapiens

<400> SEQUENCE: 209
aaaactccac tggcagcttc t                                              21

<210> SEQ ID NO 210
<211> LENGTH: 21
<212> TYPE: DNA
<213> ORGANISM: Homo sapiens

<400> SEQUENCE: 210
aactccactg gcagcttctt c                                              21
```

```
<210> SEQ ID NO 211
<211> LENGTH: 21
<212> TYPE: DNA
<213> ORGANISM: Homo sapiens

<400> SEQUENCE: 211
aatgtgaaag tcaactttga t                                             21

<210> SEQ ID NO 212
<211> LENGTH: 21
<212> TYPE: DNA
<213> ORGANISM: Homo sapiens

<400> SEQUENCE: 212
aaagtcaact ttgataatgt t                                             21

<210> SEQ ID NO 213
<211> LENGTH: 21
<212> TYPE: DNA
<213> ORGANISM: Homo sapiens

<400> SEQUENCE: 213
aactttgata atgttgcaat g                                             21

<210> SEQ ID NO 214
<211> LENGTH: 21
<212> TYPE: DNA
<213> ORGANISM: Homo sapiens

<400> SEQUENCE: 214
aatgttgcaa tgggttacct t                                             21

<210> SEQ ID NO 215
<211> LENGTH: 21
<212> TYPE: DNA
<213> ORGANISM: Homo sapiens

<400> SEQUENCE: 215
aatgggttac cttgcacttc t                                             21

<210> SEQ ID NO 216
<211> LENGTH: 21
<212> TYPE: DNA
<213> ORGANISM: Homo sapiens

<400> SEQUENCE: 216
aacctttaaa ggctggatgg a                                             21

<210> SEQ ID NO 217
<211> LENGTH: 21
<212> TYPE: DNA
<213> ORGANISM: Homo sapiens

<400> SEQUENCE: 217
aaaggctgga tggacattat g                                             21

<210> SEQ ID NO 218
<211> LENGTH: 21
<212> TYPE: DNA
<213> ORGANISM: Homo sapiens

<400> SEQUENCE: 218
aacatgcaac ccaagtggga g                                             21
```

```
<210> SEQ ID NO 219
<211> LENGTH: 21
<212> TYPE: DNA
<213> ORGANISM: Homo sapiens

<400> SEQUENCE: 219
aacccaagtg ggaggacaac g                                              21

<210> SEQ ID NO 220
<211> LENGTH: 21
<212> TYPE: DNA
<213> ORGANISM: Homo sapiens

<400> SEQUENCE: 220
aagtgggagg acaacgtgta c                                              21

<210> SEQ ID NO 221
<211> LENGTH: 21
<212> TYPE: DNA
<213> ORGANISM: Homo sapiens

<400> SEQUENCE: 221
aacgtgtaca tgtatttgta c                                              21

<210> SEQ ID NO 222
<211> LENGTH: 21
<212> TYPE: DNA
<213> ORGANISM: Homo sapiens

<400> SEQUENCE: 222
aatctctttg ttggggtcat a                                              21

<210> SEQ ID NO 223
<211> LENGTH: 21
<212> TYPE: DNA
<213> ORGANISM: Homo sapiens

<400> SEQUENCE: 223
aattgacaac ttcaatcaac a                                              21

<210> SEQ ID NO 224
<211> LENGTH: 21
<212> TYPE: DNA
<213> ORGANISM: Homo sapiens

<400> SEQUENCE: 224
aacttcaatc aacagaaaaa a                                              21

<210> SEQ ID NO 225
<211> LENGTH: 21
<212> TYPE: DNA
<213> ORGANISM: Homo sapiens

<400> SEQUENCE: 225
aatcaacaga aaaaaagtt a                                               21

<210> SEQ ID NO 226
<211> LENGTH: 21
<212> TYPE: DNA
<213> ORGANISM: Homo sapiens

<400> SEQUENCE: 226
aacagaaaaa aaagttaggg g                                              21
```

```
<210> SEQ ID NO 227
<211> LENGTH: 21
<212> TYPE: DNA
<213> ORGANISM: Homo sapiens

<400> SEQUENCE: 227
aaaaaaaagt taggggggcca g                                               21

<210> SEQ ID NO 228
<211> LENGTH: 21
<212> TYPE: DNA
<213> ORGANISM: Homo sapiens

<400> SEQUENCE: 228
aaaaaagtta gggggccagg a                                                21

<210> SEQ ID NO 229
<211> LENGTH: 21
<212> TYPE: DNA
<213> ORGANISM: Homo sapiens

<400> SEQUENCE: 229
aaaagttagg gggccaggac a                                                21

<210> SEQ ID NO 230
<211> LENGTH: 21
<212> TYPE: DNA
<213> ORGANISM: Homo sapiens

<400> SEQUENCE: 230
aagttagggg gccaggacat c                                                21

<210> SEQ ID NO 231
<211> LENGTH: 21
<212> TYPE: DNA
<213> ORGANISM: Homo sapiens

<400> SEQUENCE: 231
aagaaatact acaatgccat g                                                21

<210> SEQ ID NO 232
<211> LENGTH: 21
<212> TYPE: DNA
<213> ORGANISM: Homo sapiens

<400> SEQUENCE: 232
aaatactaca atgccatgaa g                                                21

<210> SEQ ID NO 233
<211> LENGTH: 21
<212> TYPE: DNA
<213> ORGANISM: Homo sapiens

<400> SEQUENCE: 233
aatgccatga agaagttggg c                                                21

<210> SEQ ID NO 234
<211> LENGTH: 21
<212> TYPE: DNA
<213> ORGANISM: Homo sapiens

<400> SEQUENCE: 234
aagaagttgg gctccaagaa g                                                21
```

```
<210> SEQ ID NO 235
<211> LENGTH: 21
<212> TYPE: DNA
<213> ORGANISM: Homo sapiens

<400> SEQUENCE: 235
aagttgggct ccaagaagcc c                                              21

<210> SEQ ID NO 236
<211> LENGTH: 21
<212> TYPE: DNA
<213> ORGANISM: Homo sapiens

<400> SEQUENCE: 236
aagaagcccc agaagcccat c                                              21

<210> SEQ ID NO 237
<211> LENGTH: 21
<212> TYPE: DNA
<213> ORGANISM: Homo sapiens

<400> SEQUENCE: 237
aagccccaga agcccatccc a                                              21

<210> SEQ ID NO 238
<211> LENGTH: 21
<212> TYPE: DNA
<213> ORGANISM: Homo sapiens

<400> SEQUENCE: 238
aagcccatcc cacggcccct g                                              21

<210> SEQ ID NO 239
<211> LENGTH: 21
<212> TYPE: DNA
<213> ORGANISM: Homo sapiens

<400> SEQUENCE: 239
aacaagttcc agggttttgt c                                              21

<210> SEQ ID NO 240
<211> LENGTH: 21
<212> TYPE: DNA
<213> ORGANISM: Homo sapiens

<400> SEQUENCE: 240
aagttccagg gttttgtctt t                                              21

<210> SEQ ID NO 241
<211> LENGTH: 21
<212> TYPE: DNA
<213> ORGANISM: Homo sapiens

<400> SEQUENCE: 241
aagcttttga catcaccatc a                                              21

<210> SEQ ID NO 242
<211> LENGTH: 21
<212> TYPE: DNA
<213> ORGANISM: Homo sapiens

<400> SEQUENCE: 242
aacatgatca ccatgatggt g                                              21
```

```
<210> SEQ ID NO 243
<211> LENGTH: 21
<212> TYPE: DNA
<213> ORGANISM: Homo sapiens

<400> SEQUENCE: 243
aaagtgaaga aaagacgaaa a                                              21

<210> SEQ ID NO 244
<211> LENGTH: 21
<212> TYPE: DNA
<213> ORGANISM: Homo sapiens

<400> SEQUENCE: 244
aagaaaagac gaaaattctg g                                              21

<210> SEQ ID NO 245
<211> LENGTH: 21
<212> TYPE: DNA
<213> ORGANISM: Homo sapiens

<400> SEQUENCE: 245
aaaagacgaa aattctgggc a                                              21

<210> SEQ ID NO 246
<211> LENGTH: 21
<212> TYPE: DNA
<213> ORGANISM: Homo sapiens

<400> SEQUENCE: 246
aagacgaaaa ttctgggcaa a                                              21

<210> SEQ ID NO 247
<211> LENGTH: 21
<212> TYPE: DNA
<213> ORGANISM: Homo sapiens

<400> SEQUENCE: 247
aaaattctgg gcaaaatcaa c                                              21

<210> SEQ ID NO 248
<211> LENGTH: 21
<212> TYPE: DNA
<213> ORGANISM: Homo sapiens

<400> SEQUENCE: 248
aattctgggc aaaatcaacc a                                              21

<210> SEQ ID NO 249
<211> LENGTH: 21
<212> TYPE: DNA
<213> ORGANISM: Homo sapiens

<400> SEQUENCE: 249
aaaatcaacc agttctttgt g                                              21

<210> SEQ ID NO 250
<211> LENGTH: 21
<212> TYPE: DNA
<213> ORGANISM: Homo sapiens

<400> SEQUENCE: 250
aatcaaccag ttctttgtgg c                                              21
```

```
<210> SEQ ID NO 251
<211> LENGTH: 21
<212> TYPE: DNA
<213> ORGANISM: Homo sapiens

<400> SEQUENCE: 251
aaccagttct ttgtggccgt c                                              21

<210> SEQ ID NO 252
<211> LENGTH: 21
<212> TYPE: DNA
<213> ORGANISM: Homo sapiens

<400> SEQUENCE: 252
aatgtgtcat gaagatgttc g                                              21

<210> SEQ ID NO 253
<211> LENGTH: 21
<212> TYPE: DNA
<213> ORGANISM: Homo sapiens

<400> SEQUENCE: 253
aagatgttcg ctttgaggca g                                              21

<210> SEQ ID NO 254
<211> LENGTH: 21
<212> TYPE: DNA
<213> ORGANISM: Homo sapiens

<400> SEQUENCE: 254
aaatggctgg aatgtgtttg a                                              21

<210> SEQ ID NO 255
<211> LENGTH: 21
<212> TYPE: DNA
<213> ORGANISM: Homo sapiens

<400> SEQUENCE: 255
aatgtgtttg acttcattgt g                                              21

<210> SEQ ID NO 256
<211> LENGTH: 21
<212> TYPE: DNA
<213> ORGANISM: Homo sapiens

<400> SEQUENCE: 256
aattcttaag tcacttcaaa g                                              21

<210> SEQ ID NO 257
<211> LENGTH: 21
<212> TYPE: DNA
<213> ORGANISM: Homo sapiens

<400> SEQUENCE: 257
aagtcacttc aaagttactt c                                              21

<210> SEQ ID NO 258
<211> LENGTH: 21
<212> TYPE: DNA
<213> ORGANISM: Homo sapiens

<400> SEQUENCE: 258
aaagttactt ctccccaacg c                                              21
```

```
<210> SEQ ID NO 259
<211> LENGTH: 21
<212> TYPE: DNA
<213> ORGANISM: Homo sapiens

<400> SEQUENCE: 259
aacgctcttc agagtcatcc g                                              21

<210> SEQ ID NO 260
<211> LENGTH: 21
<212> TYPE: DNA
<213> ORGANISM: Homo sapiens

<400> SEQUENCE: 260
aattggccgc atcctcagac t                                              21

<210> SEQ ID NO 261
<211> LENGTH: 21
<212> TYPE: DNA
<213> ORGANISM: Homo sapiens

<400> SEQUENCE: 261
aaggggatcc gcacactgct c                                              21

<210> SEQ ID NO 262
<211> LENGTH: 21
<212> TYPE: DNA
<213> ORGANISM: Homo sapiens

<400> SEQUENCE: 262
aacatcgggc tgttgctatt c                                              21

<210> SEQ ID NO 263
<211> LENGTH: 21
<212> TYPE: DNA
<213> ORGANISM: Homo sapiens

<400> SEQUENCE: 263
aacttccaga ccttcgccaa c                                              21

<210> SEQ ID NO 264
<211> LENGTH: 21
<212> TYPE: DNA
<213> ORGANISM: Homo sapiens

<400> SEQUENCE: 264
aacagcatgc tgtgcctctt c                                              21

<210> SEQ ID NO 265
<211> LENGTH: 21
<212> TYPE: DNA
<213> ORGANISM: Homo sapiens

<400> SEQUENCE: 265
aacacagggc cccctactg t                                               21

<210> SEQ ID NO 266
<211> LENGTH: 21
<212> TYPE: DNA
<213> ORGANISM: Homo sapiens

<400> SEQUENCE: 266
aatctgccca acagcaatgg c                                              21
```

```
<210> SEQ ID NO 267
<211> LENGTH: 21
<212> TYPE: DNA
<213> ORGANISM: Homo sapiens

<400> SEQUENCE: 267
aacagcaatg gcaccagagg g                                    21

<210> SEQ ID NO 268
<211> LENGTH: 21
<212> TYPE: DNA
<213> ORGANISM: Homo sapiens

<400> SEQUENCE: 268
aatggcacca gagggactg t                                     21

<210> SEQ ID NO 269
<211> LENGTH: 21
<212> TYPE: DNA
<213> ORGANISM: Homo sapiens

<400> SEQUENCE: 269
aacatgtaca ttgcagtgat t                                    21

<210> SEQ ID NO 270
<211> LENGTH: 21
<212> TYPE: DNA
<213> ORGANISM: Homo sapiens

<400> SEQUENCE: 270
aacttcaatg tggccacgga g                                    21

<210> SEQ ID NO 271
<211> LENGTH: 21
<212> TYPE: DNA
<213> ORGANISM: Homo sapiens

<400> SEQUENCE: 271
aatgtggcca cggaggagag c                                    21

<210> SEQ ID NO 272
<211> LENGTH: 21
<212> TYPE: DNA
<213> ORGANISM: Homo sapiens

<400> SEQUENCE: 272
aagtttgacc cagaggccac t                                    21

<210> SEQ ID NO 273
<211> LENGTH: 21
<212> TYPE: DNA
<213> ORGANISM: Homo sapiens

<400> SEQUENCE: 273
aatcccaaaa cccaatcgaa a                                    21

<210> SEQ ID NO 274
<211> LENGTH: 21
<212> TYPE: DNA
<213> ORGANISM: Homo sapiens

<400> SEQUENCE: 274 aaacccaat cgaaatatac t                                     21
```

```
<210> SEQ ID NO 275
<211> LENGTH: 21
<212> TYPE: DNA
<213> ORGANISM: Homo sapiens

<400> SEQUENCE: 275
aacccaatcg aaatatactg a                                              21

<210> SEQ ID NO 276
<211> LENGTH: 21
<212> TYPE: DNA
<213> ORGANISM: Homo sapiens

<400> SEQUENCE: 276
aatcgaaata tactgatcca g                                              21

<210> SEQ ID NO 277
<211> LENGTH: 21
<212> TYPE: DNA
<213> ORGANISM: Homo sapiens

<400> SEQUENCE: 277
aaatatactg atccagatgg a                                              21

<210> SEQ ID NO 278
<211> LENGTH: 21
<212> TYPE: DNA
<213> ORGANISM: Homo sapiens

<400> SEQUENCE: 278
aagatccact gcttggacat c                                              21

<210> SEQ ID NO 279
<211> LENGTH: 21
<212> TYPE: DNA
<213> ORGANISM: Homo sapiens

<400> SEQUENCE: 279
aagaatgtcc taggagaatc c                                              21

<210> SEQ ID NO 280
<211> LENGTH: 21
<212> TYPE: DNA
<213> ORGANISM: Homo sapiens

<400> SEQUENCE: 280
aatgtcctag gagaatccgg g                                              21

<210> SEQ ID NO 281
<211> LENGTH: 21
<212> TYPE: DNA
<213> ORGANISM: Homo sapiens

<400> SEQUENCE: 281
aatccgggga gttggattct c                                              21

<210> SEQ ID NO 282
<211> LENGTH: 21
<212> TYPE: DNA
<213> ORGANISM: Homo sapiens

<400> SEQUENCE: 282
aaggcaaata tggaggagaa g                                              21
```

```
<210> SEQ ID NO 283
<211> LENGTH: 21
<212> TYPE: DNA
<213> ORGANISM: Homo sapiens

<400> SEQUENCE: 283
aaatatggag gagaagttta t                                            21

<210> SEQ ID NO 284
<211> LENGTH: 21
<212> TYPE: DNA
<213> ORGANISM: Homo sapiens

<400> SEQUENCE: 284
aagtttatgg caactaatct t                                            21

<210> SEQ ID NO 285
<211> LENGTH: 21
<212> TYPE: DNA
<213> ORGANISM: Homo sapiens

<400> SEQUENCE: 285
aactaatctt tcaaaatcat c                                            21

<210> SEQ ID NO 286
<211> LENGTH: 21
<212> TYPE: DNA
<213> ORGANISM: Homo sapiens

<400> SEQUENCE: 286
aatctttcaa aatcatccta t                                            21

<210> SEQ ID NO 287
<211> LENGTH: 21
<212> TYPE: DNA
<213> ORGANISM: Homo sapiens

<400> SEQUENCE: 287
aaaatcatcc tatgaaccaa t                                            21

<210> SEQ ID NO 288
<211> LENGTH: 21
<212> TYPE: DNA
<213> ORGANISM: Homo sapiens

<400> SEQUENCE: 288
aatcatccta tgaaccaata g                                            21

<210> SEQ ID NO 289
<211> LENGTH: 21
<212> TYPE: DNA
<213> ORGANISM: Homo sapiens

<400> SEQUENCE: 289
aaccaatagc aaccactctc c                                            21

<210> SEQ ID NO 290
<211> LENGTH: 21
<212> TYPE: DNA
<213> ORGANISM: Homo sapiens

<400> SEQUENCE: 290
aatagcaacc actctccgat g                                            21
```

<210> SEQ ID NO 291
<211> LENGTH: 21
<212> TYPE: DNA
<213> ORGANISM: Homo sapiens

<400> SEQUENCE: 291
aaccactctc cgatggaagc a        21

<210> SEQ ID NO 292
<211> LENGTH: 21
<212> TYPE: DNA
<213> ORGANISM: Homo sapiens

<400> SEQUENCE: 292
aagcaagaag acatttcagc c        21

<210> SEQ ID NO 293
<211> LENGTH: 21
<212> TYPE: DNA
<213> ORGANISM: Homo sapiens

<400> SEQUENCE: 293
aagaagacat ttcagccact g        21

<210> SEQ ID NO 294
<211> LENGTH: 21
<212> TYPE: DNA
<213> ORGANISM: Homo sapiens

<400> SEQUENCE: 294
aagacatttc agccactgtc a        21

<210> SEQ ID NO 295
<211> LENGTH: 21
<212> TYPE: DNA
<213> ORGANISM: Homo sapiens

<400> SEQUENCE: 295
aaaaggccta tcggagctat g        21

<210> SEQ ID NO 296
<211> LENGTH: 21
<212> TYPE: DNA
<213> ORGANISM: Homo sapiens

<400> SEQUENCE: 296
aaggcctatc ggagctatgt g        21

<210> SEQ ID NO 297
<211> LENGTH: 21
<212> TYPE: DNA
<213> ORGANISM: Homo sapiens

<400> SEQUENCE: 297
aacaccccat gtgtgcccag a        21

<210> SEQ ID NO 298
<211> LENGTH: 21
<212> TYPE: DNA
<213> ORGANISM: Homo sapiens

<400> SEQUENCE: 298
aaggttttgt tgcattcaca g        21

```
<210> SEQ ID NO 299
<211> LENGTH: 21
<212> TYPE: DNA
<213> ORGANISM: Homo sapiens

<400> SEQUENCE: 299
aaatgaaaat tgtgtactcc c                                      21

<210> SEQ ID NO 300
<211> LENGTH: 21
<212> TYPE: DNA
<213> ORGANISM: Homo sapiens

<400> SEQUENCE: 300
aaaattgtgt actcccagac a                                      21

<210> SEQ ID NO 301
<211> LENGTH: 21
<212> TYPE: DNA
<213> ORGANISM: Homo sapiens

<400> SEQUENCE: 301
aattgtgtac tcccagacaa a                                      21

<210> SEQ ID NO 302
<211> LENGTH: 21
<212> TYPE: DNA
<213> ORGANISM: Homo sapiens

<400> SEQUENCE: 302
aaatctgaaa ctgcttctgc c                                      21

<210> SEQ ID NO 303
<211> LENGTH: 21
<212> TYPE: DNA
<213> ORGANISM: Homo sapiens

<400> SEQUENCE: 303
aaactgcttc tgccacatca t                                      21

<210> SEQ ID NO 304
<211> LENGTH: 21
<212> TYPE: DNA
<213> ORGANISM: Homo sapiens

<400> SEQUENCE: 304
aacatgagga catctagctc a                                      21

<210> SEQ ID NO 305
<211> LENGTH: 21
<212> TYPE: DNA
<213> ORGANISM: Homo sapiens

<400> SEQUENCE: 305
aatacaaaat gaagatgaag c                                      21

<210> SEQ ID NO 306
<211> LENGTH: 21
<212> TYPE: DNA
<213> ORGANISM: Homo sapiens

<400> SEQUENCE: 306
aaaatgaaga tgaagccacc a                                      21
```

```
<210> SEQ ID NO 307
<211> LENGTH: 21
<212> TYPE: DNA
<213> ORGANISM: Homo sapiens

<400> SEQUENCE: 307
aatgaagatg aagccaccag t                                            21

<210> SEQ ID NO 308
<211> LENGTH: 21
<212> TYPE: DNA
<213> ORGANISM: Homo sapiens

<400> SEQUENCE: 308
aagatgaagc caccagtatg g                                            21

<210> SEQ ID NO 309
<211> LENGTH: 21
<212> TYPE: DNA
<213> ORGANISM: Homo sapiens

<400> SEQUENCE: 309
aagccaccag tatggagctg a                                            21

<210> SEQ ID NO 310
<211> LENGTH: 21
<212> TYPE: DNA
<213> ORGANISM: Rattus norvegicus

<400> SEQUENCE: 310
aactaccaat ttcagacggt t                                            21

<210> SEQ ID NO 311
<211> LENGTH: 21
<212> TYPE: DNA
<213> ORGANISM: Rattus norvegicus

<400> SEQUENCE: 311
aatttcagac ggttcactcc a                                            21

<210> SEQ ID NO 312
<211> LENGTH: 21
<212> TYPE: DNA
<213> ORGANISM: Rattus norvegicus

<400> SEQUENCE: 312
aagcagattg ctgctcaccg c                                            21

<210> SEQ ID NO 313
<211> LENGTH: 21
<212> TYPE: DNA
<213> ORGANISM: Rattus norvegicus

<400> SEQUENCE: 313
aagaaggcca gaaccaagca c                                            21

<210> SEQ ID NO 314
<211> LENGTH: 21
<212> TYPE: DNA
<213> ORGANISM: Rattus norvegicus

<400> SEQUENCE: 314
aaggccagaa ccaagcacag a                                            21
```

```
<210> SEQ ID NO 315
<211> LENGTH: 21
<212> TYPE: DNA
<213> ORGANISM: Rattus norvegicus

<400> SEQUENCE: 315
aaccaagcac agaggacagg a                                             21

<210> SEQ ID NO 316
<211> LENGTH: 21
<212> TYPE: DNA
<213> ORGANISM: Rattus norvegicus

<400> SEQUENCE: 316
aagcacagag gacaggagga c                                             21

<210> SEQ ID NO 317
<211> LENGTH: 21
<212> TYPE: DNA
<213> ORGANISM: Rattus norvegicus

<400> SEQUENCE: 317
aagggcgaga agcccaggcc t                                             21

<210> SEQ ID NO 318
<211> LENGTH: 21
<212> TYPE: DNA
<213> ORGANISM: Rattus norvegicus

<400> SEQUENCE: 318
aagcccaggc ctcagctgga c                                             21

<210> SEQ ID NO 319
<211> LENGTH: 21
<212> TYPE: DNA
<213> ORGANISM: Rattus norvegicus

<400> SEQUENCE: 319
aaagcctgta accagctgcc c                                             21

<210> SEQ ID NO 320
<211> LENGTH: 21
<212> TYPE: DNA
<213> ORGANISM: Rattus norvegicus

<400> SEQUENCE: 320
aaccagctgc ccaagttcta t                                             21

<210> SEQ ID NO 321
<211> LENGTH: 21
<212> TYPE: DNA
<213> ORGANISM: Rattus norvegicus

<400> SEQUENCE: 321
aagttctatg gtgagctccc a                                             21

<210> SEQ ID NO 322
<211> LENGTH: 21
<212> TYPE: DNA
<213> ORGANISM: Rattus norvegicus

<400> SEQUENCE: 322
aactggtcgg ggagcccctg g                                             21
```

```
<210> SEQ ID NO 323
<211> LENGTH: 21
<212> TYPE: DNA
<213> ORGANISM: Rattus norvegicus

<400> SEQUENCE: 323
aataaaagca ggaccatttc c                                              21

<210> SEQ ID NO 324
<211> LENGTH: 21
<212> TYPE: DNA
<213> ORGANISM: Rattus norvegicus

<400> SEQUENCE: 324
aaaagcagga ccatttccag a                                              21

<210> SEQ ID NO 325
<211> LENGTH: 21
<212> TYPE: DNA
<213> ORGANISM: Rattus norvegicus

<400> SEQUENCE: 325
aagcaggacc atttccagat t                                              21

<210> SEQ ID NO 326
<211> LENGTH: 21
<212> TYPE: DNA
<213> ORGANISM: Rattus norvegicus

<400> SEQUENCE: 326
aacctgatca gaagaacagc c                                              21

<210> SEQ ID NO 327
<211> LENGTH: 21
<212> TYPE: DNA
<213> ORGANISM: Rattus norvegicus

<400> SEQUENCE: 327
aagaacagcc atcaaagtgt c                                              21

<210> SEQ ID NO 328
<211> LENGTH: 21
<212> TYPE: DNA
<213> ORGANISM: Rattus norvegicus

<400> SEQUENCE: 328
aacagccatc aaagtgtctg t                                              21

<210> SEQ ID NO 329
<211> LENGTH: 21
<212> TYPE: DNA
<213> ORGANISM: Rattus norvegicus

<400> SEQUENCE: 329
aaagtgtctg tccattcctg g                                              21

<210> SEQ ID NO 330
<211> LENGTH: 21
<212> TYPE: DNA
<213> ORGANISM: Rattus norvegicus

<400> SEQUENCE: 330
aactgcgtgt gcatgacccg a                                              21
```

```
<210> SEQ ID NO 331
<211> LENGTH: 21
<212> TYPE: DNA
<213> ORGANISM: Rattus norvegicus

<400> SEQUENCE: 331
aactgatctt ccagagaaag t                                             21

<210> SEQ ID NO 332
<211> LENGTH: 21
<212> TYPE: DNA
<213> ORGANISM: Rattus norvegicus

<400> SEQUENCE: 332
aaagtcgagt acgtcttcac t                                             21

<210> SEQ ID NO 333
<211> LENGTH: 21
<212> TYPE: DNA
<213> ORGANISM: Rattus norvegicus

<400> SEQUENCE: 333
aagatactgg caagagggtt t                                             21

<210> SEQ ID NO 334
<211> LENGTH: 21
<212> TYPE: DNA
<213> ORGANISM: Rattus norvegicus

<400> SEQUENCE: 334
aagagggttt tgtctaaatg a                                             21

<210> SEQ ID NO 335
<211> LENGTH: 21
<212> TYPE: DNA
<213> ORGANISM: Rattus norvegicus

<400> SEQUENCE: 335
aaatgagttc acttatcttc g                                             21

<210> SEQ ID NO 336
<211> LENGTH: 21
<212> TYPE: DNA
<213> ORGANISM: Rattus norvegicus

<400> SEQUENCE: 336
aactggctgg acttcagtgt c                                             21

<210> SEQ ID NO 337
<211> LENGTH: 21
<212> TYPE: DNA
<213> ORGANISM: Rattus norvegicus

<400> SEQUENCE: 337
aatctcaggc ctgcggacat t                                             21

<210> SEQ ID NO 338
<211> LENGTH: 21
<212> TYPE: DNA
<213> ORGANISM: Rattus norvegicus

<400> SEQUENCE: 338
aaaactgttt ctgtgatccc a                                             21
```

```
<210> SEQ ID NO 339
<211> LENGTH: 21
<212> TYPE: DNA
<213> ORGANISM: Rattus norvegicus

<400> SEQUENCE: 339
aactgtttct gtgatcccag g                                          21

<210> SEQ ID NO 340
<211> LENGTH: 21
<212> TYPE: DNA
<213> ORGANISM: Rattus norvegicus

<400> SEQUENCE: 340
aaggtcatcg tgggagccct g                                          21

<210> SEQ ID NO 341
<211> LENGTH: 21
<212> TYPE: DNA
<213> ORGANISM: Rattus norvegicus

<400> SEQUENCE: 341
aagctggccg acgtgactat c                                          21

<210> SEQ ID NO 342
<211> LENGTH: 21
<212> TYPE: DNA
<213> ORGANISM: Rattus norvegicus

<400> SEQUENCE: 342
aaggggaacc ttaagaacaa a                                          21

<210> SEQ ID NO 343
<211> LENGTH: 21
<212> TYPE: DNA
<213> ORGANISM: Rattus norvegicus

<400> SEQUENCE: 343
aaccttaaga acaaatgcat c                                          21

<210> SEQ ID NO 344
<211> LENGTH: 21
<212> TYPE: DNA
<213> ORGANISM: Rattus norvegicus

<400> SEQUENCE: 344
aagaacaaat gcatcaggaa c                                          21

<210> SEQ ID NO 345
<211> LENGTH: 21
<212> TYPE: DNA
<213> ORGANISM: Rattus norvegicus

<400> SEQUENCE: 345
aacaaatgca tcaggaacgg a                                          21

<210> SEQ ID NO 346
<211> LENGTH: 21
<212> TYPE: DNA
<213> ORGANISM: Rattus norvegicus

<400> SEQUENCE: 346
aaatgcatca ggaacggaac a                                          21
```

```
<210> SEQ ID NO 347
<211> LENGTH: 21
<212> TYPE: DNA
<213> ORGANISM: Rattus norvegicus

<400> SEQUENCE: 347
aacggaacag atccccacaa g                                          21

<210> SEQ ID NO 348
<211> LENGTH: 21
<212> TYPE: DNA
<213> ORGANISM: Rattus norvegicus

<400> SEQUENCE: 348
aacagatccc cacaaggctg a                                          21

<210> SEQ ID NO 349
<211> LENGTH: 21
<212> TYPE: DNA
<213> ORGANISM: Rattus norvegicus

<400> SEQUENCE: 349
aaggctgaca acctctcatc t                                          21

<210> SEQ ID NO 350
<211> LENGTH: 21
<212> TYPE: DNA
<213> ORGANISM: Rattus norvegicus

<400> SEQUENCE: 350
aacctctcat ctgaaatggc a                                          21

<210> SEQ ID NO 351
<211> LENGTH: 21
<212> TYPE: DNA
<213> ORGANISM: Rattus norvegicus

<400> SEQUENCE: 351
aaatggcaga atacatcttc a                                          21

<210> SEQ ID NO 352
<211> LENGTH: 21
<212> TYPE: DNA
<213> ORGANISM: Rattus norvegicus

<400> SEQUENCE: 352
aatacatctt catcaagcct g                                          21

<210> SEQ ID NO 353
<211> LENGTH: 21
<212> TYPE: DNA
<213> ORGANISM: Rattus norvegicus

<400> SEQUENCE: 353
aagcctggta ctacggatcc c                                          21

<210> SEQ ID NO 354
<211> LENGTH: 21
<212> TYPE: DNA
<213> ORGANISM: Rattus norvegicus

<400> SEQUENCE: 354
aatgggtctg atgctggtca c                                          21
```

```
<210> SEQ ID NO 355
<211> LENGTH: 21
<212> TYPE: DNA
<213> ORGANISM: Rattus norvegicus

<400> SEQUENCE: 355
aaaactcctg acaacccgga t                                              21

<210> SEQ ID NO 356
<211> LENGTH: 21
<212> TYPE: DNA
<213> ORGANISM: Rattus norvegicus

<400> SEQUENCE: 356
aactcctgac aacccggatt t                                              21

<210> SEQ ID NO 357
<211> LENGTH: 21
<212> TYPE: DNA
<213> ORGANISM: Rattus norvegicus

<400> SEQUENCE: 357
aacccggatt ttaactacac c                                              21

<210> SEQ ID NO 358
<211> LENGTH: 21
<212> TYPE: DNA
<213> ORGANISM: Rattus norvegicus

<400> SEQUENCE: 358
aactacacca gctttgattc c                                              21

<210> SEQ ID NO 359
<211> LENGTH: 21
<212> TYPE: DNA
<213> ORGANISM: Rattus norvegicus

<400> SEQUENCE: 359
aaaatgtaca tggtcttttt c                                              21

<210> SEQ ID NO 360
<211> LENGTH: 21
<212> TYPE: DNA
<213> ORGANISM: Rattus norvegicus

<400> SEQUENCE: 360
aatgtacatg gtctttttcg t                                              21

<210> SEQ ID NO 361
<211> LENGTH: 21
<212> TYPE: DNA
<213> ORGANISM: Rattus norvegicus

<400> SEQUENCE: 361
aatttgatct tggccgtggt c                                              21

<210> SEQ ID NO 362
<211> LENGTH: 21
<212> TYPE: DNA
<213> ORGANISM: Rattus norvegicus

<400> SEQUENCE: 362
aagagcagag ccaggcaaca a                                              21
```

<210> SEQ ID NO 363
<211> LENGTH: 21
<212> TYPE: DNA
<213> ORGANISM: Rattus norvegicus

<400> SEQUENCE: 363
aacaattgca gaaatcgaag c                                              21

<210> SEQ ID NO 364
<211> LENGTH: 21
<212> TYPE: DNA
<213> ORGANISM: Rattus norvegicus

<400> SEQUENCE: 364
aattgcagaa atcgaagcca a                                              21

<210> SEQ ID NO 365
<211> LENGTH: 21
<212> TYPE: DNA
<213> ORGANISM: Rattus norvegicus

<400> SEQUENCE: 365
aaatcgaagc caaggaaaaa a                                              21

<210> SEQ ID NO 366
<211> LENGTH: 21
<212> TYPE: DNA
<213> ORGANISM: Rattus norvegicus

<400> SEQUENCE: 366
aagccaagga aaaaaagttc c                                              21

<210> SEQ ID NO 367
<211> LENGTH: 21
<212> TYPE: DNA
<213> ORGANISM: Rattus norvegicus

<400> SEQUENCE: 367
aaggaaaaaa agttccagga a                                              21

<210> SEQ ID NO 368
<211> LENGTH: 21
<212> TYPE: DNA
<213> ORGANISM: Rattus norvegicus

<400> SEQUENCE: 368 aaaaaagtt ccaggaagcc c                                               21

<210> SEQ ID NO 369
<211> LENGTH: 21
<212> TYPE: DNA
<213> ORGANISM: Rattus norvegicus

<400> SEQUENCE: 369
aaaaagttcc aggaagccct t                                              21

<210> SEQ ID NO 370
<211> LENGTH: 21
<212> TYPE: DNA
<213> ORGANISM: Rattus norvegicus

<400> SEQUENCE: 370
aaagttccag gaagcccttg a                                              21

```
<210> SEQ ID NO 371
<211> LENGTH: 21
<212> TYPE: DNA
<213> ORGANISM: Rattus norvegicus

<400> SEQUENCE: 371
aagcccttga ggtgctgcag a                                              21

<210> SEQ ID NO 372
<211> LENGTH: 21
<212> TYPE: DNA
<213> ORGANISM: Rattus norvegicus

<400> SEQUENCE: 372
aaggaacagg aggtgctggc a                                              21

<210> SEQ ID NO 373
<211> LENGTH: 21
<212> TYPE: DNA
<213> ORGANISM: Rattus norvegicus

<400> SEQUENCE: 373
aacaggaggt gctggcagcc c                                              21

<210> SEQ ID NO 374
<211> LENGTH: 21
<212> TYPE: DNA
<213> ORGANISM: Rattus norvegicus

<400> SEQUENCE: 374
aaaaacgcca atgagagaag a                                              21

<210> SEQ ID NO 375
<211> LENGTH: 21
<212> TYPE: DNA
<213> ORGANISM: Rattus norvegicus

<400> SEQUENCE: 375
aaacgccaat gagagaagac c                                              21

<210> SEQ ID NO 376
<211> LENGTH: 21
<212> TYPE: DNA
<213> ORGANISM: Rattus norvegicus

<400> SEQUENCE: 376
aatgagagaa gacccagggt g                                              21

<210> SEQ ID NO 377
<211> LENGTH: 21
<212> TYPE: DNA
<213> ORGANISM: Rattus norvegicus

<400> SEQUENCE: 377
aagacccagg gtgaaatcaa g                                              21

<210> SEQ ID NO 378
<211> LENGTH: 21
<212> TYPE: DNA
<213> ORGANISM: Rattus norvegicus

<400> SEQUENCE: 378
aaatcaaggg tgtcagaggg c                                              21
```

```
<210> SEQ ID NO 379
<211> LENGTH: 21
<212> TYPE: DNA
<213> ORGANISM: Rattus norvegicus

<400> SEQUENCE: 379
aagggtgtca gagggctcca c                                    21

<210> SEQ ID NO 380
<211> LENGTH: 21
<212> TYPE: DNA
<213> ORGANISM: Rattus norvegicus

<400> SEQUENCE: 380
aacaggtcac cccaatctga c                                    21

<210> SEQ ID NO 381
<211> LENGTH: 21
<212> TYPE: DNA
<213> ORGANISM: Rattus norvegicus

<400> SEQUENCE: 381
aatctgaccc ttacaaccag c                                    21

<210> SEQ ID NO 382
<211> LENGTH: 21
<212> TYPE: DNA
<213> ORGANISM: Rattus norvegicus

<400> SEQUENCE: 382
aaccagcgca ggatgtcttt c                                    21

<210> SEQ ID NO 383
<211> LENGTH: 21
<212> TYPE: DNA
<213> ORGANISM: Rattus norvegicus

<400> SEQUENCE: 383
aagacgcagg gctagccacg g                                    21

<210> SEQ ID NO 384
<211> LENGTH: 21
<212> TYPE: DNA
<213> ORGANISM: Rattus norvegicus

<400> SEQUENCE: 384
aagacatctc atttcctgac g                                    21

<210> SEQ ID NO 385
<211> LENGTH: 21
<212> TYPE: DNA
<213> ORGANISM: Rattus norvegicus

<400> SEQUENCE: 385
aaagccgtcg aggttccata t                                    21

<210> SEQ ID NO 386
<211> LENGTH: 21
<212> TYPE: DNA
<213> ORGANISM: Rattus norvegicus

<400> SEQUENCE: 386
aaccctggcc gtagacatgg a                                    21
```

```
<210> SEQ ID NO 387
<211> LENGTH: 21
<212> TYPE: DNA
<213> ORGANISM: Rattus norvegicus

<400> SEQUENCE: 387
aagagggaca gctcggagtg c                                            21

<210> SEQ ID NO 388
<211> LENGTH: 21
<212> TYPE: DNA
<213> ORGANISM: Rattus norvegicus

<400> SEQUENCE: 388
aaggcccggc actcgacact a                                            21

<210> SEQ ID NO 389
<211> LENGTH: 21
<212> TYPE: DNA
<213> ORGANISM: Rattus norvegicus

<400> SEQUENCE: 389
aagagcttcc tgtctgcggg c                                            21

<210> SEQ ID NO 390
<211> LENGTH: 21
<212> TYPE: DNA
<213> ORGANISM: Rattus norvegicus

<400> SEQUENCE: 390
aacgaacctt tccgagcaca g                                            21

<210> SEQ ID NO 391
<211> LENGTH: 21
<212> TYPE: DNA
<213> ORGANISM: Rattus norvegicus

<400> SEQUENCE: 391
aacctttccg agcacagagg g                                            21

<210> SEQ ID NO 392
<211> LENGTH: 21
<212> TYPE: DNA
<213> ORGANISM: Rattus norvegicus

<400> SEQUENCE: 392
aagagtctaa gctgaagtgc c                                            21

<210> SEQ ID NO 393
<211> LENGTH: 21
<212> TYPE: DNA
<213> ORGANISM: Rattus norvegicus

<400> SEQUENCE: 393
aagctgaagt gcccaccctg c                                            21

<210> SEQ ID NO 394
<211> LENGTH: 21
<212> TYPE: DNA
<213> ORGANISM: Rattus norvegicus

<400> SEQUENCE: 394
aagtgcccac cctgcttgat c                                            21
```

```
<210> SEQ ID NO 395
<211> LENGTH: 21
<212> TYPE: DNA
<213> ORGANISM: Rattus norvegicus

<400> SEQUENCE: 395
aagtatctga tctgggagtg c                                              21

<210> SEQ ID NO 396
<211> LENGTH: 21
<212> TYPE: DNA
<213> ORGANISM: Rattus norvegicus

<400> SEQUENCE: 396
aagtggagga agttcaagat g                                              21

<210> SEQ ID NO 397
<211> LENGTH: 21
<212> TYPE: DNA
<213> ORGANISM: Rattus norvegicus

<400> SEQUENCE: 397
aagttcaaga tggcgctgtt c                                              21

<210> SEQ ID NO 398
<211> LENGTH: 21
<212> TYPE: DNA
<213> ORGANISM: Rattus norvegicus

<400> SEQUENCE: 398
aagatggcgc tgttcgagct g                                              21

<210> SEQ ID NO 399
<211> LENGTH: 21
<212> TYPE: DNA
<213> ORGANISM: Rattus norvegicus

<400> SEQUENCE: 399
aacaccgtct tcatggccat g                                              21

<210> SEQ ID NO 400
<211> LENGTH: 21
<212> TYPE: DNA
<213> ORGANISM: Rattus norvegicus

<400> SEQUENCE: 400
aagccggcaa cattgtcttc a                                              21

<210> SEQ ID NO 401
<211> LENGTH: 21
<212> TYPE: DNA
<213> ORGANISM: Rattus norvegicus

<400> SEQUENCE: 401
aacattgtct tcaccgtgtt t                                              21

<210> SEQ ID NO 402
<211> LENGTH: 21
<212> TYPE: DNA
<213> ORGANISM: Rattus norvegicus

<400> SEQUENCE: 402
aatggagatg gccttcaaga t                                              21
```

```
<210> SEQ ID NO 403
<211> LENGTH: 21
<212> TYPE: DNA
<213> ORGANISM: Rattus norvegicus

<400> SEQUENCE: 403
aagatcattg ccttcgaccc c                                    21

<210> SEQ ID NO 404
<211> LENGTH: 21
<212> TYPE: DNA
<213> ORGANISM: Rattus norvegicus

<400> SEQUENCE: 404
aagaagtgga atatcttcga c                                    21

<210> SEQ ID NO 405
<211> LENGTH: 21
<212> TYPE: DNA
<213> ORGANISM: Rattus norvegicus

<400> SEQUENCE: 405
aagtggaata tcttcgactg t                                    21

<210> SEQ ID NO 406
<211> LENGTH: 21
<212> TYPE: DNA
<213> ORGANISM: Rattus norvegicus

<400> SEQUENCE: 406
aatatcttcg actgtgtcat c                                    21

<210> SEQ ID NO 407
<211> LENGTH: 21
<212> TYPE: DNA
<213> ORGANISM: Rattus norvegicus

<400> SEQUENCE: 407
aagaagggca gcctgtctgt g                                    21

<210> SEQ ID NO 408
<211> LENGTH: 21
<212> TYPE: DNA
<213> ORGANISM: Rattus norvegicus

<400> SEQUENCE: 408
aagggcagcc tgtctgtgct c                                    21

<210> SEQ ID NO 409
<211> LENGTH: 21
<212> TYPE: DNA
<213> ORGANISM: Rattus norvegicus

<400> SEQUENCE: 409
aagctggcca agtcctggcc c                                    21

<210> SEQ ID NO 410
<211> LENGTH: 21
<212> TYPE: DNA
<213> ORGANISM: Rattus norvegicus

<400> SEQUENCE: 410
aagtcctggc ccaccctgaa c                                    21
```

```
<210> SEQ ID NO 411
<211> LENGTH: 21
<212> TYPE: DNA
<213> ORGANISM: Rattus norvegicus

<400> SEQUENCE: 411
aacaccctca tcaagatcat c                                              21

<210> SEQ ID NO 412
<211> LENGTH: 21
<212> TYPE: DNA
<213> ORGANISM: Rattus norvegicus

<400> SEQUENCE: 412
aagatcatcg ggaactccgt g                                              21

<210> SEQ ID NO 413
<211> LENGTH: 21
<212> TYPE: DNA
<213> ORGANISM: Rattus norvegicus

<400> SEQUENCE: 413
aactccgtgg gggccctggg c                                              21

<210> SEQ ID NO 414
<211> LENGTH: 21
<212> TYPE: DNA
<213> ORGANISM: Rattus norvegicus

<400> SEQUENCE: 414
aacctgacct ttatcctggc c                                              21

<210> SEQ ID NO 415
<211> LENGTH: 21
<212> TYPE: DNA
<213> ORGANISM: Rattus norvegicus

<400> SEQUENCE: 415
aaagcagctt ctctcagagg a                                              21

<210> SEQ ID NO 416
<211> LENGTH: 21
<212> TYPE: DNA
<213> ORGANISM: Rattus norvegicus

<400> SEQUENCE: 416
aaggacggcg tctccgtgtg g                                              21

<210> SEQ ID NO 417
<211> LENGTH: 21
<212> TYPE: DNA
<213> ORGANISM: Rattus norvegicus

<400> SEQUENCE: 417
aacggcgaga agctccgctg g                                              21

<210> SEQ ID NO 418
<211> LENGTH: 21
<212> TYPE: DNA
<213> ORGANISM: Rattus norvegicus

<400> SEQUENCE: 418
aagctccgct ggcacatgtg t                                              21
```

```
<210> SEQ ID NO 419
<211> LENGTH: 21
<212> TYPE: DNA
<213> ORGANISM: Rattus norvegicus

<400> SEQUENCE: 419
aatcctctgc ggggagtgga t                                              21

<210> SEQ ID NO 420
<211> LENGTH: 21
<212> TYPE: DNA
<213> ORGANISM: Rattus norvegicus

<400> SEQUENCE: 420
aacatgtggg tctgcatgga g                                              21

<210> SEQ ID NO 421
<211> LENGTH: 21
<212> TYPE: DNA
<213> ORGANISM: Rattus norvegicus

<400> SEQUENCE: 421
aaatccatct gcctcatcct c                                              21

<210> SEQ ID NO 422
<211> LENGTH: 21
<212> TYPE: DNA
<213> ORGANISM: Rattus norvegicus

<400> SEQUENCE: 422
aacctagtgg tgctcaacct t                                              21

<210> SEQ ID NO 423
<211> LENGTH: 21
<212> TYPE: DNA
<213> ORGANISM: Rattus norvegicus

<400> SEQUENCE: 423
aaccttttca tcgctttact g                                              21

<210> SEQ ID NO 424
<211> LENGTH: 21
<212> TYPE: DNA
<213> ORGANISM: Rattus norvegicus

<400> SEQUENCE: 424
aactccttca gcgcggacaa c                                              21

<210> SEQ ID NO 425
<211> LENGTH: 21
<212> TYPE: DNA
<213> ORGANISM: Rattus norvegicus

<400> SEQUENCE: 425
aacctcacgg ctccagagga t                                              21

<210> SEQ ID NO 426
<211> LENGTH: 21
<212> TYPE: DNA
<213> ORGANISM: Rattus norvegicus

<400> SEQUENCE: 426
aacaacttgc agttagcact g                                              21
```

-continued

<210> SEQ ID NO 427
<211> LENGTH: 21
<212> TYPE: DNA
<213> ORGANISM: Rattus norvegicus

<400> SEQUENCE: 427
aacttgcagt tagcactggc c                                          21

<210> SEQ ID NO 428
<211> LENGTH: 21
<212> TYPE: DNA
<213> ORGANISM: Rattus norvegicus

<400> SEQUENCE: 428
aaggtggaga cccagctggg c                                          21

<210> SEQ ID NO 429
<211> LENGTH: 21
<212> TYPE: DNA
<213> ORGANISM: Rattus norvegicus

<400> SEQUENCE: 429
aagcccccac tcaccagctc a                                          21

<210> SEQ ID NO 430
<211> LENGTH: 21
<212> TYPE: DNA
<213> ORGANISM: Rattus norvegicus

<400> SEQUENCE: 430
aagaaccaca ttgccactga t                                          21

<210> SEQ ID NO 431
<211> LENGTH: 21
<212> TYPE: DNA
<213> ORGANISM: Rattus norvegicus

<400> SEQUENCE: 431
aaccacattg ccactgatgc t                                          21

<210> SEQ ID NO 432
<211> LENGTH: 21
<212> TYPE: DNA
<213> ORGANISM: Rattus norvegicus

<400> SEQUENCE: 432
aacctgacaa agccagctct c                                          21

<210> SEQ ID NO 433
<211> LENGTH: 21
<212> TYPE: DNA
<213> ORGANISM: Rattus norvegicus

<400> SEQUENCE: 433
aaagccagct ctcagtagcc c                                          21

<210> SEQ ID NO 434
<211> LENGTH: 21
<212> TYPE: DNA
<213> ORGANISM: Rattus norvegicus

<400> SEQUENCE: 434
aaggagaacc acggggactt c                                          21

```
<210> SEQ ID NO 435
<211> LENGTH: 21
<212> TYPE: DNA
<213> ORGANISM: Rattus norvegicus

<400> SEQUENCE: 435
aaccacgggg acttcatcac t                                          21

<210> SEQ ID NO 436
<211> LENGTH: 21
<212> TYPE: DNA
<213> ORGANISM: Rattus norvegicus

<400> SEQUENCE: 436
aacgtgtggg tctctgtgcc c                                          21

<210> SEQ ID NO 437
<211> LENGTH: 21
<212> TYPE: DNA
<213> ORGANISM: Rattus norvegicus

<400> SEQUENCE: 437
aatctgacct cgacgagctc g                                          21

<210> SEQ ID NO 438
<211> LENGTH: 21
<212> TYPE: DNA
<213> ORGANISM: Rattus norvegicus

<400> SEQUENCE: 438
aagatatgga gcaggcttcg c                                          21

<210> SEQ ID NO 439
<211> LENGTH: 21
<212> TYPE: DNA
<213> ORGANISM: Rattus norvegicus

<400> SEQUENCE: 439
aagaggaccc caagggacag c                                          21

<210> SEQ ID NO 440
<211> LENGTH: 21
<212> TYPE: DNA
<213> ORGANISM: Rattus norvegicus

<400> SEQUENCE: 440
aagggacagc aggagcagtt g                                          21

<210> SEQ ID NO 441
<211> LENGTH: 21
<212> TYPE: DNA
<213> ORGANISM: Rattus norvegicus

<400> SEQUENCE: 441
aagtccaaaa gtgtgaaaac c                                          21

<210> SEQ ID NO 442
<211> LENGTH: 21
<212> TYPE: DNA
<213> ORGANISM: Rattus norvegicus

<400> SEQUENCE: 442
aaaagtgtga aaaccaccag g                                          21
```

```
<210> SEQ ID NO 443
<211> LENGTH: 21
<212> TYPE: DNA
<213> ORGANISM: Rattus norvegicus

<400> SEQUENCE: 443
aagtgtgaaa accaccaggc a                                             21

<210> SEQ ID NO 444
<211> LENGTH: 21
<212> TYPE: DNA
<213> ORGANISM: Rattus norvegicus

<400> SEQUENCE: 444
aaaaccacca ggcagccaga a                                             21

<210> SEQ ID NO 445
<211> LENGTH: 21
<212> TYPE: DNA
<213> ORGANISM: Rattus norvegicus

<400> SEQUENCE: 445
aaccaccagg cagccagaag c                                             21

<210> SEQ ID NO 446
<211> LENGTH: 21
<212> TYPE: DNA
<213> ORGANISM: Rattus norvegicus

<400> SEQUENCE: 446
aagcccagcc tccatgatgt c                                             21

<210> SEQ ID NO 447
<211> LENGTH: 21
<212> TYPE: DNA
<213> ORGANISM: Rattus norvegicus

<400> SEQUENCE: 447
aagaggaagg atagccctca g                                             21

<210> SEQ ID NO 448
<211> LENGTH: 21
<212> TYPE: DNA
<213> ORGANISM: Rattus norvegicus

<400> SEQUENCE: 448
aaggatagcc ctcaggtccc t                                             21

<210> SEQ ID NO 449
<211> LENGTH: 21
<212> TYPE: DNA
<213> ORGANISM: Rattus norvegicus

<400> SEQUENCE: 449
aaatcctgag gaagatcccc g                                             21

<210> SEQ ID NO 450
<211> LENGTH: 21
<212> TYPE: DNA
<213> ORGANISM: Rattus norvegicus

<400> SEQUENCE: 450
aagatccccg agctggcaga t                                             21
```

```
<210> SEQ ID NO 451
<211> LENGTH: 21
<212> TYPE: DNA
<213> ORGANISM: Rattus norvegicus

<400> SEQUENCE: 451
aaggctgcac tcgccgctgt c                                              21

<210> SEQ ID NO 452
<211> LENGTH: 21
<212> TYPE: DNA
<213> ORGANISM: Rattus norvegicus

<400> SEQUENCE: 452
aacgtgaata ctagcaagtc t                                              21

<210> SEQ ID NO 453
<211> LENGTH: 21
<212> TYPE: DNA
<213> ORGANISM: Rattus norvegicus

<400> SEQUENCE: 453
aatactagca agtctccttg g                                              21

<210> SEQ ID NO 454
<211> LENGTH: 21
<212> TYPE: DNA
<213> ORGANISM: Rattus norvegicus

<400> SEQUENCE: 454
aagtctcctt gggccacagg c                                              21

<210> SEQ ID NO 455
<211> LENGTH: 21
<212> TYPE: DNA
<213> ORGANISM: Rattus norvegicus

<400> SEQUENCE: 455
aagacctgct accgcatcgt g                                              21

<210> SEQ ID NO 456
<211> LENGTH: 21
<212> TYPE: DNA
<213> ORGANISM: Rattus norvegicus

<400> SEQUENCE: 456
aactacctgg aagagaaacc c                                              21

<210> SEQ ID NO 457
<211> LENGTH: 21
<212> TYPE: DNA
<213> ORGANISM: Rattus norvegicus

<400> SEQUENCE: 457
aagagaaacc ccgagtgaag t                                              21

<210> SEQ ID NO 458
<211> LENGTH: 21
<212> TYPE: DNA
<213> ORGANISM: Rattus norvegicus

<400> SEQUENCE: 458
aaaccccgag tgaagtccgt g                                              21
```

```
<210> SEQ ID NO 459
<211> LENGTH: 21
<212> TYPE: DNA
<213> ORGANISM: Rattus norvegicus

<400> SEQUENCE: 459
aagtccgtgc tggagtacac t                                           21

<210> SEQ ID NO 460
<211> LENGTH: 21
<212> TYPE: DNA
<213> ORGANISM: Rattus norvegicus

<400> SEQUENCE: 460
aagtgggtag cctatggctt c                                           21

<210> SEQ ID NO 461
<211> LENGTH: 21
<212> TYPE: DNA
<213> ORGANISM: Rattus norvegicus

<400> SEQUENCE: 461
aaaaagtatt tcaccaatgc c                                           21

<210> SEQ ID NO 462
<211> LENGTH: 21
<212> TYPE: DNA
<213> ORGANISM: Rattus norvegicus

<400> SEQUENCE: 462
aaagtatttc accaatgcct g                                           21

<210> SEQ ID NO 463
<211> LENGTH: 21
<212> TYPE: DNA
<213> ORGANISM: Rattus norvegicus

<400> SEQUENCE: 463
aatgcctggt gctggctgga c                                           21

<210> SEQ ID NO 464
<211> LENGTH: 21
<212> TYPE: DNA
<213> ORGANISM: Rattus norvegicus

<400> SEQUENCE: 464
aacatctccc tgacaagcct c                                           21

<210> SEQ ID NO 465
<211> LENGTH: 21
<212> TYPE: DNA
<213> ORGANISM: Rattus norvegicus

<400> SEQUENCE: 465
aagcctcata gcgaagatcc t                                           21

<210> SEQ ID NO 466
<211> LENGTH: 21
<212> TYPE: DNA
<213> ORGANISM: Rattus norvegicus

<400> SEQUENCE: 466
aagatccttg agtattccga c                                           21
```

-continued

<210> SEQ ID NO 467
<211> LENGTH: 21
<212> TYPE: DNA
<213> ORGANISM: Rattus norvegicus

<400> SEQUENCE: 467
aaagcccttc ggactctccg t                                              21

<210> SEQ ID NO 468
<211> LENGTH: 21
<212> TYPE: DNA
<213> ORGANISM: Rattus norvegicus

<400> SEQUENCE: 468
aaggcatgag ggtagtggtg g                                              21

<210> SEQ ID NO 469
<211> LENGTH: 21
<212> TYPE: DNA
<213> ORGANISM: Rattus norvegicus

<400> SEQUENCE: 469
aacgtcctcc tcgtctgcct c                                              21

<210> SEQ ID NO 470
<211> LENGTH: 21
<212> TYPE: DNA
<213> ORGANISM: Rattus norvegicus

<400> SEQUENCE: 470
aacctcttcg ccgggaaatt t                                              21

<210> SEQ ID NO 471
<211> LENGTH: 21
<212> TYPE: DNA
<213> ORGANISM: Rattus norvegicus

<400> SEQUENCE: 471
aaattttcga agtgcgtcga c                                              21

<210> SEQ ID NO 472
<211> LENGTH: 21
<212> TYPE: DNA
<213> ORGANISM: Rattus norvegicus

<400> SEQUENCE: 472
aagtgcgtcg acaccagaaa t                                              21

<210> SEQ ID NO 473
<211> LENGTH: 21
<212> TYPE: DNA
<213> ORGANISM: Rattus norvegicus

<400> SEQUENCE: 473
aaataaccca ttttccaacg t                                              21

<210> SEQ ID NO 474
<211> LENGTH: 21
<212> TYPE: DNA
<213> ORGANISM: Rattus norvegicus

<400> SEQUENCE: 474
aacccatttt ccaacgtgaa t                                              21

```
<210> SEQ ID NO 475
<211> LENGTH: 21
<212> TYPE: DNA
<213> ORGANISM: Rattus norvegicus

<400> SEQUENCE: 475
aacgtgaatt cgacgatggt g                                        21

<210> SEQ ID NO 476
<211> LENGTH: 21
<212> TYPE: DNA
<213> ORGANISM: Rattus norvegicus

<400> SEQUENCE: 476
aattcgacga tggtgaataa c                                        21

<210> SEQ ID NO 477
<211> LENGTH: 21
<212> TYPE: DNA
<213> ORGANISM: Rattus norvegicus

<400> SEQUENCE: 477
aataacaagt ccgagtgtca c                                        21

<210> SEQ ID NO 478
<211> LENGTH: 21
<212> TYPE: DNA
<213> ORGANISM: Rattus norvegicus

<400> SEQUENCE: 478
aacaagtccg agtgtcacaa t                                        21

<210> SEQ ID NO 479
<211> LENGTH: 21
<212> TYPE: DNA
<213> ORGANISM: Rattus norvegicus

<400> SEQUENCE: 479
aagtccgagt gtcacaatca a                                        21

<210> SEQ ID NO 480
<211> LENGTH: 21
<212> TYPE: DNA
<213> ORGANISM: Rattus norvegicus

<400> SEQUENCE: 480
aatcaaaaca gcaccggcca c                                        21

<210> SEQ ID NO 481
<211> LENGTH: 21
<212> TYPE: DNA
<213> ORGANISM: Rattus norvegicus

<400> SEQUENCE: 481
aaaacagcac cggccacttc t                                        21

<210> SEQ ID NO 482
<211> LENGTH: 21
<212> TYPE: DNA
<213> ORGANISM: Rattus norvegicus

<400> SEQUENCE: 482
aacagcaccg gccacttctt c                                        21
```

<210> SEQ ID NO 483
<211> LENGTH: 21
<212> TYPE: DNA
<213> ORGANISM: Rattus norvegicus

<400> SEQUENCE: 483
aacgtcaaag tcaacttcga c                                                  21

<210> SEQ ID NO 484
<211> LENGTH: 21
<212> TYPE: DNA
<213> ORGANISM: Rattus norvegicus

<400> SEQUENCE: 484
aaagtcaact tcgacaacgt c                                                  21

<210> SEQ ID NO 485
<211> LENGTH: 21
<212> TYPE: DNA
<213> ORGANISM: Rattus norvegicus

<400> SEQUENCE: 485
aacttcgaca acgtcgctat g                                                  21

<210> SEQ ID NO 486
<211> LENGTH: 21
<212> TYPE: DNA
<213> ORGANISM: Rattus norvegicus

<400> SEQUENCE: 486
aacgtcgcta tgggctacct c                                                  21

<210> SEQ ID NO 487
<211> LENGTH: 21
<212> TYPE: DNA
<213> ORGANISM: Rattus norvegicus

<400> SEQUENCE: 487
aaccttcaaa ggctggatgg a                                                  21

<210> SEQ ID NO 488
<211> LENGTH: 21
<212> TYPE: DNA
<213> ORGANISM: Rattus norvegicus

<400> SEQUENCE: 488
aaaggctgga tggacataat g                                                  21

<210> SEQ ID NO 489
<211> LENGTH: 21
<212> TYPE: DNA
<213> ORGANISM: Rattus norvegicus

<400> SEQUENCE: 489
aatgtatgca gctgttgatt c                                                  21

<210> SEQ ID NO 490
<211> LENGTH: 21
<212> TYPE: DNA
<213> ORGANISM: Rattus norvegicus

<400> SEQUENCE: 490
aacagtcagc ctaactggga g                                                  21

```
<210> SEQ ID NO 491
<211> LENGTH: 21
<212> TYPE: DNA
<213> ORGANISM: Rattus norvegicus

<400> SEQUENCE: 491
aactgggaga acaacttgta c                                              21

<210> SEQ ID NO 492
<211> LENGTH: 21
<212> TYPE: DNA
<213> ORGANISM: Rattus norvegicus

<400> SEQUENCE: 492
aacaacttgt acatgtacct g                                              21

<210> SEQ ID NO 493
<211> LENGTH: 21
<212> TYPE: DNA
<213> ORGANISM: Rattus norvegicus

<400> SEQUENCE: 493
aacttgtaca tgtacctgta c                                              21

<210> SEQ ID NO 494
<211> LENGTH: 21
<212> TYPE: DNA
<213> ORGANISM: Rattus norvegicus

<400> SEQUENCE: 494
aatctctttg ttggggtcat a                                              21

<210> SEQ ID NO 495
<211> LENGTH: 21
<212> TYPE: DNA
<213> ORGANISM: Rattus norvegicus

<400> SEQUENCE: 495
aatcgacaac ttcaaccaac a                                              21

<210> SEQ ID NO 496
<211> LENGTH: 21
<212> TYPE: DNA
<213> ORGANISM: Rattus norvegicus

<400> SEQUENCE: 496
aacttcaacc aacagaaaaa a                                              21

<210> SEQ ID NO 497
<211> LENGTH: 21
<212> TYPE: DNA
<213> ORGANISM: Rattus norvegicus

<400> SEQUENCE: 497
aaccaacaga aaaaaagct a                                               21

<210> SEQ ID NO 498
<211> LENGTH: 21
<212> TYPE: DNA
<213> ORGANISM: Rattus norvegicus

<400> SEQUENCE: 498
aacagaaaaa aaagctagga g                                              21
```

```
<210> SEQ ID NO 499
<211> LENGTH: 21
<212> TYPE: DNA
<213> ORGANISM: Rattus norvegicus

<400> SEQUENCE: 499
aaaaaaaagc taggaggcca g                                        21

<210> SEQ ID NO 500
<211> LENGTH: 21
<212> TYPE: DNA
<213> ORGANISM: Rattus norvegicus

<400> SEQUENCE: 500
aaaaaagcta ggaggccagg a                                        21

<210> SEQ ID NO 501
<211> LENGTH: 21
<212> TYPE: DNA
<213> ORGANISM: Rattus norvegicus

<400> SEQUENCE: 501
aaaagctagg aggccaggac a                                        21

<210> SEQ ID NO 502
<211> LENGTH: 21
<212> TYPE: DNA
<213> ORGANISM: Rattus norvegicus

<400> SEQUENCE: 502
aagctaggag gccaggacat c                                        21

<210> SEQ ID NO 503
<211> LENGTH: 21
<212> TYPE: DNA
<213> ORGANISM: Rattus norvegicus

<400> SEQUENCE: 503
aagagcagaa gaagtactac a                                        21

<210> SEQ ID NO 504
<211> LENGTH: 21
<212> TYPE: DNA
<213> ORGANISM: Rattus norvegicus

<400> SEQUENCE: 504
aagaagtact acaatgccat g                                        21

<210> SEQ ID NO 505
<211> LENGTH: 21
<212> TYPE: DNA
<213> ORGANISM: Rattus norvegicus

<400> SEQUENCE: 505
aagtactaca atgccatgaa g                                        21

<210> SEQ ID NO 506
<211> LENGTH: 21
<212> TYPE: DNA
<213> ORGANISM: Rattus norvegicus

<400> SEQUENCE: 506
aatgccatga agaagctggg c                                        21
```

```
<210> SEQ ID NO 507
<211> LENGTH: 21
<212> TYPE: DNA
<213> ORGANISM: Rattus norvegicus

<400> SEQUENCE: 507
aagaagctgg gctccaagaa a                                                 21

<210> SEQ ID NO 508
<211> LENGTH: 21
<212> TYPE: DNA
<213> ORGANISM: Rattus norvegicus

<400> SEQUENCE: 508
aagctgggct ccaagaaacc c                                                 21

<210> SEQ ID NO 509
<211> LENGTH: 21
<212> TYPE: DNA
<213> ORGANISM: Rattus norvegicus

<400> SEQUENCE: 509
aagaaacccc agaagcccat c                                                 21

<210> SEQ ID NO 510
<211> LENGTH: 21
<212> TYPE: DNA
<213> ORGANISM: Rattus norvegicus

<400> SEQUENCE: 510 aaacccaga agcccatccc a                                                  21

<210> SEQ ID NO 511
<211> LENGTH: 21
<212> TYPE: DNA
<213> ORGANISM: Rattus norvegicus

<400> SEQUENCE: 511
aagcccatcc cacggcccct g                                                 21

<210> SEQ ID NO 512
<211> LENGTH: 21
<212> TYPE: DNA
<213> ORGANISM: Rattus norvegicus

<400> SEQUENCE: 512
aataagtacc aaggcttcgt g                                                 21

<210> SEQ ID NO 513
<211> LENGTH: 21
<212> TYPE: DNA
<213> ORGANISM: Rattus norvegicus

<400> SEQUENCE: 513
aagtaccaag gcttcgtgtt t                                                 21

<210> SEQ ID NO 514
<211> LENGTH: 21
<212> TYPE: DNA
<213> ORGANISM: Rattus norvegicus

<400> SEQUENCE: 514
aaggcttcgt gtttgacatc g                                                 21
```

```
<210> SEQ ID NO 515
<211> LENGTH: 21
<212> TYPE: DNA
<213> ORGANISM: Rattus norvegicus

<400> SEQUENCE: 515
aagcctttga catcatcatc a                                              21

<210> SEQ ID NO 516
<211> LENGTH: 21
<212> TYPE: DNA
<213> ORGANISM: Rattus norvegicus

<400> SEQUENCE: 516
aacatgatca ccatgatggt g                                              21

<210> SEQ ID NO 517
<211> LENGTH: 21
<212> TYPE: DNA
<213> ORGANISM: Rattus norvegicus

<400> SEQUENCE: 517
aagacgaagg ttctgggcag a                                              21

<210> SEQ ID NO 518
<211> LENGTH: 21
<212> TYPE: DNA
<213> ORGANISM: Rattus norvegicus

<400> SEQUENCE: 518
aaggttctgg gcagaatcaa c                                              21

<210> SEQ ID NO 519
<211> LENGTH: 21
<212> TYPE: DNA
<213> ORGANISM: Rattus norvegicus

<400> SEQUENCE: 519
aatcaaccag ttctttgtgg c                                              21

<210> SEQ ID NO 520
<211> LENGTH: 21
<212> TYPE: DNA
<213> ORGANISM: Rattus norvegicus

<400> SEQUENCE: 520
aaccagttct ttgtggccgt c                                              21

<210> SEQ ID NO 521
<211> LENGTH: 21
<212> TYPE: DNA
<213> ORGANISM: Rattus norvegicus

<400> SEQUENCE: 521
aagatgttcg ccctgcgaca g                                              21

<210> SEQ ID NO 522
<211> LENGTH: 21
<212> TYPE: DNA
<213> ORGANISM: Rattus norvegicus

<400> SEQUENCE: 522
aacggctgga acgtgttcga c                                              21
```

```
<210> SEQ ID NO 523
<211> LENGTH: 21
<212> TYPE: DNA
<213> ORGANISM: Rattus norvegicus

<400> SEQUENCE: 523
aacgtgttcg acttcatagt g                                              21

<210> SEQ ID NO 524
<211> LENGTH: 21
<212> TYPE: DNA
<213> ORGANISM: Rattus norvegicus

<400> SEQUENCE: 524
aatccttaag tcactggaaa a                                              21

<210> SEQ ID NO 525
<211> LENGTH: 21
<212> TYPE: DNA
<213> ORGANISM: Rattus norvegicus

<400> SEQUENCE: 525
aagtcactgg aaaactactt c                                              21

<210> SEQ ID NO 526
<211> LENGTH: 21
<212> TYPE: DNA
<213> ORGANISM: Rattus norvegicus

<400> SEQUENCE: 526
aaaactactt ctccccgacg c                                              21

<210> SEQ ID NO 527
<211> LENGTH: 21
<212> TYPE: DNA
<213> ORGANISM: Rattus norvegicus

<400> SEQUENCE: 527
aactacttct ccccgacgct c                                              21

<210> SEQ ID NO 528
<211> LENGTH: 21
<212> TYPE: DNA
<213> ORGANISM: Rattus norvegicus

<400> SEQUENCE: 528 aagggattc gcacgctgct c                                               21

<210> SEQ ID NO 529
<211> LENGTH: 21
<212> TYPE: DNA
<213> ORGANISM: Rattus norvegicus

<400> SEQUENCE: 529
aacatcggcc tcctcctctt c                                              21

<210> SEQ ID NO 530
<211> LENGTH: 21
<212> TYPE: DNA
<213> ORGANISM: Rattus norvegicus

<400> SEQUENCE: 530
aacgtcgtgg acgaggccgg c                                              21
```

```
<210> SEQ ID NO 531
<211> LENGTH: 21
<212> TYPE: DNA
<213> ORGANISM: Rattus norvegicus

<400> SEQUENCE: 531
aacttcaaga cctttggcaa c                                          21

<210> SEQ ID NO 532
<211> LENGTH: 21
<212> TYPE: DNA
<213> ORGANISM: Rattus norvegicus

<400> SEQUENCE: 532
aagacctttg gcaacagcat g                                          21

<210> SEQ ID NO 533
<211> LENGTH: 21
<212> TYPE: DNA
<213> ORGANISM: Rattus norvegicus

<400> SEQUENCE: 533
aacagcatgc tgtgcctgtt c                                          21

<210> SEQ ID NO 534
<211> LENGTH: 21
<212> TYPE: DNA
<213> ORGANISM: Rattus norvegicus

<400> SEQUENCE: 534
aacacggggc ctccctactg c                                          21

<210> SEQ ID NO 535
<211> LENGTH: 21
<212> TYPE: DNA
<213> ORGANISM: Rattus norvegicus

<400> SEQUENCE: 535
aacctgccca acagcaacgg c                                          21

<210> SEQ ID NO 536
<211> LENGTH: 21
<212> TYPE: DNA
<213> ORGANISM: Rattus norvegicus

<400> SEQUENCE: 536
aacagcaacg gctcccgggg g                                          21

<210> SEQ ID NO 537
<211> LENGTH: 21
<212> TYPE: DNA
<213> ORGANISM: Rattus norvegicus

<400> SEQUENCE: 537
aacggctccc gggggaactg c                                          21

<210> SEQ ID NO 538
<211> LENGTH: 21
<212> TYPE: DNA
<213> ORGANISM: Rattus norvegicus

<400> SEQUENCE: 538
aactgcggga gcccggcggt g                                          21
```

```
<210> SEQ ID NO 539
<211> LENGTH: 21
<212> TYPE: DNA
<213> ORGANISM: Rattus norvegicus

<400> SEQUENCE: 539
aacatgtaca tcgcagtgat t                                              21

<210> SEQ ID NO 540
<211> LENGTH: 21
<212> TYPE: DNA
<213> ORGANISM: Rattus norvegicus

<400> SEQUENCE: 540
aacttcaacg tggccaccga g                                              21

<210> SEQ ID NO 541
<211> LENGTH: 21
<212> TYPE: DNA
<213> ORGANISM: Rattus norvegicus

<400> SEQUENCE: 541
aacgtggcca ccgaggagag c                                              21

<210> SEQ ID NO 542
<211> LENGTH: 21
<212> TYPE: DNA
<213> ORGANISM: Rattus norvegicus

<400> SEQUENCE: 542
aagttcgacc cggaggccac c                                              21

<210> SEQ ID NO 543
<211> LENGTH: 21
<212> TYPE: DNA
<213> ORGANISM: Rattus norvegicus

<400> SEQUENCE: 543
aatccccaaa cccaaccaga a                                              21

<210> SEQ ID NO 544
<211> LENGTH: 21
<212> TYPE: DNA
<213> ORGANISM: Rattus norvegicus

<400> SEQUENCE: 544
aaacccaacc agaatatatt a                                              21

<210> SEQ ID NO 545
<211> LENGTH: 21
<212> TYPE: DNA
<213> ORGANISM: Rattus norvegicus

<400> SEQUENCE: 545
aaccagaata tattaatcca g                                              21

<210> SEQ ID NO 546
<211> LENGTH: 21
<212> TYPE: DNA
<213> ORGANISM: Rattus norvegicus

<400> SEQUENCE: 546
aatatattaa tccagatgga c                                              21
```

```
<210> SEQ ID NO 547
<211> LENGTH: 21
<212> TYPE: DNA
<213> ORGANISM: Rattus norvegicus

<400> SEQUENCE: 547
aatccagatg gacctgccgt t                                           21

<210> SEQ ID NO 548
<211> LENGTH: 21
<212> TYPE: DNA
<213> ORGANISM: Rattus norvegicus

<400> SEQUENCE: 548
aagatccact gtctggacat c                                           21

<210> SEQ ID NO 549
<211> LENGTH: 21
<212> TYPE: DNA
<213> ORGANISM: Rattus norvegicus

<400> SEQUENCE: 549
aaagaacgtc ttgggagaat c                                           21

<210> SEQ ID NO 550
<211> LENGTH: 21
<212> TYPE: DNA
<213> ORGANISM: Rattus norvegicus

<400> SEQUENCE: 550
aacgtcttgg gagaatccgg g                                           21

<210> SEQ ID NO 551
<211> LENGTH: 21
<212> TYPE: DNA
<213> ORGANISM: Rattus norvegicus

<400> SEQUENCE: 551
aatccgggga gttggactcc c                                           21

<210> SEQ ID NO 552
<211> LENGTH: 21
<212> TYPE: DNA
<213> ORGANISM: Rattus norvegicus

<400> SEQUENCE: 552
aagaccaata tggaagagaa g                                           21

<210> SEQ ID NO 553
<211> LENGTH: 21
<212> TYPE: DNA
<213> ORGANISM: Rattus norvegicus

<400> SEQUENCE: 553
aatatggaag agaagtttat g                                           21

<210> SEQ ID NO 554
<211> LENGTH: 21
<212> TYPE: DNA
<213> ORGANISM: Rattus norvegicus

<400> SEQUENCE: 554
aagagaagtt tatggcgacc a                                           21
```

```
<210> SEQ ID NO 555
<211> LENGTH: 21
<212> TYPE: DNA
<213> ORGANISM: Rattus norvegicus

<400> SEQUENCE: 555
aagtttatgg cgaccaatct c                                              21

<210> SEQ ID NO 556
<211> LENGTH: 21
<212> TYPE: DNA
<213> ORGANISM: Rattus norvegicus

<400> SEQUENCE: 556
aatctctcca agcatccta t                                               21

<210> SEQ ID NO 557
<211> LENGTH: 21
<212> TYPE: DNA
<213> ORGANISM: Rattus norvegicus

<400> SEQUENCE: 557
aaagcatcct atgaaccaat a                                              21

<210> SEQ ID NO 558
<211> LENGTH: 21
<212> TYPE: DNA
<213> ORGANISM: Rattus norvegicus

<400> SEQUENCE: 558
aaccaatagc caccaccctc c                                              21

<210> SEQ ID NO 559
<211> LENGTH: 21
<212> TYPE: DNA
<213> ORGANISM: Rattus norvegicus

<400> SEQUENCE: 559
aatagccacc accctccggt g                                              21

<210> SEQ ID NO 560
<211> LENGTH: 21
<212> TYPE: DNA
<213> ORGANISM: Rattus norvegicus

<400> SEQUENCE: 560
aagcaggaag acctctcagc c                                              21

<210> SEQ ID NO 561
<211> LENGTH: 21
<212> TYPE: DNA
<213> ORGANISM: Rattus norvegicus

<400> SEQUENCE: 561
aagacctctc agccacagtc a                                              21

<210> SEQ ID NO 562
<211> LENGTH: 21
<212> TYPE: DNA
<213> ORGANISM: Rattus norvegicus

<400> SEQUENCE: 562
aaaaggccta ccggagctac a                                              21
```

```
<210> SEQ ID NO 563
<211> LENGTH: 21
<212> TYPE: DNA
<213> ORGANISM: Rattus norvegicus

<400> SEQUENCE: 563
aaggcctacc ggagctacat g                                              21

<210> SEQ ID NO 564
<211> LENGTH: 21
<212> TYPE: DNA
<213> ORGANISM: Rattus norvegicus

<400> SEQUENCE: 564
aacaccctgc atgtgcccag g                                              21

<210> SEQ ID NO 565
<211> LENGTH: 21
<212> TYPE: DNA
<213> ORGANISM: Rattus norvegicus

<400> SEQUENCE: 565
aaggctacgt tacattcatg g                                              21

<210> SEQ ID NO 566
<211> LENGTH: 21
<212> TYPE: DNA
<213> ORGANISM: Rattus norvegicus

<400> SEQUENCE: 566
aaacagtgga ctcccggaca a                                              21

<210> SEQ ID NO 567
<211> LENGTH: 21
<212> TYPE: DNA
<213> ORGANISM: Rattus norvegicus

<400> SEQUENCE: 567
aaatcagaaa ctgcctctgc t                                              21

<210> SEQ ID NO 568
<211> LENGTH: 21
<212> TYPE: DNA
<213> ORGANISM: Rattus norvegicus

<400> SEQUENCE: 568
aaactgcctc tgctacgtct t                                              21

<210> SEQ ID NO 569
<211> LENGTH: 21
<212> TYPE: DNA
<213> ORGANISM: Rattus norvegicus

<400> SEQUENCE: 569
aacattaacc catctagctc a                                              21

<210> SEQ ID NO 570
<211> LENGTH: 21
<212> TYPE: DNA
<213> ORGANISM: Rattus norvegicus

<400> SEQUENCE: 570
aacccatcta gctcaatgca a                                              21
```

<210> SEQ ID NO 571
<211> LENGTH: 21
<212> TYPE: DNA
<213> ORGANISM: Rattus norvegicus

<400> SEQUENCE: 571
aatgcaaaat gaagatgagg t                                              21

<210> SEQ ID NO 572
<211> LENGTH: 21
<212> TYPE: DNA
<213> ORGANISM: Rattus norvegicus

<400> SEQUENCE: 572
aaaatgaaga tgaggtcgct g                                              21

<210> SEQ ID NO 573
<211> LENGTH: 21
<212> TYPE: DNA
<213> ORGANISM: Rattus norvegicus

<400> SEQUENCE: 573
aatgaagatg aggtcgctgc t                                              21

<210> SEQ ID NO 574
<211> LENGTH: 21
<212> TYPE: DNA
<213> ORGANISM: Rattus norvegicus

<400> SEQUENCE: 574
aagatgaggt cgctgctaag g                                              21

<210> SEQ ID NO 575
<211> LENGTH: 21
<212> TYPE: DNA
<213> ORGANISM: Rattus norvegicus

<400> SEQUENCE: 575
aaggaaggaa acagccctgg a                                              21

<210> SEQ ID NO 576
<211> LENGTH: 21
<212> TYPE: DNA
<213> ORGANISM: Rattus norvegicus

<400> SEQUENCE: 576
aaggaaacag ccctggacct c                                              21

<210> SEQ ID NO 577
<211> LENGTH: 21
<212> TYPE: DNA
<213> ORGANISM: Rattus norvegicus

<400> SEQUENCE: 577
aaacagccct ggacctcagt g                                              21